US008808991B2

(12) United States Patent
Hodgers

(10) Patent No.: US 8,808,991 B2
(45) Date of Patent: Aug. 19, 2014

(54) OLA-BASED METHODS FOR THE DETECTION OF TARGET NUCLEIC AVID SEQUENCES

(75) Inventor: René Cornelis Josephus Hodgers, Ede (NL)

(73) Assignee: Keygene N.V., Wageningen (NL)

( * ) Notice: Subject to any disclaimer, the term of this patent is extended or adjusted under 35 U.S.C. 154(b) by 1387 days.

(21) Appl. No.: 10/570,249

(22) PCT Filed: Aug. 31, 2004

(86) PCT No.: PCT/NL2004/000604
§ 371 (c)(1),
(2), (4) Date: Apr. 19, 2007

(87) PCT Pub. No.: WO2005/021794
PCT Pub. Date: Mar. 10, 2005

(65) Prior Publication Data
US 2007/0269805 A1    Nov. 22, 2007

Related U.S. Application Data

(60) Provisional application No. 60/582,716, filed on Jun. 25, 2004.

(30) Foreign Application Priority Data

Sep. 2, 2003  (NL) ........................ PCT/NL03/00613
Jun. 2, 2004  (EP) .................................. 040766180

(51) Int. Cl.
*C12Q 1/68* (2006.01)
*C12P 19/34* (2006.01)
*C07H 21/04* (2006.01)

(52) U.S. Cl.
CPC ............ *C12Q 1/6858* (2013.01); *C12Q 1/6827* (2013.01); *C12Q 1/6862* (2013.01)
USPC ... 435/6.12; 435/91.2; 536/24.31; 536/24.32; 536/24.33

(58) Field of Classification Search
USPC ...................... 435/6; 536/24.31, 24.32, 24.33
See application file for complete search history.

(56) References Cited

U.S. PATENT DOCUMENTS 7,498,131 B2 *   3/2009   Van Eijk et al. ............. 435/6.12

FOREIGN PATENT DOCUMENTS

| EP | 1 130 113 A1 * | 5/2001 |
|---|---|---|
| EP | 1 130 113 A1 | 9/2001 |
| EP | 1 319 718 A1 | 8/2003 |
| WO | WO 95/01456 A1 | 1/1995 |
| WO | WO 96/15271 A1 | 5/1996 |
| WO | WO 97/45559 A1 | 12/1997 |
| WO | WO 01/06012 A1 | 1/2001 |
| WO | WO 01/57256 a2 | 8/2001 |
| WO | WO 02/46464 A2 | 6/2002 |
| WO | WO 02/057491 A2 * | 7/2002 |
| WO | 03/052142 A2 | 6/2003 |
| WO | WO 03/060163 A2 | 7/2003 |

OTHER PUBLICATIONS

Grossman, P.D. et al., "High-density multiplex detection of nucleic acid seuquences: oligonucleotide ligation assay and sequence-coded separation" Nucleic Acids Research, (1994), vol. 22, No. 21, pp. 4527-4534.
Hardenbol P., et al., "Multiplexed genotyping with sequence-tagged molecular inversion probes", Nature Biotechnology (Jun. 2003), vol. 21, No. 6, pp. 673-678.
Lin Z. et al., "Multiplex genotype determination at a large number of gene loci", Proceedings of the National Academy of Science, (Mar. 19, 1996), vol. 93, No. 6, pp. 2582-2587.
Schouten et al., Relative quantification of 40 nucleic acid sequences by multiplex ligation-dependent probe amplification, Nucleic Acids Research, 30(12 e57)1-13 (2002).
Demchinskaya et al., A new approach for point mutation detection based on a ligase chain reaction, J. Biochem. Biophys. Methods, 50:79-89 (2001).
Lin et al., Multiplex genotype determination at a large umber of gene loci, Proc. Natl. Acad. Sci. USA, 93:2582-2587 (Mar. 1996).

* cited by examiner

*Primary Examiner* — Prabha Chunduru
(74) *Attorney, Agent, or Firm* — Sunit Talapatra; Tianran Yan; Foley & Lardner LLP

(57) ABSTRACT

Method for the detection of a target sequence comprising ligating two probes when annealed adjacent to the target sequence, hybridization of a compound primer to the ligated probes and after elongation of the compound primer, amplifying the elongated compound primer from primers annealing to primer binding sites provided in the compound primer and one of the probes to produce detectably amplicons.

19 Claims, 7 Drawing Sheets

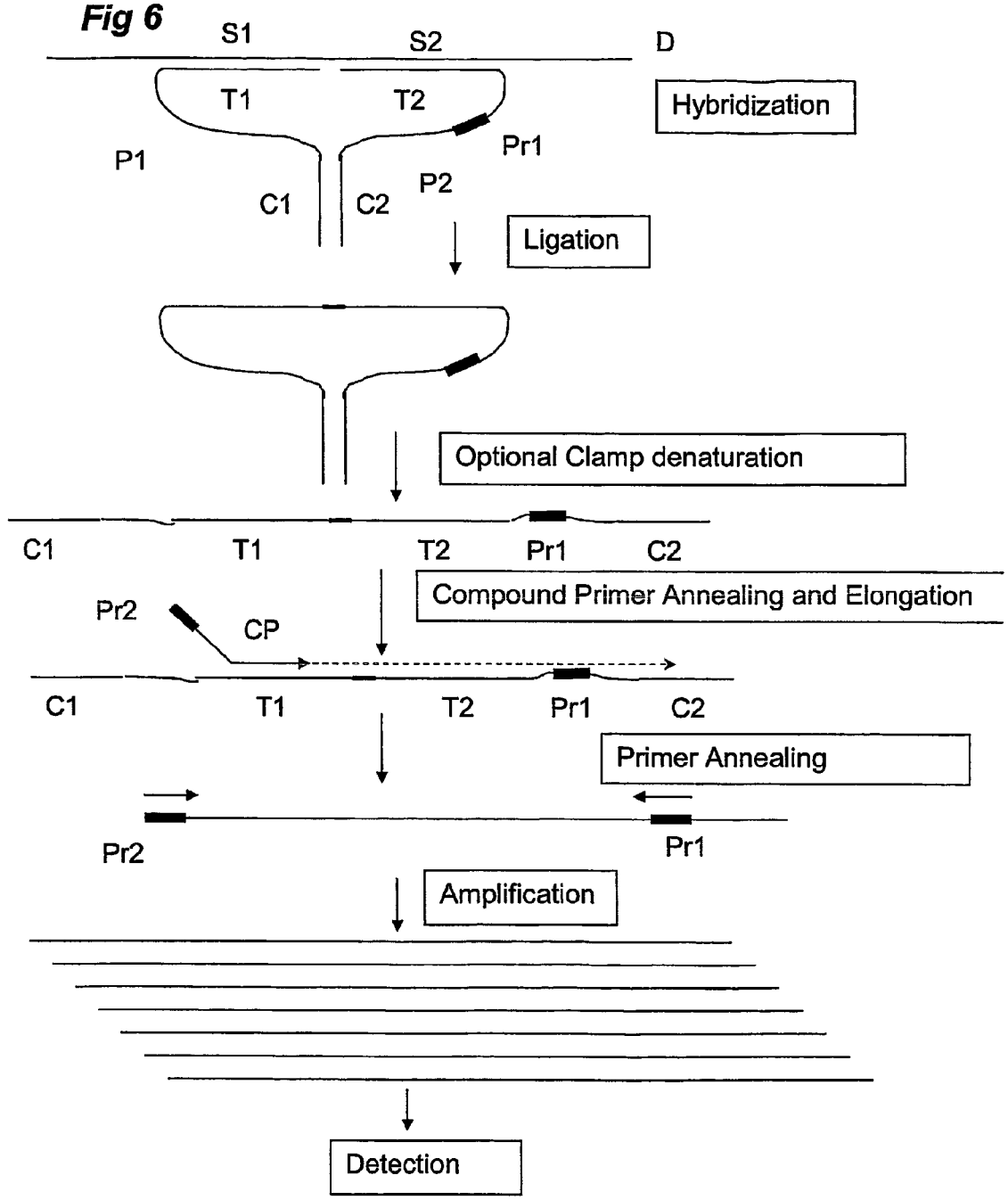

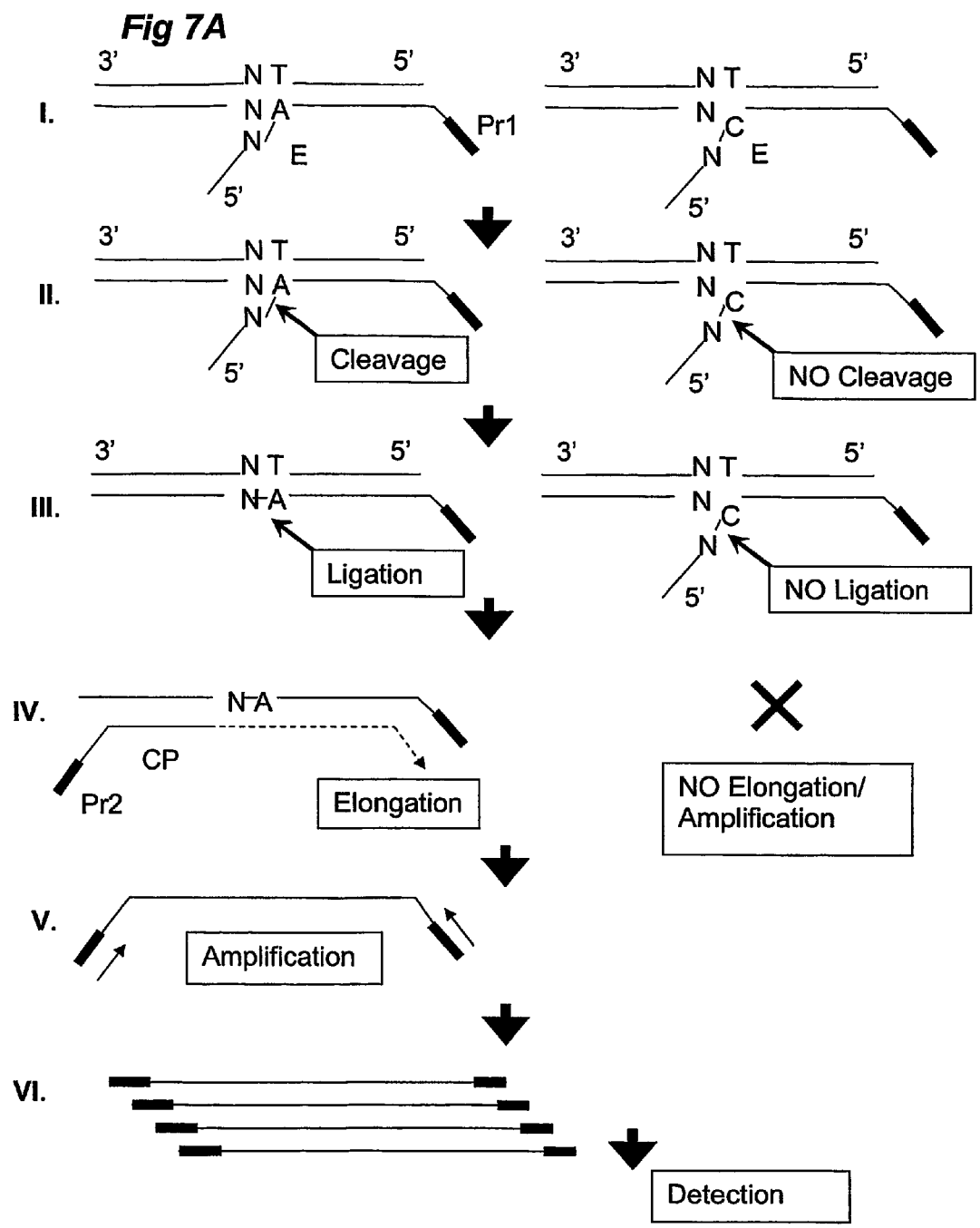

Fig 7B
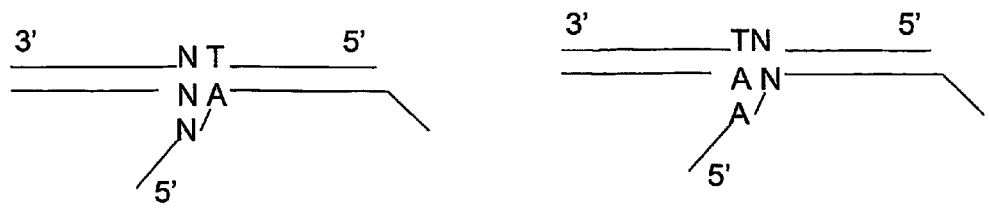
Fig 8
Probe types:
1. Linear Probes  
2. Padlock/circularizable Probes  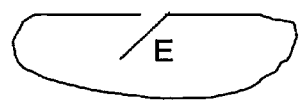
3. Kevlock/semi-circularizable Probes  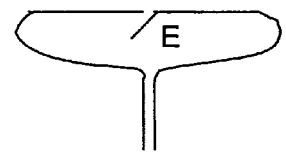
4. Compound primer of the present invention  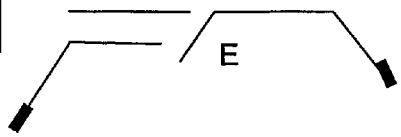

SEQUENCE LISTING

<160> NUMBER OF SEQ ID NOS: 62

<210> SEQ ID NO 1
<211> LENGTH: 16
<212> TYPE: DNA
<213> ORGANISM: artificial
<220> FEATURE:
<223> OTHER INFORMATION: oligonucleotide primer

<400> SEQUENCE: 1
gatgagtcct gagtaa                                                    16

<210> SEQ ID NO 2
<211> LENGTH: 16
<212> TYPE: DNA
<213> ORGANISM: artificial
<220> FEATURE:

<223> OTHER INFORMATION: oligonucleotide primer

<400> SEQUENCE: 2
gactgcgtac caattc                                                     16

<210> SEQ ID NO 3
<211> LENGTH: 472
<212> TYPE: DNA
<213> ORGANISM: Lycopersicon esculentum

<400> SEQUENCE: 3
tatccactca ggtctccgca agccagaaat gggatataca ccttgttacg accytcaagc    60
catccactac tgcaatctgt catgtcacag atgttcggaa gataatgtat aagtacaact   120
atatagtcgg awttgcatct agtctagcat tcggaaaatg gaagccatgc tacttctagc   180
ataaaaaaca gcagctagaa atcgtaactc caatgatacg aggaagtatt cagagtttag   240
agtgawgtac aatgcaattt agagaacaag catctgcaca tcraagttac ctaggtcctc   300
agcgcctgat ggacttccaa cttgttcaag aaggcgataa aggtctttct cattgaatcc   360
ttcaggtgga gagtagtttt cacaaactgc aaatgcctct gcacagcgga aagattgaat   420
tagatttatg ttatatagcc attctagtct tgctttaatg gatctttctc ga            472

<210> SEQ ID NO 4
<211> LENGTH: 222
<212> TYPE: DNA
<213> ORGANISM: Lycopersicon esculentum

<400> SEQUENCE: 4
ccacagtttc atgctgcacc tacatgtgta agcaactatc atagcaagtc tcggaacaat    60
tggtaggaaa aaatcmykta aggatatgaa acatactgty ctttcttcat ctgagtctgy   120
agagttaatt tttaactctt gggataaatg caaagawtta gacatggakg agtycttaac   180
acgtccagac aagaggcgta acacaggtac acctttctc ga                       222

<210> SEQ ID NO 5
<211> LENGTH: 133
<212> TYPE: DNA
<213> ORGANISM: Lycopersicon esculentum

<400> SEQUENCE: 5
ttgtgcttga tgaattgtag gtccagtgca ggtttgcttc taaaacaggg agcactttgc    60
aagtggtgaa agttctatta gctgggaaag tgtagtttga gcagttttga gctgarttaa   120
caagaaaaat cga                                                      133

<210> SEQ ID NO 6
<211> LENGTH: 249
<212> TYPE: DNA
<213> ORGANISM: Lycopersicon esculentum

<400> SEQUENCE: 6
ccgccactgg gtaattgagt ttcatattga tggttttgtt tttgttracg cttcttcctt    60
gttgagaggg ttcaatggag agattctatc tcgtcctcca ttagttgaag ctattgcctt   120
tgatcctatc ctttcaaagg ycaagatgat tgcagataat tggaatccat taaccaatga   180
ttctacggaa aatttattcc ctcactggag gagatgggca gagataaata tgagattttg   240
tgatgacat                                                           249

<210> SEQ ID NO 7
<211> LENGTH: 284
<212> TYPE: DNA
<213> ORGANISM: Lycopersicon esculentum

<400> SEQUENCE: 7

```
tcgagtaagg cggatggata tggaacaagc catttcaagg agcaatttcc caggattttc      60
agctttgcaa cagcagaagt gtayctctgc agagatagat cataaccttt ggaaaggtgt     120
agtaattgtc aaagggagga atgagccagg aaactgatag actatgttgc gaaaataagc     180
tatacttcac taaaaaaagg ctagacgttt gagaaatgaa gcaagaacta acacctctca     240
ccaattgcat cattttctta gttcagttga tgtgatgagc ttgt                      284
```

<210> SEQ ID NO 8
<211> LENGTH: 320
<212> TYPE: DNA
<213> ORGANISM: Lycopersicon esculentum

<400> SEQUENCE: 8

```
tcgatatccw ctcttgtttg ttgcaggagc wgaactataa attgcttgca ggaaccttga      60
catatgcttt ctgttgagac ttgaatcacc agcatggatt tgaatgcctt gccacagcca     120
gaggatgacg aygagatttt tggacaacaa ttagaagatg aaccacaaga acctatttta     180
cgtagtgatg agcstgcaga ttatgtcacg agtgctgtag agatttcacg tcgcgtatgt     240
ttctgcttat actgctcgct gtatcaacta ttgaacygta ctactacttg arcttgctcg     300
tttattggat atttctttttt                                                320
```

<210> SEQ ID NO 9
<211> LENGTH: 191
<212> TYPE: DNA
<213> ORGANISM: Lycopersicon esculentum

<400> SEQUENCE: 9

```
gaattcacac tasgttcgat gaaattgaaa cgttctcttt ctgaagaaka tacacaagaa      60
aaaatcttat agtcctcaac aatattcttc ttcgtaacag aaaacacgga agaaaatctc     120
ttctgaaaat ccctataatc actggctgga acttctccsa actctcaatt tttcaacctt     180
ctctatgtta a                                                          191
```

<210> SEQ ID NO 10
<211> LENGTH: 279
<212> TYPE: DNA
<213> ORGANISM: Lycopersicon esculentum

<400> SEQUENCE: 10

```
ctgcagaadt actgtttgtt caggacttac taaatatcct aaacaaaatt gatgatagag      60
ccaataatgt atgcatgatt ggcggtccrt tcttttgtta tagcaagagc ttgaagctaa     120
ttttgtttgt cataatggcc gcactaattg tttattatct cagaatgaac aaaagaagc     180
aagtcagaag ctttstactc tatactgaac aactttggaa ttggaactat gtacttatct     240
agccacgcct catagatctt tgtggtttag gagtgttaa                            279
```

<210> SEQ ID NO 11
<211> LENGTH: 336
<212> TYPE: DNA
<213> ORGANISM: Lycopersicon esculentum

<400> SEQUENCE: 11

```
gaattcacaa tgaaaaakgk dgtaaaaaca cgaaatcaat caagcatgca agagataatg      60
ttgtccatcc agttgttgtt gatgtttcgg tattgtatgt gtgttgggag gagttatctg     120
grcagcaagt cgaggtttga acgtcaaaaa ggtatgggtt gtcttctctc tttgtccctt     180
ttcgaagaga cccctaaggt tcagacgaat ctattccaaa aactagggtt gttccttgtt     240
gcatctcctt ktcacaagct cccatcgcat cataagtagg gtatgtttga tggtagaatt     300
tacggatgta atttactttt gaaatgatta tgttaa                              336
```

<210> SEQ ID NO 12
<211> LENGTH: 373
<212> TYPE: DNA
<213> ORGANISM: Lycopersicon esculentum

<400> SEQUENCE: 12

```
agagagacga gagctcgact agtgatagtg ttatgtgcaa cagttgaata gaaagatgya      60
cacgagcctc ggatcaatgg cagggaaaga ggcgtggtgc tacgaaccat aaaggcaagg     120
ttgagctttc ctttacagag tacatcgcct attccatact ccgctgatac tctttgataa     180
atcaaaatct gtggtgatct cgtagttctt ggggatccca gccaaaacca ccttcgaggt     240
tcaacacaac atagacagta tggcagaata tcaagacaat gactgctcga aactgctgat     300
ggcattatgt gcaaccgttg aatagagaga tgtacacgag tctcggatca atggcaggaa     360
aagagagtgc ttg                                                       373
```

<210> SEQ ID NO 13
<211> LENGTH: 45
<212> TYPE: DNA
<213> ORGANISM: artificial
<220> FEATURE:
<223> OTHER INFORMATION: oligonucleotide probe

<400> SEQUENCE: 13

```
gtacaatgca atttagagaa caagcccggg cggcccgggc gcggc                      45
```

<210> SEQ ID NO 14
<211> LENGTH: 43
<212> TYPE: DNA
<213> ORGANISM: artificial
<220> FEATURE:
<223> OTHER INFORMATION: oligonucleotide probe

<400> SEQUENCE: 14

```
cttaacacgt ccagacaaga ggccgcgggc gcgcggcggg cgg                        43
```

<210> SEQ ID NO 15
<211> LENGTH: 45
<212> TYPE: DNA
<213> ORGANISM: artificial
<220> FEATURE:
<223> OTHER INFORMATION: oligonucleotide probe

<400> SEQUENCE: 15

```
ttaacaagaa aaatcggtca ggactcgcgg cgcccgcggc gcggg                      45
```

<210> SEQ ID NO 16
<211> LENGTH: 43
<212> TYPE: DNA
<213> ORGANISM: artificial
<220> FEATURE:
<223> OTHER INFORMATION: oligonucleotide probe

<400> SEQUENCE: 16
acgcttcttc cttgttgaga gggcgccggc cgggcccgcc ggc         43

<210> SEQ ID NO 17
<211> LENGTH: 44
<212> TYPE: DNA
<213> ORGANISM: artificial
<220> FEATURE:
<223> OTHER INFORMATION: oligonucleotide probe

<400> SEQUENCE: 17
ctctgcagag atagatcata acctggcccg cgcgcccggc ggcg        44

<210> SEQ ID NO 18
<211> LENGTH: 45
<212> TYPE: DNA
<213> ORGANISM: artificial
<220> FEATURE:
<223> OTHER INFORMATION: oligonucleotide probe

<400> SEQUENCE: 18
gaactataaa ttgcttgcag gaaccgggcg gcccggcccg cccgg       45

<210> SEQ ID NO 19
<211> LENGTH: 46
<212> TYPE: DNA
<213> ORGANISM: artificial
<220> FEATURE:
<223> OTHER INFORMATION: oligonucleotide probe

<400> SEQUENCE: 19
aactctcaat ttttcaacct tctctacgcg ccgggccgcg gccggc      46

<210> SEQ ID NO 20
<211> LENGTH: 46
<212> TYPE: DNA
<213> ORGANISM: artificial
<220> FEATURE:
<223> OTHER INFORMATION: oligonucleotide probe

<400> SEQUENCE: 20
ttcttttgtt atagcaagag cttgaagccg gccggccgcg cgcggg      46

<210> SEQ ID NO 21
<211> LENGTH: 42
<212> TYPE: DNA
<213> ORGANISM: artificial
<220> FEATURE:
<223> OTHER INFORMATION: oligonucleotide probe

<400> SEQUENCE: 21
tcacaagctc ccatcgcatc atcggcgcgc gggccgcgcg cc          42

<210> SEQ ID NO 22
<211> LENGTH: 40
<212> TYPE: DNA
<213> ORGANISM: artificial
<220> FEATURE:
<223> OTHER INFORMATION: oligonucleotide probe

<400> SEQUENCE: 22
acacgagcct cggatcaatg cggcccgccc ggcggccgcc             40

<210> SEQ ID NO 23
<211> LENGTH: 45
<212> TYPE: DNA

```
<213> ORGANISM: artificial
<220> FEATURE:
<223> OTHER INFORMATION: oligonucleotide probe

<400> SEQUENCE: 23
gtacaatgca atttagagaa caagcccggg cggcccgggc gcggc            45

<210> SEQ ID NO 24
<211> LENGTH: 43
<212> TYPE: DNA
<213> ORGANISM: artificial
<220> FEATURE:
<223> OTHER INFORMATION: oligonucleotide probe

<400> SEQUENCE: 24
cttaacacgt ccagacaaga ggccgcgggc gcgcggcggg cgg              43

<210> SEQ ID NO 25
<211> LENGTH: 45
<212> TYPE: DNA
<213> ORGANISM: artificial
<220> FEATURE:
<223> OTHER INFORMATION: oligonucleotide probe

<400> SEQUENCE: 25
ttaacaagaa aaatcggtca ggactcgcgg cgcccgcggc gcggg            45

<210> SEQ ID NO 26
<211> LENGTH: 43
<212> TYPE: DNA
<213> ORGANISM: artificial
<220> FEATURE:
<223> OTHER INFORMATION: oligonucleotide probe

<400> SEQUENCE: 26
acgcttcttc cttgttgaga gggcgccggc cgggcccgcc ggc              43

<210> SEQ ID NO 27
<211> LENGTH: 44
<212> TYPE: DNA
<213> ORGANISM: artificial
<220> FEATURE:
<223> OTHER INFORMATION: oligonucleotide probe

<400> SEQUENCE: 27
ctctgcagag atagatcata acctggcccg cgcgcccggc ggcg             44

<210> SEQ ID NO 28
<211> LENGTH: 45
<212> TYPE: DNA
<213> ORGANISM: artificial
<220> FEATURE:
<223> OTHER INFORMATION: oligonucleotide probe

<400> SEQUENCE: 28
gaactataaa ttgcttgcag gaaccgggcg gcccggcccg cccgg            45

<210> SEQ ID NO 29
<211> LENGTH: 46
<212> TYPE: DNA
<213> ORGANISM: artificial
<220> FEATURE:
<223> OTHER INFORMATION: oligonucleotide probe]

<400> SEQUENCE: 29
aactctcaat ttttcaacct tctctacgcg ccgggccgcg gccggc           46
```

<210> SEQ ID NO 30
<211> LENGTH: 46
<212> TYPE: DNA
<213> ORGANISM: artificial
<220> FEATURE:
<223> OTHER INFORMATION: oligonucleotide probe

<400> SEQUENCE: 30
ttcttttgtt atagcaagag cttgaagccg gccggccgcg cgcggg           46

<210> SEQ ID NO 31
<211> LENGTH: 42
<212> TYPE: DNA
<213> ORGANISM: artificial
<220> FEATURE:
<223> OTHER INFORMATION: oligonucleotide probe

<400> SEQUENCE: 31
tcacaagctc ccatcgcatc atcggcgcgc gggccgcgcg cc               42

<210> SEQ ID NO 32
<211> LENGTH: 40
<212> TYPE: DNA
<213> ORGANISM: artificial
<220> FEATURE:
<223> OTHER INFORMATION: oligonucleotide probe

<400> SEQUENCE: 32
acacgagcct cggatcaatg cggcccgccc ggcggccgcc                  40

<210> SEQ ID NO 33
<211> LENGTH: 65
<212> TYPE: DNA
<213> ORGANISM: artificial
<220> FEATURE:
<223> OTHER INFORMATION: oligonucleotide probe

<400> SEQUENCE: 33
gccgcgcccg ggccgccgg gatgagtcct gagtaacgct ggaagtattc agagtttaga    60
gtgaa                                                               65

<210> SEQ ID NO 34
<211> LENGTH: 63
<212> TYPE: DNA
<213> ORGANISM: artificial
<220> FEATURE:
<223> OTHER INFORMATION: oligonucleotide probe

<400> SEQUENCE: 34
gccgcgcccg ggccgccgg gatgagtcct gagtaacggg aagtattcag agtttagagt    60
gat                                                                 63

<210> SEQ ID NO 35
<211> LENGTH: 65
<212> TYPE: DNA
<213> ORGANISM: artificial
<220> FEATURE:
<223> OTHER INFORMATION: oligonucleotide probe

<400> SEQUENCE: 35
ccgcccgccg cgcgcccgcg gatgagtcct gagtaacgca gcaaagaatt agacatggat    60
gagtt                                                                65

<210> SEQ ID NO 36
<211> LENGTH: 63
<212> TYPE: DNA
<213> ORGANISM: artificial
<220> FEATURE:
<223> OTHER INFORMATION: oligonucleotide probe

<400> SEQUENCE: 36
ccgcccgccg cgcgcccgcg gatgagtcct gagtaacgcc aaagatttag acatggagga    60
gtc    63

<210> SEQ ID NO 37
<211> LENGTH: 64
<212> TYPE: DNA
<213> ORGANISM: artificial
<220> FEATURE:
<223> OTHER INFORMATION: oligonucleotide probe

<400> SEQUENCE: 37
cccgcgccgc gggcgccgcg gatgagtcct gagtaacgcc tagtttgagc agttttgagc    60
tgaa    64

<210> SEQ ID NO 38
<211> LENGTH: 62
<212> TYPE: DNA
<213> ORGANISM: artificial
<220> FEATURE:
<223> OTHER INFORMATION: oligonucleotide probe

<400> SEQUENCE: 38
cccgcgccgc gggcgccgcg gatgagtcct gagtaacgta gtttgagcag ttttgagctg    60
ag    62

<210> SEQ ID NO 39
<211> LENGTH: 67
<212> TYPE: DNA
<213> ORGANISM: artificial
<220> FEATURE:
<223> OTHER INFORMATION: oligonucleotide probe

<400> SEQUENCE: 39
gccggcgggc cggccggcg gatgagtcct gagtaacgcc ttcatattga tggttttgtt    60
tttgtta    67

<210> SEQ ID NO 40
<211> LENGTH: 65
<212> TYPE: DNA
<213> ORGANISM: artificial
<220> FEATURE:
<223> OTHER INFORMATION: oligonucleotide probe

<400> SEQUENCE: 40
gccggcgggc cggccggcg gatgagtcct gagtaacgtt catattgatg gttttgtttt    60
tgttg    65

<210> SEQ ID NO 41
<211> LENGTH: 64
<212> TYPE: DNA
<213> ORGANISM: artificial
<220> FEATURE:
<223> OTHER INFORMATION: oligonucleotide probe

<400> SEQUENCE: 41

-continued

```
cgccgccggg cgcgcgggcc gatgagtcct gagtaacgca agctttgcaa cagcagaagt    60
gtat                                                                 64

<210> SEQ ID NO 42
<211> LENGTH: 62
<212> TYPE: DNA
<213> ORGANISM: artificial
<220> FEATURE:
<223> OTHER INFORMATION: oligonucleotide probe

<400> SEQUENCE: 42
cgccgccggg cgcgcgggcc gatgagtcct gagtaacgag ctttgcaaca gcagaagtgt    60
ac                                                                   62

<210> SEQ ID NO 43
<211> LENGTH: 63
<212> TYPE: DNA
<213> ORGANISM: artificial
<220> FEATURE:
<223> OTHER INFORMATION: oligonucleotide probe

<400> SEQUENCE: 43
ccgggcgggc cgggccgccc gatgagtcct gagtaacgct ctctcttgtt tgttgcagga    60
gca                                                                  63

<210> SEQ ID NO 44
<211> LENGTH: 61
<212> TYPE: DNA
<213> ORGANISM: artificial
<220> FEATURE:
<223> OTHER INFORMATION: oligonucleotide probe

<400> SEQUENCE: 44
ccgggcgggc cgggccgccc gatgagtcct gagtaacgca ctcttgtttg ttgcaggagc    60
t                                                                    61

<210> SEQ ID NO 45
<211> LENGTH: 62
<212> TYPE: DNA
<213> ORGANISM: artificial
<220> FEATURE:
<223> OTHER INFORMATION: oligonucleotide probe

<400> SEQUENCE: 45
gccggccgcg gcccggcgcg gatgagtcct gagtaacgcg atcactggct ggaacttctc    60
cc                                                                   62

<210> SEQ ID NO 46
<211> LENGTH: 60
<212> TYPE: DNA
<213> ORGANISM: artificial
<220> FEATURE:
<223> OTHER INFORMATION: oligonucleotide probe

<400> SEQUENCE: 46
gccggccgcg gcccggcgcg gatgagtcct gagtaacgat cactggctgg aacttctccg    60

<210> SEQ ID NO 47
<211> LENGTH: 63
<212> TYPE: DNA
<213> ORGANISM: artificial
<220> FEATURE:
```

<223> OTHER INFORMATION: oligonucleotide probe

<400> SEQUENCE: 47
cccgcgcgcg gccggccggc gatgagtcct gagtaacgcc atgtatgcat gattggcggt    60
cca    63

<210> SEQ ID NO 48
<211> LENGTH: 61
<212> TYPE: DNA
<213> ORGANISM: artificial
<220> FEATURE:
<223> OTHER INFORMATION: oligonucleotide probe

<400> SEQUENCE: 48
cccgcgcgcg gccggccggc gatgagtcct gagtaacgat gtatgcatga ttggcggtcc    60
g    61

<210> SEQ ID NO 49
<211> LENGTH: 64
<212> TYPE: DNA
<213> ORGANISM: artificial
<220> FEATURE:
<223> OTHER INFORMATION: oligonucleotide probe

<400> SEQUENCE: 49
ggcgcgcggc ccgcgcgccg gatgagtcct gagtaacgct gttgttcctt gttgcatctc    60
cttt    64

<210> SEQ ID NO 50
<211> LENGTH: 62
<212> TYPE: DNA
<213> ORGANISM: artificial
<220> FEATURE:
<223> OTHER INFORMATION: oligonucleotide probe

<400> SEQUENCE: 50
ggcgcgcggc ccgcgcgccg gatgagtcct gagtaacggt tgttccttgt tgcatctcct    60
tg    62

<210> SEQ ID NO 51
<211> LENGTH: 62
<212> TYPE: DNA
<213> ORGANISM: artificial
<220> FEATURE:
<223> OTHER INFORMATION: oligonucleotide probe

<400> SEQUENCE: 51
ggcggccgcc gggcgggccg gatgagtcct gagtaacgtg caacagttga atagaaagat    60
gt    62

<210> SEQ ID NO 52
<211> LENGTH: 60
<212> TYPE: DNA
<213> ORGANISM: artificial
<220> FEATURE:
<223> OTHER INFORMATION: oligonucleotide probe

<400> SEQUENCE: 52
ggcggccgcc gggcgggccg gatgagtcct gagtaacgca acagttgaat agaaagatgc    60

<210> SEQ ID NO 53
<211> LENGTH: 79

```
<212> TYPE: DNA
<213> ORGANISM: artificial
<220> FEATURE:
<223> OTHER INFORMATION: oligonucleotide probe

<400> SEQUENCE: 53
gactgcgtac caattccccg attacgatgc agctacgtcg atatcgatcg gatcgcttgt    60
tctctaaatt gcattgtac                                                 79

<210> SEQ ID NO 54
<211> LENGTH: 74
<212> TYPE: DNA
<213> ORGANISM: artificial
<220> FEATURE:
<223> OTHER INFORMATION: oligonucleotide probe

<400> SEQUENCE: 54
gactgcgtac caattcccga ctcagtgcta tacggatcta cgtcgacatg ggcctcttgt    60
ctggacgtgt taag                                                      74

<210> SEQ ID NO 55
<211> LENGTH: 70
<212> TYPE: DNA
<213> ORGANISM: artificial
<220> FEATURE:
<223> OTHER INFORMATION: oligonucleotide probe

<400> SEQUENCE: 55
gactgcgtac caattcccga tagtccgtaa cgttagcatg cgtacagtcc tgaccgattt    60
ttcttgttaa                                                           70

<210> SEQ ID NO 56
<211> LENGTH: 62
<212> TYPE: DNA
<213> ORGANISM: artificial
<220> FEATURE:
<223> OTHER INFORMATION: oligonucleotide probe

<400> SEQUENCE: 56
gactgcgtac caattcccca tgtcgatagc ctgagcatcc cctctcaaca aggaagaagc    60
gt                                                                   62

<210> SEQ ID NO 57
<211> LENGTH: 60
<212> TYPE: DNA
<213> ORGANISM: artificial
<220> FEATURE:
<223> OTHER INFORMATION: oligonucleotide probe

<400> SEQUENCE: 57
gactgcgtac caattcccat gctcagcatg acgtgaaggt tatgatctat ctctgcagag    60

<210> SEQ ID NO 58
<211> LENGTH: 56
<212> TYPE: DNA
<213> ORGANISM: artificial
<220> FEATURE:
<223> OTHER INFORMATION: oligonucleotide probe

<400> SEQUENCE: 58
gactgcgtac caattccccg taacgttagc gggttcctgc aagcaattta tagttc        56

<210> SEQ ID NO 59
```

```
<211> LENGTH: 52
<212> TYPE: DNA
<213> ORGANISM: artificial
<220> FEATURE:
<223> OTHER INFORMATION: oligonucleotide probe

<400> SEQUENCE: 59
gactgcgtac caattccctc gaatgataga gaaggttgaa aaattgagag tt        52

<210> SEQ ID NO 60
<211> LENGTH: 46
<212> TYPE: DNA
<213> ORGANISM: artificial
<220> FEATURE:
<223> OTHER INFORMATION: oligonucleotide probe

<400> SEQUENCE: 60
gactgcgtac caattccccg ttcaagctct tgctataaca aaagaa              46

<210> SEQ ID NO 61
<211> LENGTH: 40
<212> TYPE: DNA
<213> ORGANISM: artificial
<220> FEATURE:
<223> OTHER INFORMATION: oligonucleotide probe

<400> SEQUENCE: 61
gactgcgtac caattcccat gatgcgatgg gagcttgtga                     40

<210> SEQ ID NO 62
<211> LENGTH: 37
<212> TYPE: DNA
<213> ORGANISM: artificial
<220> FEATURE:
<223> OTHER INFORMATION: oligonucleotide probe

<400> SEQUENCE: 62
gactgcgtac caattcccat tgatccgagg ctcgtgt                        37
```

OLA-BASED METHODS FOR THE DETECTION OF TARGET NUCLEIC AVID SEQUENCES

FIELD OF THE INVENTION

The present invention relates to the field of molecular biology and biotechnology. In particular the invention relates to the field of nucleic acid detection, more in particular to the design and composition of (collections) of probes that can be used for the detection of nucleic acids. The invention also relates to methods for detection of nucleic acids using the probes and compositions. The invention further provides for probes that are capable of hybridising to a target sequence of interest, primers for the amplification of ligated probes, use of these probes and primers in the identification and/or detection of nucleotide sequences that are related to a wide variety of genetic traits and genes and kits of primers and/or probes suitable for use in the method according to the invention.

BACKGROUND OF THE INVENTION

There is a rapidly growing interest in the detection of specific nucleic acid sequences. This interest has not only arisen from the recently disclosed draft nucleotide sequence of the human genome and the presence therein, as well as in the genomes of many other organisms, of an abundant amount of single nucleotide polymorphisms (SNP), but also from marker technologies such as AFLP and the general recognition of the relevance of the detection of specific nucleic acid sequences as an indication of for instance genetically inheritable diseases. The detection of the various alleles of the breast cancer gene BRCA 1 to screen for susceptibility for breast cancer is just one of numerous examples. The recognition that the presence of single nucleotide substitutions (and other types of genetic polymorphisms such as small insertion/deletions; indels) in genes provide a wide variety of information has also attributed to this increased interest. It is now generally recognised that these single nucleotide substitutions are one of the main causes of a significant number of monogenically and multigenically inherited diseases, for instance in humans, or are otherwise involved in the development of complex phenotypes such as performance traits in plants and livestock species. Thus, single nucleotide substitutions are in many cases also related to or at least indicative of important traits in humans, plants and animal species.

Analysis of these single nucleotide substitutions and indels will result in a wealth of valuable information, which will have widespread implications on medicine and agriculture in the widest possible terms. It is for instance generally envisaged that these developments will result in patient-specific medication. To analyse these genetic polymorphisms, there is a growing need for adequate, reliable and fast methods that enable the handling of large numbers of samples and large numbers of (predominantly) SNPs in a high throughput fashion, without significantly compromising the quality of the data obtained. One of the principal methods used for the analysis of the nucleic acids of a known sequence is based on annealing two probes to a target sequence and, when the probes are hybridised adjacently to the target sequence, ligating the probes. This concept is commonly indicated as the Oligonucleotide Ligation Assay or Oligonucleotide Ligation Amplification (OLA)

The OLA-principle has been described, amongst others, in U.S. Pat. No. 4,988,617 (Landegren et al.). This publication discloses a method for determining the nucleic acid sequence in a region of a known nucleic acid sequence having a known possible mutation. To detect the mutation, oligonucleotides are selected to anneal to immediately adjacent segments of the sequence to be determined. One of the selected oligonucleotide probes has an end region wherein one of the end region nucleotides is complementary to either the normal or to the mutated nucleotide at the corresponding position in the known nucleic acid sequence. A ligase is provided which covalently connects the two probes when they are correctly base-paired and are located immediately adjacent to each other. The presence, absence or amount of the linked probes is an indication of the presence absence or amount of the known sequence and/or mutation.

Abbot et al. in WO 96/15271 developed a method for a multiplex ligation amplification procedure comprising the hybridisation and ligation of adjacent probes. These probes are provided with an additional length segment, the sequence of which, according to Abbot et al., is unimportant. The deliberate introduction of length differences intends to facilitate the discrimination on the basis of fragment length in gel-based techniques.

WO 97/45559, WO97/31256, WO98/03673, WO00/56929, WO00/56927, WO00/40755 (Barany et al.) describe methods for the detection of nucleic acid sequence differences by using combinations of ligase detection reactions (LDR) and polymerase chain reactions (PCR). Disclosed are methods comprising annealing allele-specific probe pairs to a target sequence and subsequent ligation with a thermostable ligase. Amplification of the ligated products with fluorescently labelled primers results in a fluorescently labelled amplified product. Detection of the products is based on separation by size or electrophoretic mobility or on an addressable array.

Other variants of OLA-based techniques have been disclosed inter alia in Nilsson et al. Human mutation, 2002, 19, 410-415; Science 1994, 265: 2085-2088; U.S. Pat. No. 5,876, 924; WO 98/04745; WO 98/04746; U.S. Pat. No. 6,221,603; WO 03/054511, U.S. Pat. No. 5,521,065, U.S. Pat. No. 5,962, 223, EP185494, EP246864, U.S. Pat. No. 6,027,889, EP745140, EP964704, US20030119004, US2003190646, EP1313880.

Recent publications (Hardenbol et al., Nat. Biotechnology 2003, 21, 673-678; Banér et al., Nucleic Acids Research, 2003, 31, e103) have shown that the OLA principle can be highly multiplexed, making it an attractive technique for high throughput SNP genotyping, especially in combination with sequence-based detection platforms, such as the ones used by the authors of these papers. However, in combination with length-based detection platforms, the high multiplex capacity of the OLA technique is difficult to exploit, due to the limited size distribution of the amplification products obtained from ligated probes that can be detectably separated using current (capillary) sequencing instruments when using ligation probes synthesised by chemical means. This is because the upper limit of currently available chemical oligonucleotide synthesis techniques lies at around 100 to 150 basepairs, which is much less than the size range covered by most (capillary) sequencing instruments. Nevertheless, slab-gels or sequencing instruments are powerful detection platforms due to their ease of use, limited hands-on time and relatively low operating costs compared to most commercially available chip (hybridisation) platforms.

Schouten et al. Nucleic Acids Research, 2003, 30, e57; and EP130113 and WO01/61033 have partially countered this limitation of length-based detection due to the length limitation of chemically synthesised ligation probes by preparing the probes using single stranded phage M13. This ensures high quality probes with a uniform length, capable of spanning the entire length window of a (capillary) sequencing instrument or slab gel system for the detection of amplified ligation probes. However, the probe preparation method of Schouten et al. is cumbersome, time-consuming, difficult to automate and therefore costly and not well suited for applications involving many different target sequences. Hence others solutions are still needed to make efficient use of size-based detection platforms for detection of amplified ligation probes.

Van Eijk et al. (WO03/52140; WO03/52141 WO03/52142, Nucleic acids research, 2004, 32(4), e47) have provided a solution to this problem by selectively amplifying subsets of ligated probes using selective AFLP primers such as those described by Vos et al. for AFLP fingerprinting (Vos et al., *Nucl. Acids Res.*, 1995, 21, 4407-4414; EP534858, U.S. Pat. No. 6,045,994, WO93/06239). Although this approach allows selection of particular subsets of ligated probes for co-amplification in the same reaction with a single primer pair, the composition of the amplifiable subsets is fixed and determined by incorporation of the appropriate binding sites for the AFLP primers in the ligation probes when designing them.

With an increasing demand for high throughput multiplex assays, (i.e. assays that are able to address (detect) a large number of target sequences in one sample and that are able to address many samples in a short period of time), one of the less advantageous aspects of many of the probes that are used in the current oligonucleotide ligation assays is the tendency for probe lengths and the length of the corresponding ligation products to increase.

The current methods are able to provide oligonucleotides through nucleotide coupling reactions with a yield of 98.5% per nucleotide. This means that with an increasing length, for each nucleotide in the probe, the yield of the desired full length probe is lowered and the amount of undesired probes (incomplete synthesis products) increases. As a result, to provide for probes of sufficient length and/or sufficient purity, additional steps are needed to purify the probes prior to use in any assay or alternative methods of synthesis are required.

The increasing length of the products of the ligation of probes presents also a disadvantage, in particular with detection systems based on length, but also in case of mass-based detection or hybridisation based detection due to the increasing possibility of cross-hybridisation.

The present inventors have made it their aim to investigate the oligonucleotide ligation assays and to provide assays that can provide the same amount of information of the same quality, only with probes and/or ligation products of shorter and/or more flexible length. It is one of our aims to modify the assay in which these probes are used and to introduce more flexibility.

DESCRIPTION OF THE INVENTION

In certain embodiments, methods for determining the presence, absence or amount of a target sequence in a nucleic acid sample are provided. In certain embodiments, the method comprises providing to a nucleic acid sample at least one first probe and at least one second probe for each target sequence to be detected in the sample. In certain embodiments, the first probe has a first target specific section that is complementary to a first part of the target sequence. In certain embodiments, the second probe has a second target specific section that is complementary to a second part of the target sequence. In certain embodiments, the first and second parts of the target sequence are located adjacent to each other. In certain embodiments, the second probe comprises a tag section that is essentially not complementary to the target section. In certain embodiments, the tag section comprises a primer binding sequence.

In certain embodiments, the first and second target specific sections of the first and second probe are allowed to anneal to the first and second parts of target sequences. In certain embodiments, the first and second target specific sections of the probes are annealed adjacent on the target sequence.

In certain embodiments, means are provided for connecting the first and second target specific sections annealed adjacently to the target sequence and allowing the first and second target specific sections to be connected, to produce a connected probe corresponding to a target sequence in the sample. In certain embodiments, a compound primer is provided to the mixture comprising the connected probes, which compound primer comprises a section that is complementary to at least part of the first target specific section and further comprises a second primer binding section.

In certain embodiments, the compound primer is allowed to anneal to at least part of the first target specific section. In certain embodiments, the compound primer is elongated. In certain embodiments, a set of primers is provided comprising a first primer having a sequence essentially identical to the first primer-binding sequence, and a second primer that is complementary to the second primer-binding sequence. In certain embodiments, the resulting mixture is amplified to produce an amplified sample comprising amplicons that are representations of the connected probes. In certain embodiments, the presence, absence or amount of a target sequence in a sample is determined by detecting the presence, absence or amount of the corresponding amplicon. The amount can be determined compared to a standard.

The present invention provides for a flexible high throughput, multiplexed method for the detection of the presence, absence or amount of (a) target sequence(s) in a nucleic acid sample. The method comprises contacting the target sequence with a set of at least two probes, a first probe that contains a section that is complementary to a first part of the target sequence and a second probe that contains a section that is complementary to a second part of the target sequence. When the two probes are annealed or hybridised adjacently, they can be ligated to produce connected probes corresponding to a target sequence in the sample. A compound primer is provided that comprises a section that is complementary to at least part of the first target specific section and further comprises a second primer binding site. The compound primer is allowed to hybridise to the part of the first target specific section of the first probe. Upon hybridisation, the compound primer is elongated. The elongated compound primer is amplified using a set of first and second primers complementary to the corresponding first and second primer binding sites. The amplification produces an amplified sample comprising amplicons that are representations of the connected (or ligated) probes. Determination of the presence of a target sequence is by detecting the presence of the corresponding amplicon in the amplified sample.

DETAILED DESCRIPTION OF THE INVENTION

In one preferred embodiment, the invention pertains to a method for determining the presence, absence or amount of a target nucleotide sequence in a nucleic acid sample, the method comprising the steps of:
  a) providing to a nucleic acid sample a first probe (1) for each target sequence (T) to be detected in the sample, whereby the first probe has a first target specific section (4) that is complementary to a first part of the target sequence (5) and a second probe (2) for each target sequence (T) to be detected in the sample, whereby the second probe has a second target specific section (6) that is complementary to a second part of the target sequence (7), whereby the first and second part of the target sequence are located adjacent to each other (3), and whereby the second probe further comprises a tag section (8) that is essentially non-complementary to the target sequence, whereby the tag section comprises a first primer-binding sequence (10);

b) allowing the first and second target specific sections of the first and second probe to anneal to the first and second parts of each target sequence that is present in the sample whereby the first and second target specific sections of the probes are annealed adjacent on the target sequence;

c) providing means for connecting the first and second target specific sections annealed adjacently to the target sequence and allowing the first and second target specific sections to be connected, to produce a connected probe (11) corresponding to a target sequence in the sample;

d) providing to the mixture resulting from step c) a compound primer (12) that comprises a section (15) that is complementary to at least part of the first target specific section and a second primer binding section (14);

e) allowing the compound primer to anneal to at least part of the first target specific section;

f) elongating the compound primer;

g) providing a set of primers comprising a first primer (18) having a sequence essentially identical to the first primer-binding section, and a second primer (17) that is complementary to the second primer-binding section;

h) amplifying the resulting mixture to produce an amplified sample comprising amplicons (19) that are representations of the connected probes;

i) determining the presence, absence or amount of a target sequence in a sample by detecting the presence, absence or amount of the corresponding amplicon.

The present inventors have provided for further flexibility of the composition of amplifiable subsets of ligated probes as it is advantageous to adapt the OLA/ligation-based sequence detection technique to, inter alia, length-based detection platforms, as well as to provide more (or increased) flexibility regarding the combination of ligated probes that are co-amplified, beyond that provided by using ligation probes containing selective nucleotides in combination with selective amplification primers based on AFLP.

The current invention provides this solution by providing a multiplicity of primers with a common 5' tail sequence for the initial round of amplification of ligated probes. These primers are each targeted toward a single target sequence, such as a locus (or allele)-specific sequence in one or more ligation probe(s). This multiplicity of amplification primers is provided together with, preferably a molar excess of, a single amplification primer with a sequence essentially similar to the 5' tail sequence of the multiplicity of primers and, preferably a molar excess of, a common reverse primer, in order to ensure robust co-amplification in the subsequent rounds of amplification by the two primers that preferably are present in the highest molar concentration.

A further advantage of this approach is that the length of the (chemically) synthesised ligation probes is shorter, which allows for higher yield and quality of the ligation probes and/or higher multiplexing levels at the ligation step given the upperlimit in length imposed by the synthesis procedures. This is because a larger number of nucleotides can be allocated to size stuffers when one (or both) primer-binding regions can be omitted from the ligation probe sequence.

Taken together, these advantages ensure the use of multiplexed ligation-based sequence detection in a fully flexible fashion on length-based detection platforms, while still maintaining the advantage of a highly multiplexed ligation reaction as the first step, which ensures the requirement for a low amount of the target nucleic acid/biological samples, even in case the detection of many different sequences or polymorphisms is required.

In step a) of the method, at least one first probe for each target sequence is provided to the nucleic acid sample. The first probe contains a first target specific section. The first target specific section is complementary to a first part of the target sequence. To the nucleic acid sample is further provided at least one second probe for each target sequence to be detected in the sample. The second probe comprises a section that is complementary to a second part of the target sequence. Preferably, the first and second part of the target sequence are located essentially adjacent to each other. The second probe further comprises a tag section that is essentially non-complementary to the target sequence. The tag section comprises a first primer binding section.

In step b), the first and second target specific sections of the first and second probes are allowed to anneal to the respective first and second parts of the target sequence. Annealing (or hybridisation) is performed under suitable conditions for annealing, as exemplified herein elsewhere. Preferably, the first and second target specific sections of the probes are annealed adjacent on the target sequence. In certain specific embodiments, the first and second target specific sections of the probes are not annealed adjacent on the target sequence, as exemplified under gap-ligation.

In step c), means are provided for connecting (or ligating) the first and second target specific sections of the probes when they are annealed adjacently. Means can be chemical ligation means or enzymatic ligation means. Examples of such enzymatic means are enzymes such as ligase, as exemplified hereinbelow. The first and second target specific sections of the probes are allowed to be connected. The connection of the first and second target specific sections of the probes results in a connected probe that corresponds to a target sequence in the sample. The connected probe can be described as "$1^{st}$ target specific section—$2^{nd}$ target specific section-tag section".

In step d) a compound primer is provided. The compound primer comprises a section that is complementary to at least part of the first target specific section. The section may be complementary to the entire first target specific section, or only to a part thereof, such as 50, 60, 70, 80 or 90% of the entire first target specific section (rounded off to the nearest number of whole nucleotides). The section is preferably large enough to selectively hybridise to the corresponding part of the first target specific section of the first probe and not to other oligonucleotides in the sample so as to allow specific elongation of the compound probe along the connected probe. The compound primer further comprises a second primer binding section.

In step e) the compound primer is allowed to anneal to at least part of the first target specific section of the first probe. The compound primer is allowed to anneal under stringency conditions suitable for annealing as described herein elsewhere. Preferably, the compound primer anneals selectively to the first probe and not to other oligonucleotides in the sample, including other target sequences. In certain embodiments, target sequences are removed (enzymatically) to achieve this. Preferably, the duplex of the connected probe and the target sequence is denatured prior to annealing of the compound primer.

In step f) the compound primer is elongated, preferably in the presence of enzymes such as polymerases and preferably in the presence of dNTPs. The compound primer is elongated using the connected probe as a template. The result is an elongated compound primer. The elongated compound primer is a representation of the ligation product (connected probe) and therewith of the target sequence in the sample. The elongated compound primer can be (schematically) described as "$2^{nd}$ primer binding site—$1^{st}$ target specific section—$2^{nd}$ target specific section-tag section". In certain embodiments, the elongated compound primer can be described as "$2^{nd}$ primer binding site—(optional $2^{nd}$ identifier)—$1^{st}$ target specific section—$2^{nd}$ target specific section—(optional $1^{st}$ identifier)—$1^{st}$ primer binding site".

In step g) a set of primers is provided. The set comprises a first primer that is essentially identical to the first primer binding section in the second probe and a second primer capable of annealing to the second primer binding section. The first primer is essentially identical to the first primer binding section. The first primer is capable of annealing to the complement of the first primer binding section such that amplification can be initiated from the complement of the first primer binding section. Both primers are capable of initiating amplification. Primers, as well as selective primers are described herein elsewhere.

In certain embodiments, the compound primer and the primers are provided to the mixture obtained after step c) simultaneously, i.e. at the same time and/or in one step. In such preferred embodiments, the primers are preferably added to the mixture obtained after step c) before elongation of the compound primer, i.e. step g) is preferably performed before step f) and/or steps d) and g) may preferably be combined into a single step that is performed prior to steps e) and f). In certain embodiments, elongation of the compound primer and amplification of the elongated compound primer is combined into a single step. In certain embodiments, the molar ratio of the first, the second or the first and the second primer to the compound primer is between 1 and 100.000. In certain embodiments, the molar ratio is between 2 and 10.000. In certain embodiments, the molar ratio is between 5 and 1000. In certain embodiments, the molar ratio is between 10 and 100.

In certain embodiments, the molar ratio of the compound probe to the first or second probe is between 1 and 1000, preferably between 5 and 500, more preferably between 10 and 100, most preferably between 25 and 50.

In step h), the mixture resulting from step g) is amplified. Preferably, the duplex of the elongated compound primer and the connected probe is denatured prior to the initiation of the amplification. Amplification encompasses a broad range of techniques for amplifying nucleic acid sequences, either linearly or exponentially. Exemplary amplification techniques include, but are not limited to, PCR or any other method employing a primer extension step, and transcription or any other method of generating at least one RNA transcription product. Other non-limiting examples of amplification are ligase detection reaction (LDR), and ligase chain reaction (LCR). Amplification methods may comprise thermal-cycling or may be performed isothermally. The resulting mixture is the amplified sample. The amplified sample comprises amplicons that are the result of the amplification of the elongated compound primer. The amplicons are, via the elongated primer, representations of the connected probe and consequently of the target sequence to be detected.

In step i) the presence or the absence of the target sequence is detected by determining the presence or the absence of the corresponding amplicon. Detection is in principle possible on a wide number of detection platforms, including those based on length (or mobility), mass or sequence (hybridisation based). Detection is based on identifying the presence, absence or amount of a particular amplicon or a portion of an amplicon (i) at a specific address on an addressable support (i.e. location on an (micro)array); (ii) occupying a particular length or mobility address, or (iii) occupying a specific mass address. In certain embodiments, detection may be based on the detection of the presence, absence or amount of a label in the amplicon.

The various aspects of the present invention are discussed in more detail herein below.

Probes

The sections of the oligonucleotide probes that are complementary to the target sequence are designed such that for each target sequence in a sample, a first and a second probe is provided, whereby the probes each contain a section that is complementary to a part of the target sequence and the corresponding complementary parts of the target sequence are located essentially adjacent to each other. In certain embodiments, the combination of a first and a second probe is referred to as a pair of oligonucleotide probes. In certain embodiments, the combination of a pair of probes with one or more compound primers is referred to as a set of probes.

In certain embodiments, within a pair of oligonucleotide probes, the first oligonucleotide probe has a section at its 5'-end that is complementary to a first part of a target sequence and the second oligonucleotide probe has a section at its 3'-end that is complementary to a second part of the target sequence. Thus, when the pair of probes is annealed to complementary parts of a target sequence the 5'-end of the first oligonucleotide probe is essentially adjacent to the 3'-end of the second oligonucleotide probe such that the respective ends of the two probes may be ligated to form a phosphodiester bond or covalently connect in an other suitable fashion. See also FIG. 2.

Thus, in the method of the invention preferably at least a pair of two oligonucleotide probes is used. However, in certain embodiments, in particular in the gap-ligation embodiments the pair of two probes may be complemented with a third or further oligonucleotide probe. This is still considered a pair of probes. In such instances the third or further oligonucleotide probes preferably comprise, or more preferably consist of one or more nucleotide sequences complementary to the target sequences to be detected, such that upon successful hybridisation to the target sequence, together with the first and second oligonucleotide probes, the first, second, third and further probes may be connected or ligated to form a connected probe (see below).

Preferably, a group of multiple sets of probes comprising first and second oligonucleotide probes and compound primers are provided, wherein each pair is complementary to different target sequences in a sample is provided to enable detection of a multiplicity of target sequences. A set of oligonucleotide probes for a given target sequence in a sample will at least differ in nucleotide sequence from probe sets for other target sequences, and will preferably also differ in length from probe sets for other targets, more preferably a probe set for a given target will produce a connected probe and/or amplified connected probe (amplicons, obtained after optional amplification of the connected probes) that differs in length from connected probes corresponding to other targets in the sample as described below. Alternatively, connected probes and/or amplicons corresponding to different targets may have an identical length if they can be otherwise distinguished e.g. by different labels as described below. Alternatively, connected probes and/or amplicons may be distinguished based on sequence or mass rather than length, using hybridisation based methods with (labelled) probes or arrays or mass spectrometry, respectively.

The target specific section in the probes of the present invention each (independently) comprise from about 15 to 35, preferably from 18 to 32, more preferably from 20 to 30 nucleotides.

In certain embodiments, the target specific section contains at least one allele-specific nucleotide, preferably at the 3' end of a target section adjacent to the phosphorylated 5' end of the first probe (FIG. 4). This allows for the detection of a specific SNP or an allele of a locus. When the allele specific nucleotide is present in the target sequence, the two probes will form a matched duplex that can be ligated in to a connected probe. Detection of the connected probe or of the corresponding amplicon is an indication of the presence of that specific allele in the sample.

In one embodiment, the sample may be provided with one or more groups of sets of probes, preferably two or more, more preferably three or more groups of sets of probes. By combining each of the groups with at least one primer that is capable of selectively amplifying only one group from amongst the other groups, a further increase in throughput can be obtained as one ligation assay can be used for the detection of different groups of target sequences. A set of probes may be provided in one step to the sample or each probe in the set may be provided to the sample individually. For a group comprising multiple probe sets, each type of probe (first, second or compound primer) may be added separately.

First Probe

The first probe comprises a target specific section that is complementary to a first part of the target sequence to be detected in the nucleic acid sample. In certain embodiments the first probe contains a tag section that is not complementary to the target sequence. The tag section may aid in intermediate isolation or purification of any ligated products. In certain embodiments, the tag section comprises GC-rich sequences or ZIP sequences. In certain embodiments, the tag section comprises affinity ligands such as biotin. In certain embodiments, the first probe is exonuclease resistant to allow for removal of unligated probes. In certain embodiments, the first probe does not comprise a primer binding sequence. In certain embodiments, the first probe consists of a target specific section that is complementary to a first part of the target sequence to be detected in the nucleic acid sample. In certain embodiments, the first probe is not capable of hybridising to other (target) sequences in the nucleic acid sample.

Second Probe

The second probe comprises a target specific section that is complementary to part of the target sequence. The second probe further comprises a tag section that is essentially non-complementary to the target section. Preferably, the tag section is not capable of hybridising to the target sequence. Preferably, the tag section is also not capable of hybridising to other (target) sequences in the nucleic acid sample.

The tag section comprises a first primer binding site. In certain embodiments an identifier sequence is located between the primer binding site and the target specific section. The presence of the identifier sequence in the connected probes and/or amplicons provides the identification of the presence of the target sequence in the sample. In certain embodiments, the identifier provides a length difference between different sets of probes directed to different target sequences in a sample such that the presence of different target sequences is based on length (or mobility) based detection such as electrophoretic techniques. In certain embodiments, the identifier provides a sequence difference between different probes directed to different target sequences in a sample such that the presence of different target sequences is based on sequence-based detection such as arrays. In certain embodiments, the identifier provides a mass difference between different probes directed to different target sequences in a sample such that the presence of different target sequences is based on mass-based detection such as Maldi-TOF.

In certain embodiments the tag section may comprise recognition sites for restriction endonucleases. The presence of such restriction sites allows to further reduce the size of any amplicon and thus to further increase the throughput capacity of mass-based or length based detection techniques.

Compound Primer

The compound primer comprises a first probe specific section that is complementary to at least part of the target specific section of the first probe. In certain embodiments, the first probe specific section is essentially identical to at least part of the first part of the target sequence. The first probe specific section of the compound primer contains at least 4 or at least 8, preferably at least 10, more preferably at least 12 nucleotides that are complementary to the target specific section of the first probe, in particular at least 15, more preferably at least 18 and most preferred at least 20 nucleotides.

In certain embodiments, the compound primer further comprises a second primer binding section. The second primer binding section is capable of annealing to a second primer under conditions of appropriate stringency.

In certain embodiments, the compound primer further comprises a second identifier sequence. In certain embodiments, the second identifier is the sole identifier sequence. In certain embodiments, the combination of the second identifier and the first identifier serves to uniquely identify the identifier sequence. In certain embodiments, the combination of the second identifier and the first identifier provides the difference in molecular mass, length or sequence that serves to distinguish one amplicon corresponding to one target sequence from another (different) amplicon corresponding to a different (another) target sequence.

In certain embodiments, the compound primer further comprises a second probe specific section that is complementary to at least part of the target specific section of the second probe. In certain embodiments, the first probe specific portion and the second probe specific portion are located adjacent. The compound primer is capable of annealing to the ligated first and second probe thereby spanning the point of ligation. By annealing to the ligated probe spanning the point of ligation, an additional discriminatory step is introduced in that this can only occur if the probes have been ligated. Furthermore, an additional advantage is that the elongated compound primer and the corresponding amplicons are of a shorter length, thereby increasing the flexibility and multiplex capacity of the assay. See FIG. 3A, 3B.

The second probe specific section of the compound primer comprises at least 4 or at least 8, preferably at least 10, more preferably at least 12 nucleotides that are complementary to the target specific section of the first probe, in particular at least 15, more preferably at least 18 and most preferred at least 20 nucleotides.

In certain embodiments, the combined first and second probe specific portions comprises at least 8, preferably at least 10, more preferably at least 20 nucleotides that are complementary to the target specific section of the combined first and second probe, in particular at least 25, more preferably at least 30 and most preferred at least 40 nucleotides.

Semi-Circular Probes

One of the aspects of the invention pertains to a method for the detection of a target nucleotide sequence in a sample, comprising providing at least a pair of a first and a second oligonucleotide probe for each target nucleotide sequence to be detected in the sample, whereby the first oligonucleotide probe has a section at its 5'-end that is complementary to a first part of a target sequence and the second oligonucleotide probe has a section at its 3'-end that is complementary to a second part of the target sequence, and whereby the first oligonucleotide probe further comprises a clamp section that is capable of hybridising to a complementary clamp section located in the second oligonucleotide probe whereby the clamp sections are essentially non-complementary to the target sequence, allowing the oligonucleotide probes to anneal to the target sequence, providing means for connecting the first and the second oligonucleotide probes and allowing first and second oligonucleotide probes to be connected when hybridized to adjacent sections of the target sequence to produce a connected probe corresponding to a target sequence in the sample, providing a compound primer that comprises a section that is complementary to at least part of the first target specific section of the first probe and optionally to at least part of the second target specific section of the second probe and a second primer binding section, allowing the compound primer to anneal to at least part of the first target specific section of the first probe and optionally to at least part of the second target specific section of the second probe, elongating the compound primer, providing a set of primers comprising a first primer having a sequence essentially identical to the first primer-binding section, and a second primer that is complementary to the second primer-binding section, amplifying the resulting mixture to produce an amplified sample comprising amplicons that are representations of the connected probes, determining the presence, absence or amount of a target sequence in a sample by detecting the presence, absence or amount of the corresponding amplicon.

One of the aspects of the invention pertains to a set of probes (K) comprising a first probe (P1) which comprises a first target section (T1) and a first clamp section (C1), and a second probe (P2) which comprises a second target section (T2) and a second clamp section (C2), wherein the first and second clamp sections (C1, C2) are capable of hybridising to each other and a compound primer (see FIG. 6).

In one embodiment, the invention pertains to a set of oligonucleotide probes (K) comprising:

a first oligonucleotide probe (P1) that comprises a first clamp section (C1), that is capable of hybridising to a second clamp section (C2) of a second oligonucleotide probe (P2), and a first target section (T1) that is capable of hybridising to a first section (S1) of a target DNA sequence (D) to be detected;

a second oligonucleotide probe (P2) that comprises a second clamp section (C2), that is capable of hybridising to the first clamp section (C1) of the first oligonucleotide probe (P1), and a second target section (T2) that is capable of hybridising to a second section (S2) of the target DNA sequence (D) to be detected a third oligonucleotide compound primer that comprises a section that is complementary to at least part of the first target specific section and a second primer binding section.

When the set of probes is brought into contact, under hybridising conditions, with a sample comprising a target sequence, the two target sections T1 and T2 of the probes will hybridise to the first S1 and second S2 sections of the target DNA sequence.

The clamp sections C1 and C2 are designed such that under the conditions under which T1 and T2 hybridise to the target DNA sequence, C1 and C2 are also hybridised to each other, forming a clamp. The configuration of the hybridised probes now resembles a padlock probe (in terms of target specific hybridisation characteristics) with a clamp. After ligation, the compound primer can anneal to the ligated or connected probe and elongated along the connected probe as described herein elsewhere. The elongated probe can be amplified as described herein elsewhere.

In addition to the advantages of the invention mentioned herein elsewhere, the probes of the present invention have the advantageous hybridisation characteristics of padlock (circularizable) probes in terms of the favourable hybridisation kinetics, but have also the advantageous characteristics of linear hybridisation probes in terms of absence of concatemer formation during the elongation or amplification step. Hence the probes of the present invention combine the advantages of the different probe types. The probes of the present invention have a length that remains within the realms of what can be reliably synthesised using conventional chemical synthesis or other techniques, which is a significant economical advantage. A further advantage is that the probes of the present invention can be of a better quality (i.e. purity) thereby obviating additional purification of the probes, compared to (longer) padlock probes which is connected with the technical advantage that such probes are capable of significantly reducing the signal to noise ratio. Thus, the probes of the present invention combine the advantageous characteristics of circularizable/padlock probes with the advantageous synthesis and purity/quality of linear oligonucleotides of relative short length.

The method of the present invention for the detection of target sequences thus profits from the advantages of both the linear and padlock probes while avoiding the cumbersome synthesis of long oligonucleotides (padlock probes) and the unfavourable hybridisation kinetics of a pair of unlinked linear probes in the hybridisation to the target sections of the target sequence to be detected.

The pair of oligonucleotide probes are designed such that for each target sequence in a sample, a pair comprising a first (P1) and a second probe (P2) is provided, whereby the probes each contain a section (T1,T2) at one of their extreme ends that is complementary to a part of the target sequence (S1, S2). Preferably the complementary parts (S1, S2) of the target sequence are located essentially adjacent to each other. However, in certain embodiments of the invention the ends of the complementary parts (S1, S2) in the probes are not located adjacently to each other on the target sequence. Such embodiments include e.g. the embodiments described herein elsewhere under gap-ligation.

Within a pair of oligonucleotide probes, the first oligonucleotide probe has a section T1 at its (phosphorylated) 5'-end that is complementary to a first part S1 of a target sequence and the second oligonucleotide probe in the pair has a section T2 at its (hydroxylated) 3'-end that is complementary to a second part S2 of the target sequence. Thus, when the pair of probes is annealed to complementary parts (S1, S2) of a target sequence the 5'-end of the first oligonucleotide probe is preferably essentially adjacent to the 3'-end of the second oligonucleotide probe such that the respective ends of the two probes may be ligated to form a phosphodiester bond or another covalent bond in any suitable fashion to provide a "connected probe".

For each target sequence for which the presence, absence or amount in a sample is to be determined, a specific pair of first and second oligonucleotide probes is designed with sections complementary to the complementary parts of each target sequence as described above. Thus, in the method of the invention, for each target sequence that is present in a sample, a corresponding (specific) connected probe may be obtained.

Clamp

The clamp section is preferably located at or near the end of the probe that is distal to the target section, i.e. when the target section is located at the 3' end, the clamp section is located more towards the 5' end and vice versa. The clamp section is not necessarily located most distal at the 5' end or 3' end, it may be followed by other sections discussed herein elsewhere. The clamp sections are preferably designed such that they are not capable of hybridising to the target sections. The clamp sections of the first and second probe of the pair are capable of hybridising to each other. The clamp sections are preferably designed such that two complementary clamp sections have a higher binding affinity for each other than the binding affinity of the target section of the probe for its complementary part in the target nucleotide sequence. This means in practice that the clamp sections, when hybridised to each other, form a stronger duplex than the hybrid between the target section and its complement in the target nucleotide sequence and/or hybridization of complementary clamps takes place at higher temperatures than hybridisation of the target complementary section of the probes to the target. In other words, the hybridised clamp section denatures, under otherwise comparable conditions, at a higher temperature or higher stringency conditions than the denaturation temperature of the target complementary sections in the pair of probes. This allows to choose the conditions during the method of the invention such that the hybridised or locked clamp remains hybridised or closed at least until the probes are connected to produce a connected probe. The locked clamp can be opened by denaturing the (connected) probe at a temperature or under circumstances that allow the denaturation of the locked clamp.

A pair of probes having locked clamps expresses similar or identical hybridisation kinetics and behaviour as do circular or padlock probes. The two probes of a pair can be added separately after which the clamp sections are hybridised to each other in the sample or, alternatively the two probes can be locked prior to being added to the sample.

In a preferred embodiment the clamp has a denaturation temperature (or melting temperature, Tm) that exceeds the denaturation temperature of the target complementary sections in the pair of probes by at least 1° C., preferably 5° C. more preferably 10° C. compared to the lowest Tm of the T1 or T2 section. The denaturation temperature of a oligonucleotide sequence can calculated/estimated from the nucleotide composition using the general formula's for Tm=(4*G or C)+(2*A or T) or Tm=(4*G/C)+2*A/T)−5° C. (Meinkoth et al. Anal. Biochem. (1984) 138: 267-284). Other formulas are likewise applicable as the essence lies in the difference in denaturation temperature between the sections (Tm[clamp]−Tm[target]). This can be achieved not only by varying the length of the clamp sections but also by varying the GC content of the clamp, as a GC basepair increases Tm by about 2° C. compared to an AT basepair. A typical clamp section comprises 10 to 30, preferably 15 to 25 and more preferably 18 to 24 nucleotides. When the GC content is lower, this number of nucleotides may increase as long as the desired hybridisation characteristics are obtained. Alternatively modified nucleotides can be used that increase the hybridisation between the two clamp sections. Examples thereof are nucleotides that have improved hybridisation characteristics, such as Locked Nucleic Acids such as disclosed in WO 99/14226, WO 00/56748, WO 00/66604 and WO 01/25478, Peptide Nucleic Acids or by other molecules that stabilise or enhance DNA hybridisation such as minor groove binders and others, such as those in described in EP 0 974 672.

The GC content of the clamp may vary, wherein the GC content of clamp section ranges from more than 50 to 100%, preferably more than 60%, more preferably more than 70%, most preferably more than 80% and is preferably in the range of 90-100%. Hence most clamp sections will contain A/T combinations on a more incidental or structural basis. A preferred group of clamp sections are GC enriched ZIP sequences (Iannone et al. (2000), Cytometry 39: pp. 131-140). Preferably the clamp section comprises at least one, preferably at least 2, 3, 4, or 5 nucleotides selected from the group consisting of G's and C's, more than each of T1 and T2.

In a preferred embodiment, when groups of pairs are involved, a different clamp section may be provided for each pair of probes in the group. The clamp section is designed such that a clamp for a first pair of probes and clamps for a second or further pair of probes are distinguishable from each other and preferably do not cross hybridise to each other under conditions used in the ligation assay. Each pair of probes comprises a unique clamp, thereby avoiding cross hybridisation between clamps of different pairs of probes in a sample. To this end the clamp section may comprise additional nucleotides or the oligonucleotide sequences of the clamp section can be unique within the group. The use of unique clamp sections for each pair of probes in a group enables the detection of multiple target sequences in one sample simultaneously. This embodiment also enables the detection of one or more different target sequences in multiple samples subsequently, using the same collection of pairs of probes. This embodiment further enables that the same group of pairs of probes can be used over and over again for the detection of different target sequences.

Preferably, when using different clamps in a group of pairs of probes, these clamps have a Tm that is within a small range, preferably between about 60-90° C., more preferably between 65-88° C., most preferably between 70-85° C. As is known the hybridisation characteristics of nucleic acids are also influenced by the salt concentrations. As used herein, comparison of hybridisation characteristics in general or denaturation temperatures in particular of oligonucleotides is considered under comparable salt concentrations, unless indicated otherwise.

Alternative clamps that can be used in the present invention are nucleic acids that contain photodegradable links. After ligation, the photodegradable link can be removed and the connected probe amplified and/or detected.

After ligation of the first and second probe, the clamp may optionally be denatured. A compound primer as described herein elsewhere can be provided and allowed to anneal to the connected probe. Elongation of the compound primer will provide an elongated compound primer which can be amplified, as described herein elsewhere. See also FIG. 6. In certain embodiments, only one of the first and second probe contains a first primer binding site. In certain embodiment, the compound primer contains a second primer binding site, essentially as described herein elsewhere.

Cleavase Ligation

In one aspect of the present invention, an additional discriminating step can be introduced prior to ligation. In certain embodiments, the first or the second oligonucleotide probe of the pair is designed such that one of the two probes is extended beyond the foreseen point of ligation of its target-specific section. Preferably the probe is extended with a sequence that is not complementary to the target sequence. In the event of correct annealing of target-specific sections of the two probes to the target sequence, a forked cleavage structure is formed wherein the 3'-end of the target-specific section of the non-extended probe is annealed to the target sequence, while the extended 5' end of the other probe, which is non-complementary to the target sequence, forms a single-stranded arm (see FIG. 7A). The thus-obtained forked cleavage structure is a substrate for the 5' nuclease activity of DNA polymerases, referred to herein as a cleaving agent, or cleavase. A preferred cleavase is a modified DNA polymerase having 5' nuclease activity but lacking synthetic activity or a FEN endonuclease. An example of such a forked cleavage structure and such a cleavase is described in EP 601834 and U.S. Pat. No. 5,795,763 (Third Wave Technologies).

In certain embodiments, the cleavase may be a native DNA polymerase but preferably the cleavase is a modified form that lacks the synthetic activity of the DNA polymerase. Suitable DNA polymerases with 5' nuclease activity and that may be modified to inactivate their synthetic activity are polymerases from e.g. *Thermus thermophilus, Thermus aquaticus, Escherichia coli*, and *Thermus flavus*, or a modified form of the gene 6 product from bacteriophage T7 or FEN endonuclease. Other suitable cleavases are mentioned inter alia in U.S. Pat. No. 6,635,463, U.S. Pat. No. 6,562,611, U.S. Pat. No. 6,555,357, U.S. Pat. No. 6,458,535, U.S. Pat. No. 6,348,314, U.S. Pat. No. 6,090,606, U.S. Pat. No. 6,090,543, U.S. Pat. No. 6,001,567, U.S. Pat. No. 5,994,069, U.S. Pat. No. 5,985,557, U.S. Pat. No. 5,843,669,U.S. Pat. No. 5,846,717, U.S. Pat. No. 5,837,450, U.S. Pat. No. 5,614,402, WO94/29482, WO97/27214, WO98/23774, WO98/42873.

Upon incubation of the forked cleavage structure with a suitable cleavase, cleavage will occur in the extended probe, right between the first unmatched nucleotide of the extension sequence and the first matched nucleotide of the target-specific section of the extended probe. The extension sequence is thus removed and the two ends of the target-specific sections of the first and second probes of the pair will anneal immediately adjacent to each other, in case of a perfect match with the target sequence, thus allowing for ligation of the two probes to form a connected probe (see FIG. 7A). This principle is valid for and can be applied to any conventional OLA assay and the assays of the present invention alike and is an inventive improvement of the OLA-technology by further improving the fidelity of the OLA-technology. The principle is valid for non-circularizable, circularizable and semi-circularizable probes as well as the combination of a first, a second and a compound primer as described herein alike.

In certain embodiments, the method comprises a step wherein a cleavage structure is formed comprising the target nucleic acid sequence, a first probe and a second probe. In certain embodiments, the first probe comprises a first target specific region that is capable of annealing to a first section of the target nucleic acid sequence to form a first duplex. In certain embodiments, the second probe comprises a second target specific region that is capable of annealing to a second section of the target nucleic acid sequence to form a second duplex. In certain embodiments, the first and second sections of the target nucleic acid sequence are contiguous so that the first and the second duplexes are contiguous. In certain embodiments, the first probe or the second probe comprises a further region (E, see FIGS. 7A and 8), an extended region, preferably an extended 5'-end, that is not capable of annealing to the target nucleic acid sequence. In certain embodiments, the further (extended) region is located at the end of the first or second probe at the position of the junction site (i.e. the potential site of ligation of the OLA-assay) between the first and second sections of the target nucleic acid sequence. In certain embodiments, the further (extended) region provides a non annealed section of the first or the second probe to thereby create a (forked) cleavage structure. Certain embodiments comprise exposing the cleavage structure to a cleavage agent that preferably cleaves the cleavage structure in a manner independent of the sequence of the cleavage structure and results in cleavage of the cleavage structure when the cleavage structure and cleavage agent are incubated under conditions wherein cleavage can occur. In certain embodiments, cleaving the cleavage structure results in removal of the further (extended) region. In certain embodiments, the removal of the further (extended) region by cleaving the cleavage structure results in adjacent localization of the first and second probe.

In one aspect, the invention relates to the use of a cleavage agent, preferably prior to ligation, in OLA-assays. In certain embodiments, the cleavage agent is used to remove an overhang (i.e. the further or extended region) of the first or second probe located at the envisaged point of ligation such that the first and second probe can be ligated. The characteristics of the cleaving agent are that cleavage occurs when the two probes are annealed adjacent to each other on the target sequence and one of the probes has an overhang at the point where the probes are annealed adjacent. In certain embodiments, cleavage occurs only when the two probes are annealed adjacent to each other on the target sequence and one of the probes has an overhang at the point where the probes are annealed adjacent. The cleavage of the overhang provides two probes that are annealed adjacent on the target sequence and that can be ligated. One of the technical advantages of this cleavage step is that the cleavage step provides the 5' phosphate at the end of one of the probes necessary for ligation. The provision of the 5'phosphate can be used as an alternative for conventional oligonucleotide synthesis wherein phosphorylation at the 5' end is one of the final steps in the synthesis of oligonucleotides. A further technical advantage is that the selectivity and specificity of the subsequent ligation reaction is significantly increased due to the improved selectivity of the cleavage agent to cleave only cleavage structures, i.e. those structures where the nucleotide in the overhang is complementary or capable of hybridizing to the nucleotide in the target sequence.

In certain embodiments directed to the allele specific detection of SNPs in target sequences, the allele specific nucleotide is incorporated in the probe that contains the further (extended) region. Thus, one probe of the pair comprises target specific section that anneals essentially adjacent to the SNP to be investigated. The other probe of the pair comprises a target specific section that contains the nucleotide that is complementary to the SNP to be investigated and, adjacent to that nucleotide, the further (extended) region. A generalized representation of this embodiment, applicable to all OLA-assay's and the present invention alike involves the use of a further (extended) region is in FIGS. 7A, 7B and 8. This embodiment allows both the cleavage step and the ligation step to occur only in case both target sections are a perfect match at the point of ligation/cleavage and this embodiment further improves specificity.

The introduction of the cleavage step in the OLA assay combines the specificity of the monoplex Invader Assay (Third Wave Technologies) with the flexible multiplex capacity of OLA SNPWave assays. This allows for instance to measure SNP frequencies in pooled or complex samples or other forms of quantitative measurement of sequences such as non-routine transcript profiling, or quantitative measurement of contamination levels of pathogens in soil, food, waters etc.

The use of this additional step in OLA assays provides significant advantages and finds application in, for instance, in the field of quantitative analysis of allele frequencies in, for instance, population screenings or in the field of identification of low-frequent mutants in complex samples.

It will be clear to the man in the art that based on the teaching of the various embodiments herein described that several combinations of embodiments can be made. For instance in certain embodiments, in a set of semi-circular probes with clamp sections of the type herein described, one of the two probes can be extended beyond the foreseen point of ligation of its target-specific section, thus mimicking padlock behaviour with the additional discrimination step of the cleavage step as described herein elsewhere.

Identifiers

In certain embodiments, the second oligonucleotide probe of the present invention further comprises an identifier sequence. The identifier sequence is of a variable length, sequence or mass. In certain embodiments, the compound primer also contains an identifier. The length of the identifier (or of the combined identifiers in the second and the compound primer) varies from 0 to 1000, preferably from 0 to 500, more preferably from 1 to 100 and most preferred from 1 to 50 nucleotides. The identifier may be a unique sequence as is known as a ZIP-coded sequence as described by Iannone et al. (2000), Cytometry 39: pp. 131-140. The identifier may be located between the second target section and the first primer binding sequence. The identifier may be used to impart length differences between probes or connected probes but can also be used to impart mass differences for mass-based detection or addressable sequences (ZIPs and cZIPs) for hybridisation based detection. Preferably, for each target sequence in the sample, the corresponding connected probe and/or amplicon is provided with an unique identifier sequence. As indicated above, the identifier sequence may be unique in that it provides the connected probe and/or amplicon it identifies with an unique length, sequence and/or mass.

Primer Binding Sites

To facilitate amplification of the elongated compound primers, primer binding sites may be incorporated in the compound primer and in the second probe. Primer binding sites are preferably located in other parts of the compound primer and the second probe than the respective target sections, preferably in the tag section which is essentially non-complementary to the target sequence. Primer binding sites are capable of binding primers to initiate primer elongation or amplification. Preferably within a group of sets of probes, the primer binding sites are universal, i.e. only a predetermined group of primer binding sites are incorporated in the probe to enable multiplex primer elongation or amplification from a limited number of primers, such as primers comprising one or more selective bases at their 3' end, such as are known from AFLP (EP 0 534 858). Between groups of sets of probes, primer binding sites may be different. In certain embodiments, the Tm of primers capable of binding to the different primer binding sites may be different between groups of sets of probes.

The function of identifier and primer binding sites in a probe can be combined and can be interrelated in the sense that a specific part of the probe may function as (part of) a primer binding site for primer elongation/amplification, and at the same or another time as (part of) an identifier to impart the desired and detection platform-based difference such as disclosed herein elsewhere.

Hybridisation

Beginning with step (a) of the method, a multiplicity of different target sequences, i.e. at least two different target sequences, is brought into contact with a multiplicity of specific oligonucleotide probe pairs under hybridising conditions. The pairs of oligonucleotide probes are subsequently allowed to anneal to the, preferably adjacent, complementary parts of the multiple target sequences in the sample. Methods and conditions for specific annealing of oligonucleotide probes to complementary target sequences are well known in the art (see e.g. in Sambrook and Russell (2001) "Molecular Cloning: A Laboratory Manual ($3^{rd}$ edition), Cold Spring Harbor Laboratory, Cold Spring Harbor Laboratory Press).

Usually, after mixing of the oligonucleotide probes and target sequences the nucleic acids are denatured by incubation (generally at between 94° C. and 96° C.) for a short period of time (e.g. 30 seconds to 5 minutes) in a salt buffer. The sample containing the denatured probes and target sequences is then allowed to cool to an optimal hybridisation temperature for specific annealing of the probes and target sequences, which usually is about 5° C. below the melting temperature of the hybrid between the complementary section (target section) of the probe and its complementary sequence (in the target sequence). In order to prevent aspecific or inefficient hybridisation of one of the two probes of a pair, or in a sample with multiple target sequences, it is preferred that, within one sample, the sections of the probes that are complementary to the target sequences are of a similar, preferably identical melting temperatures between the different target sequences present in the sample. Thus, the complementary sections of the first and second probes preferably differ less than 20, 15, 10, 5, or 2° C. in melting temperature. This is facilitated by using complementary sections of the first and second probes with a similar length and similar G/C content, the complementary sections preferably differ less than 20, 15, 10, 5, or 2 nucleotides in length and their G/C contents differ by less than 30, 20, 15, 10, or 5%. Complementary as used herein means that a first nucleotide sequence is capable of specifically hybridising to second nucleotide sequence under normal stringency conditions. A nucleotide sequence that is considered complementary to another nucleotide sequence may contain a minor amount, i.e. preferably less than 20, 15, 10, 5 or 2%, of mismatches. Alternatively, it may be necessary to compensate for mismatches e.g. by incorporation of so-called universal nucleotides, such as for instance described in EP-A 974 672, incorporated herein by reference or with LNAs or PNAs. Since annealing of probes to target sequences is concentration dependent, annealing is preferably performed in a small volume, i.e. less than 25 µl, preferably less than 10 µl. Under these hybridisation conditions, annealing of probes to target sequences usually is fast and does not to proceed for more than 5, 10 or 15 minutes, although longer annealing time may be used as long as the hybridisation temperature is maintained to avoid aspecific annealing. Longer annealing times are more important/required for quantitative applications which rely on complete target occupation by ligation probes in order to allow monitoring or relative amounts of target sequences between samples.

In a preferred embodiment of the invention, excellent results have been obtained by prolonged hybridisation times such as overnight hybridisation or longer, such as 10 cycles of 1 hour). Prolonged hybridisation times can be advantageous in these assays as the difference in signal due to different hybridisation efficiencies is reduced and it is considered desirable to achieve complete hybridisation and ligation of all probes for which a target sequence is present. Excellent results have been obtained by a combined hybridisation-ligation step using a thermostable ligase described herein. In this embodiment the hybridisation-ligation was performed by allowing the probes to hybridise during 1 hour in the presence of a thermostable ligase, followed by a denaturation step. Repeating these steps for at least 2 times provided good results. Repeating these steps 10 times provided excellent results.

To avoid evaporation during denaturation and annealing, the walls and lids of the reaction chambers (i.e. tubes or microtitre wells) may also be heated to the same temperature as the reaction mixture which is commonly achieved by the use of commercial DNA amplification equipment. In preferred oligonucleotide probes the length of the target-complementary section is preferably at least 15, 18 or 20 nucleotides and preferably not more than 30, 40, or 50 nucleotides and the probes preferably have a melting temperature from the target section of at least 50° C., 55° C. or 60° C.

Hybridisation of the compound primer after ligation of the pair of probes may be performed under identical conditions as disclosed herein for the pair of oligonucleotide probes.

In certain embodiments, the pair of probes and the compound primer are provided simultaneously to the sample. In certain embodiments the compound primer is provided to the sample after annealing of the pair of probes, but prior to ligation of the adjacently annealed probes. In certain embodiments the compound primer is provided after ligation of the adjacently annealed probes but prior to providing the amplification primers to the sample. In certain preferred embodiments, the compound primer is added simultaneously with the amplification primers.

Non-Hybridised Probes

The probes that are not complementary to a part of the target sequence or that contain too many mismatches will not or only to a reduced extent hybridise to the target sequence when the sample is subjected to hybridisation conditions. Accordingly ligation is less likely to occur. The number of spurious ligation products from these probes in general will therefore not be sufficient and much smaller than the bona fide ligation products such that they are outcompeted during subsequent multiplex amplification. Consequently, they will not be detected or only to a minor extent.

A preferred method of the invention further comprises a step for the removal of oligonucleotide probes that are not annealed to target sequences and/or that are not-connected/ligated and/or the target sequences themselves. Removal of such probes is carried out preferably prior to compound primer elongation and/or amplification, and preferably by digestion with exonucleases.

By removal/elimination of the oligonucleotide probes that are not connected/ligated a significant reduction of ligation independent (incorrect) target amplification can be achieved, resulting in an increased signal-to-noise ratio. One solution to eliminate one or more of the not-connected/ligated components without removing the information content of the connected probes is to use exonuclease to digest not-connected/ligated oligonucleotide probes. By blocking the end that is not ligated, for example the 3' end of the downstream oligonucleotide probe (the first probe that, in certain embodiments, does not contain a primer binding site), one probe can be made substantially resistant to digestion, while the other is sensitive. Only the presence of full length ligation product sequence will then prevent digestion of the connected probe. Blocking groups include use of a thiophosphate group and/or use of 2-O-methyl ribose sugar groups in the backbone. Exonucleases include ExoI (3'-5'), Exo III (3'-5), and Exo IV (both 5'-3' and 3'-5'), the later requiring blocking on both sides. Examples of such probes are in table 2A of the examples.

An alternative method for the separation of ligated from unligated probes is by Hybridisation-based pullout (HBP). HBP comprises a process wherein a nucleotide sequence complementary to at least a portion of one probe, for example, the primer-specific portion, is bound or immobilised to a solid or particulate pullout support (see, e.g., U.S. patent 60/124, 092). The ligation reaction mixture (comprising the ligation product, target sequences, and unligated probes) is exposed to the pullout support. The ligation product, under appropriate conditions, hybridises with the support-bound sequences. The unbound components of the ligation reaction mixture are removed, purifying the ligation products from those ligation reaction mixture components that do not contain sequences complementary to the sequence on the pullout support. One subsequently removes the purified ligation products from the support and combines it with at least one primer set to form a first amplification reaction mixture. The skilled artisan will appreciate that additional cycles of HBP using different complementary sequences on the pullout support will remove all or substantially all of the unligated probes, further purifying the ligation product.

In certain embodiments, for the separation of the ligated from the unligated probes, one of the probes, preferably the first probe, is biotinylated. After ligation, the remaining first probes and the ligated probes are isolated from the sample using strept (avidin) or a similar affinity ligand/binding complex combination. The unligated (second) probes remain in the sample. The isolated probes can be subjected to the subsequent steps of the method, inter alia compound primer annealing, elongation, primer annealing, amplification and detection.

Ligation

The respective 5'-phosphorylated and 3'-hydroxylated ends of a pair of first and second oligonucleotide probes that are annealed essentially adjacent to the complementary parts of a target sequence are connected in step (c) to form a covalent bond by any suitable means known in the art. The ends of the probes may be enzymatically connected into a phosphodiester bond by a ligase, preferably a DNA ligase. DNA ligases are enzymes capable of catalysing the formation of a phosphodiester bond between (the ends of) two polynucleotide strands bound at adjacent sites on a complementary strand. DNA ligases usually require ATP (EC 6.5.1.1) or NAD (EC 6.5.1.2) as a cofactor to seal nicks in double stranded DNA. Suitable DNA ligase for use in the present invention are T4 DNA ligase, *E. coli* DNA ligase or preferably a thermostable ligase like e.g. *Thermus aquaticus* (Taq) ligase, *Thermus thermophilus* DNA ligase, or *Pyrococcus* DNA ligase. Alternatively, chemical ligation of suitably modified polynucleotide ends may be used to ligate two oligonucleotide probes annealed at adjacent sites on the complementary parts of a target sequence. Exemplary reactive groups on modified polynucleotide ends include, but are not limited to, phosphorothioate and to sylate or iodide, esters and hydrazide, RC(O)S, haloalkyl, RCH2S and [alpha]-haloacyl, thiophosphoryl and bromoacetamide groups, and S-pivaloyloxymethyl-4-thiothymidine.

Chemical ligation agents include, without limitation, activating, condensing, and reducing agents, such as carbodiimide, cyanogen bromide (BrCN), N-cyanoimidazole, imidazole, 1-methylimidazole/carbodiimide/cystamine, dithiothreitol (DTT) and ultraviolet light. Autoligation, i.e., spontaneous ligation in the absence of a ligating agent, is also within the scope of the invention. Detailed protocols for chemical ligation methods and descriptions of appropriate reactive groups can be found, among other places, in Xu et al., Nucleic Acid Res., 27:875-81 (1999); Gryaznov and Letsinger, Nucleic Acid Res. 21:1403-08 (1993); Gryaznov et al., Nucleic Acid Res. 22:2366-69 (1994); Kanaya and Yanagawa, Biochemistry 25:7423-30 (1986); Luebke and Dervan, Nucleic Acids Res. 20:3005-09 (1992); Sievers and von Kiedrowsli, Nature 369:221-24 (1994); Liu and Taylor, Nucleic Acids Res. 26:3300-04 (1999); Wang and Kool, Nucleic Acids Res. 22:2326-33 (1994); Purmal et al., Nucleic Acids Res. 20:3713-19 (1992); Ashley and Kushlan, Biochemistry 30:2927-33 (1991); Chu and Orgel, Nucleic Acids Res. 16:3671-91 (1988); Sokolova et al., FEBS Letters 232:153-55 (1988); Naylor and Gilham, Biochemistry 5:2722-28 (1966); and U.S. Pat. No. 5,476,930. Both chemical and enzymatic ligation occur much more efficient on perfectly matched probe-target sequence complexes compared to complexes in which one or both of the probes form a mismatch with the target sequence at, or close to the ligation site (Wu and Wallace, 1989, Gene 76: 245-254; Xu and Kool, supra). In order to increase the ligation specificity, i.e. the relative ligation efficiencies of perfectly matched oligonucleotides compared to mismatched oligonucleotides, the ligation is preferably performed at elevated temperatures. Thus, in a preferred embodiment of the invention, a DNA ligase is employed that remains active at 50-65° C. for prolonged times, but which is easily inactivated at higher temperatures, e.g. used in the denaturation step during a PCR, usually 90-100° C. One such DNA ligase is a NAD requiring DNA ligase from a Gram-positive bacterium (strain MRCH 065) as known from WO 01/61033. This ligase is referred to as "Ligase 65" and is commercially available from MRC Holland, Amsterdam.

Gap Ligation

In an alternative embodiment, for instance directed to the identification of indels, the respective ends of the complementary sections of the first and second probe may be annealed such that a gap of one or more nucleotides is left. This gap can be filled with a suitable (third) oligonucleotide and ligated. Such methods are known in the art as 'gap ligation' and are disclosed inter alia in WO 00/77260; U.S. Pat. No. 5,185,243; EP439182; EP320308; WO90/01069. Another possibility to fill this gap is by extension of one end of the probe using a polymerase and a ligase in combination with single nucleotides, optionally preselected from A, T, C, or G, or di-, tri- or other small oligonucleotides. In case the target sequence is RNA, yet another possibility to fill the gap is by extension of one end of the probe using reverse transcriptase and a ligase in combination with single nucleotides, optionally preselected from A, T, C, or G, or di-, tri- or other small oligonucleotides.

Gap ligation may find application in the detection multiple SNPs (haplotyping) that are closely located. In this embodiment, the first oligonucleotide probe is provided with a first allele specific nucleotide for the first SNP and the second oligonucleotide probe with a second allele specific nucleotide for the second SNP. The third probe spans the gap between the first and second probe. After ligation of the three probes to form the connected probe, the compound primer is allowed to anneal to the first probe-derived part of the connected three probes. By directing the compound primer to cover the first allele specific nucleotide of the first SNP and by providing for each allele of the first SNP a different compound primer with different identifiers, an by providing different second probes having different identifiers for each allele of the second SNP, the combination of alleles can be determined at both SNP positions at the same time. The presence of the combination of SNPs can bet detected by the presence of the identifiers present in both the first and the second oligonucleotide probe.

Target Sequences

In its widest definition, the target sequence may be any nucleotide sequence of interest. The target sequence can be any sequence of which its determination/detection is desired, for instance because it is indicative, associated or representative of a certain ailment or genetic make up or disorder. The target sequence preferably is a nucleotide sequence that contains, represents or is associated with a polymorphism. The term polymorphism herein refers to the occurrence of two or more genetically determined alternative sequences or alleles in a population. A polymorphic marker or site is the locus at which sequence divergence occurs. Preferred markers have at least two alleles, each occurring at frequency of greater than 1%, and more preferably greater than 10% or 20% of a selected population. A polymorphic locus may be as small as one base pair. Polymorphic markers include restriction fragment length polymorphisms, variable number of tandem repeats (VNTR's), hypervariable regions, minisatellites, dinucleotide repeats, trinucleotide repeats, tetranucleotide repeats, simple sequence repeats, and insertion elements such as Alu. The first identified allelic form is arbitrarily designated as the reference form and other allelic forms are designated as alternative or variant alleles. The allelic form occurring most frequently in a selected population is sometimes referred to as the wild type form. Diploid organisms may be homozygous or heterozygous for allelic forms. A diallelic polymorphism has two forms. A triallelic polymorphism has three forms. A single nucleotide polymorphism occurs at a polymorphic site occupied by a single nucleotide, which is the site of variation between allelic sequences. The site is usually preceded by and followed by highly conserved sequences of the allele (e.g., sequences that vary in less than $1/100$ or $1/1000$ members of the populations). A single nucleotide polymorphism usually arises due to substitution of one nucleotide for another at the polymorphic site. Single nucleotide polymorphisms can also arise from a deletion of a nucleotide or an insertion of a nucleotide relative to a reference allele. Other polymorphisms include (small) deletions or insertions of several nucleotides, referred to as indels. A preferred target sequence is a target sequence that is associated with an AFLP® marker, i.e. a polymorphism that is detectable with AFLP®.

DNA

In the nucleic acid sample, the nucleic acids comprising the target may be any nucleic acid of interest. Even though the nucleic acids in the sample will usually be in the form of DNA, the nucleotide sequence information contained in the sample may be from any source of nucleic acids, including e.g. RNA, polyA$^+$ RNA, cDNA, genomic DNA, organellar DNA such as mitochondrial or chloroplast DNA, synthetic nucleic acids, DNA libraries, clone banks or any selection or combinations thereof. The DNA in the nucleic acid sample may be double stranded, single stranded, and double stranded DNA denatured into single stranded DNA. Denaturation of double stranded sequences yields two single stranded fragments one or both of which can be analysed by probes specific for the respective strands. Preferred nucleic acid samples comprise target sequences on cDNA, genomic DNA, restriction fragments, adapter-ligated restriction fragments, amplified adapter-ligated restriction fragments. AFLP fragments or fragments obtained in an AFLP-template preamplification.

Samples

It is preferred that a sample contains two or more different target sequences, i.e. two or more refers to the identity rather than the quantity of the target sequences in the sample. In particular, the sample comprises at least two different target sequences, in particular at least 10, preferably at least 25, more preferably at least 50, more in particular at least 100, preferably at least 250, more preferably at least 500 and most preferably at least 1000 additional target sequences. In practice, the number of target sequences in a sample that can be analysed is limited, among others, by the number of amplicons than can be detected. E.g., too many different sets of first and second oligonucleotide probes in a sample may corrupt the reliability of a multiplex amplification step.

A further limitation is formed e.g. by the number of fragments in a sample that can be resolved by the detection platform used. The number can also be limited by the genome size of the organism or the transcriptome complexity of a particular cell type from which the DNA or cDNA sample, respectively, is derived.

Primers

The elongated compound primer is amplified using a set of primers corresponding the primer-binding sites. Preferably, the set comprises a first primer having a sequence essentially identical to the first primer-binding section, and a second primer that is complementary to the second primer-binding section. In a preferred embodiment at least one of the primers or the same set of primers is used for the amplification of two or more different elongated compound primers in a sample, preferably for the amplification of all elongated compound primers in a sample. Such a primer is sometimes referred to as a universal primer as these primers are capable of priming the amplification of all elongated compound primers containing the corresponding universal primer binding site and consequently of all ligated probes containing the universal primer binding site. The different primers that are used in the amplification in step (h) are preferably essentially equal in annealing and priming efficiency. Thus, the primers in a sample preferably differ less than 20, 15, 10, 5, or 2° C. in melting temperature. This can be achieved as outlined above for the complementary section of the oligonucleotide probes. Unlike the sequence of the complementary sections, the sequence of the primers is not dictated by the target sequence. Primer sequences may therefore conveniently be designed by assembling the sequence from tetramers of nucleotides wherein each tetramer contains one A, T, C and G or by other ways that ensure that the G/C content and melting temperature of the primers are identical or very similar. The length of the primers (and corresponding primer-binding sites in the tag section of the second probe and in the compound primer) is preferably at least 12, or 17 nucleotides and preferably not more than 25, 30, 40 nucleotides.

In a preferred embodiment, at least two of the second oligonucleotide probes that are complementary to at least two different target sequences in a sample comprise a tag section that comprises a primer-binding section that is complementary to a single primer sequence. In a preferred embodiment, at least two of the oligonucleotide compound primers that are complementary to at least two different first target specific sections of two first probes in a sample comprise a primer-binding section that is complementary to a single primer sequence. Thus, preferably at least one of the first and second primer in a primer set is used for the amplification of elongated compound primers corresponding to at least two different target sequences in a sample, more preferably for the amplification of elongated compound primers corresponding to all target sequences in a sample. Preferably only a single first primer is used and in some embodiments only a single first and a single second primer is used for amplification of all elongated compound primers. Using common primers for amplification of multiple different fragments usually is advantageous for the efficiency of the amplification step.

The elongated compound primers obtained from the ligation of the adjacently annealed probe sections and subsequent annealing and elongation of the compound primer are amplified in step (h), using a primer set, preferably consisting of a set of primers for each of the elongated compound primers in the sample. The primer set comprises primers that are complementary to primer-binding sequences that are present in the elongated compound primers. A primer set usually comprises a first and at least a second primer, but may consist of only a single primer that primes in both directions. Excellent results have been obtained using primers that are known in the art as AFLP-primers such as described inter alia in EP534858 and in Vos et al., Nucleic Acid Research, 1995, vol. 23, 4407-44014.

Selective Primers

In certain embodiments, one or more of the primers used in the amplification step of the present invention is a selective primer. A selective primer is defined herein as a primer that, in addition to its universal sequence which is complementary to a primer binding site in the probe, contains a region that comprises so-called "selective nucleotides". The region containing the selective nucleotides is located at the 3'-end of the universal primer.

The principle of selective nucleotides is disclosed inter alia in EP534858 and in Vos et al., Nucleic Acid Research, 1995, vol. 23, 4407-44014. The selective nucleotides are complementary to the nucleotides in the (ligated) probes that are located adjacent to the primer sequence. The selective nucleotides generally do not form part of the region in the (ligated) probes or the elongated compound primer that is depicted as the primer sequence. Primers containing selective nucleotide are denoted as +N primers, in which N stands for the number of selective nucleotides present at the 3'-end of the primer. N is preferably selected from amongst A, C, T or G.

N may also be selected from amongst various nucleotide alternatives, i.e. compounds that are capable of mimicking the behaviour of ACTG-nucleotides but in addition thereto have other characteristics such as the capability of improved hybridisation compared to the ACTG-nucleotides or the capability to modify the stability of the duplex resulting from the hybridisation. Examples thereof are PNA's, LNA's, inosine etc. When the amplification is performed with more than one primer, such as with PCR using two primers, one or both primers can be equipped with selective nucleotides. The number of selective nucleotides may vary, depending on the species or on other particulars determinable by the skilled man. In general the number of selective nucleotides is not more than 10, but at least 5, preferably 4, more preferably 3, most preferred 2 and especially preferred is 1 selective nucleotide.

A +1 primer thus contains one selective nucleotide; a +2 primer contains 2 selective nucleotides etc. A primer with no selective nucleotides (i.e. a conventional primer) can be depicted as a +0 primer (no selective nucleotides added). When a specific selective nucleotide is added, this is depicted by the notion +A or +C etc.

By amplifying a set of elongated compound primers with a selective primer, a subset of elongated compound primers is obtained, provided that the complementary base is incorporated at the appropriate position in the design of the probes that are supposed to be selectively amplified using the selective primer. Using a +1 primer, for example, the multiplex factor of the amplified mixture is reduced by a factor 4 compared to the mixture of ligated probes prior to amplification. Higher reductions can be achieved by using primers with multiple selective nucleotides, i.e. 16 fold reduction of the original multiplex ration is obtained with 2 selective nucleotides etc.

When an assay is developed which, after ligation, is to be selectively amplified, it is preferred that the probe contains the complementary nucleotide adjacent to the primer binding sequence. This allows for pre-selection of the ligated probe to be selectively amplified.

The use of selective primers in the present invention has proven to be advantageously when developing ligation based assays with high multiplex ratios of which subsequently only a specific part needs to be analysed resulting in further cost reduction of the ligation reaction per datapoint. By designing primers together with adjacent selective nucleotides, the specific parts of the sample that are to be amplified separately can be selected beforehand.

One of the examples in which this is useful and advantageous is in case of analysis of samples that contain only minute amounts of DNA and/or for the identification of different (strains of) pathogens. For example, in an assay directed to the detection of various strains of anthrax (*Bacillus anthracis*), for each of the strains a set of representative probes is designed. The detection of the presence, absence or amount of this set (or a characterising portion thereof) of elongated compound primers after the hybridisation and ligation steps of the method of the invention may serve as an identification of the strain concerned. The selective amplification with specifically designed primers (each selective primer is linked to a specific strain) can selectively amplify the various strains, allowing their identification. For instance, amplification with an +A primer selectively amplifies the ligated probes directed to strain X where a +G primer selectively amplifies the ligated probes directed to strain Y. If desired, for instance in the case of small amounts of sample DNA, an optional first amplification with a +0 primer will increase the amount of ligated probes, thereby facilitating the selective amplification.

For example, a universal primer of 20 nucleotides becomes a selective primer by the addition of one selective nucleotide at its 3' end, the total length of the primer now is 21 nucleotides. Alternatively, the universal primer can be shortened at its 5' end by the number of selective nucleotides added. For instance, adding two selective nucleotides at the 3' end of the primer sequence can be combined with the absence (or removal) of two nucleotides from the 5' end of the universal primer, compared to the original universal primer. Thus a universal primer of 20 nucleotides is replaced by a selective primer of 20 nucleotides. These primers are depicted as 'nested primers' throughout this application. The use of selective primers based on universal primers has the advantage that amplification parameters such as stringency and temperatures may remain essentially the same for amplification with different selective primers or vary only to a minor extent. Preferably, selective amplification is carried out under conditions of increased stringency compared to non-selective amplification. With increased stringency is meant that the conditions for annealing the primer to the ligated probe are such that only perfectly matching selective primers will be extended by the polymerase used in the amplification step. The specific amplification of only perfectly matching primers can be achieved in practice by the use of a so-called touchdown PCR profile wherein the temperature during the primer annealing step is stepwise lowered by for instance 0.5° C. to allow for perfectly annealed primers. Suitable stringency conditions are for instance as described for AFLP amplification in EP 534858 and in Vos et al., Nucleic Acid Research, 1995, vol. 23, 4407-44014. The skilled man will, based on the guidance find ways tot adapt the stringency conditions to suit his specific need without departing from the gist of the invention.

One of the further advantages of the selective amplification of ligated probes is that an assay with a high multiplex ratio can be adapted easily for detection with methods or on platforms that prefer a lower multiplex ratio.

One of many examples thereof is the detection based on length differences such as electrophoresis and preferably capillary electrophoresis such as is performed on a MegaBACE or using nano-technology such as Lab-on-a-Chip.

Amplification

In step (h) of the method of the invention, the elongated compound primers are amplified to produce an amplified sample comprising amplified (detectable) elongated compound primers (amplicons) that are representations of the target nucleotide sequence by any suitable nucleic acid amplification method known in the art. Nucleic acid amplification methods usually employ two primers, dNTP's, and a (DNA) polymerase. A preferred method for amplification is PCR. "PCR" or "Polymerase Chain Reaction" is a rapid procedure for in vitro enzymatic amplification of a specific DNA segment. The DNA to be amplified is denatured by heating the sample. In the presence of DNA polymerase and excess deoxynucleotide triphosphates, oligonucleotides that hybridise specifically to the target sequence prime new DNA synthesis. It is preferred that the polymerase is a DNA polymerase that does not express strand displacement activity or at least not significantly. Examples thereof are Amplitaq and Amplitaq Gold (supplier Perkin Elmer) and Accuprime (Invitrogen). One round of synthesis results in new strands of determinate length, which, like the parental strands, can hybridise to the primers upon denaturation and annealing. The second cycle of denaturation, annealing and synthesis produces two single-stranded products that together compose a discrete double-stranded product, exactly the length between the primer ends. This discrete product accumulates exponentially with each successive round of amplification. Over the course of about 20 to 30 cycles, many million-fold amplification of the discrete fragment can be achieved. PCR protocols are well known in the art, and are described in standard laboratory textbooks, e.g. Ausubel et al., Current Protocols in Molecular Biology, John Wiley & Sons, Inc. (1995). Suitable conditions for the application of PCR in the method of the invention are described in EP-A 0 534 858 and Vos et al. (1995; Nucleic Acids Res. 23: 4407-23:4407-4407-4407-4414), where multiple DNA fragments between 70 and 700 nucleotides and containing identical primer-binding sequences are amplified with near equal efficiency using one primer set.

Other multiplex and/or isothermal amplification methods that may be applied include e.g. Rolling circle amplification, LCR, self-sustained sequence replication (3SR), Q-β-replicase mediated RNA amplification, or strand displacement amplification (SDA). In some instances, this may require a different design of the probes and compound primers.

Amplicons

The term 'amplicon' as used herein refers to the product of the amplification step of the elongated compound primer. The term 'amplicon' as used herein thus refers to an amplified elongated compound primer. After the ligation step wherein the two target specific section are connected by mean of a ligase, a compound primer is combined with the connected or ligated probe and is elongated. The elongated compound primer is combined with one or more primers and a polymerase and amplified to produce amplicons. The ligated probe, the primers, the polymerase and/or other parameters and variables are such that the amplification results in amplified linear representations of the connected probe.

Preferably an amplicon is a monomeric representation of the amplified connected probe. The various embodiments of the present invention will provide further detail in this respect.

Detection

The amplicons of the present invention can be detected on a suitable detection platform. The discrimination between amplicons derived from different target sequences can be based on length, sequence or mass as the primary parameter. Detection of the (labelled) samples is performed by a detector to result in detection data. The detector is of course dependent on the general system on which the separation is carried out (length, mass or sequence or a combination thereof) but is, if applicable, also depending on the label that is present on the primer, such as a fluorescent or a radioactive label.

Examples of suitable detection platforms are length based detection platforms, sequence based detection platforms and mass based detection platforms.

Length Based Detection

One of many examples of length based detection is the detection based on electrophoresis (capillary electrophoresis, slab-gel electrophoresis, fixed detector-continuous gel-electrophoresis) and preferably capillary electrophoresis such as is performed on MegaBACE equipment available from Amersham Biosciences, or using nano-technology such as Lab-on-a-Chip or other micro-eluidic devices. The difference in length of the amplicon being detected can be provided by the use of one or more identifiers.

The amplicons in a sample are preferably analysed on an electrophoretic device. The electrophoretic device preferably separates the different amplicons in an amplified sample on the basis of length (mobility), after which the separated amplicons may be detected as described herein. The electrophoretic device preferably is a multichannel device in which multiple samples are electrophoresed in multiple channels, preferably in parallel. The electrophoretic device has an application location (per channel) for application (loading) of the amplified sample to be electrophoresed, a separation area over which the fragments in the sample migrate by electrophoresis, and preferably also a detection device located at a detection location distal from the application location. The detection device will usually comprise a photomultiplier for the detection of fluorescence, phosphorescence or chemiluminescence. Alternatively, in the case of gel-electrophoresis, the separated fragments may be detected in the gel e.g. by autoradiography or fluorography.

Length Discrimination

To discriminate between different target sequences in the sample preferably a difference in length of the respective corresponding amplicons is used. By separating the amplicons based on length, the presence of the corresponding target sequences in the sample can be determined. Accordingly, in a preferred embodiment of the present invention, the discrimination between amplicons derived from different target sequences in a sample is based on a length difference between the respective amplicons corresponding to different target sequences in a sample or amplified sample.

Preferably, the length difference is provided by the length of the identifier sequence(s) in the oligonucleotide second probes and/or compound primers of the invention. By including in at least one of the oligonucleotide probes of the pair of the invention, but preferably in both (second probe and compound primer) of the set an identifier of a pre-determined length, the length of each amplified elongated compound primer in an amplified sample can be controlled such that an adequate discrimination based on length differences of the amplicons obtained is enabled. In a preferred embodiment of a probe of the pair according to the invention, the identifier is located between the second probe's section complementary to the target sequence and the primer-binding sequence. Preferably, the total length of the identifier is provided by the combination of the length of the identifier in the compound primer and the length of the identifier in the second probe. Accordingly, in a preferred embodiment, both the compound oligonucleotide primer and the second oligonucleotide probe comprise an identifier. The length differentiation between amplicons obtained from target sequences in the sample is preferably chosen such that the amplicons can be distinguished based on their length. This is accomplished by using identifier sequences or combinations of identifier sequences in the compound primers and/or second probes of the set of probes, which (together) result in length differences that may be distinguished on electrophoretic devices. Thus, from the perspective of resolving power, the length differences between the different amplified elongated compound primers, as may be caused by their identifiers, are as large as possible. However, for several other important considerations, as noted hereinbefore, the length differences between the different amplicons is preferably as small as possible: (1) the upper limit that exists in practice with respect to the length of chemically synthesised probes of about 100-150 bases at most; (2) the less efficient amplification of larger fragments, (3) the increased chances for differential amplification efficiencies of fragments with a large length variation; and (4) the use of multiple injections of detection samples on the detection device which works best with fragments in a narrow length range. Preferably the length differences between the sequences to be determined and provided by the identifiers are at least sufficient to allow discrimination between essentially all amplicons. By definition, based on chemical, enzymatic and biological nucleic acid synthesis procedures, the minimal useable size difference between different amplicons in an amplified sample is one base, and this size difference fits within the resolving power of most electrophoresis devices, especially in the lower size ranges. Thus based on the above it is preferred to use multiplex assays with amplification products with differ in length by a single base(pair). In a preferred embodiment, the length difference between different amplicons in an amplified sample is at least two nucleotides. In a particularly preferred embodiment of the invention the amplicons corresponding to different target sequences in a sample have a length difference of two nucleotides.

Length and Label

Throughput can be increased by the use of multiple labelled primers. One of the problems associated with the use of different labels in one sample is cross talk or residual cross talk. Cross talk or residual cross talk, as used herein, refers to the overlap between the emission spectra of different (fluorescent) labels. For instance when fluorescent dyes are used, each dye has a different emission (and absorption) spectrum. In case of two dyes in one sample, these spectra can overlap and may cause a disturbance of the signal, which contravenes the quality of the data obtained. Particularly when two nucleotide fragments to be detected in a sample are labelled with a different label and one of the fragments is present in an abundant amount whereas the other is present only in minute amounts, residual cross talk can cause that the measured signal of the fragment that is present in only minute amounts is mostly derived from the emission of another label with an overlapping emission spectrum that is abundantly contained in a fragment with identical size of another sample. The reciprocal effect of the other dye may also occur but in this example its effect is probably less because of the abundance differences between the amplicons labelled with the respective dyes.

Chehab et al. (Proc. Natl. Acad. Sci. USA, 86:9178-9182 (1989) have attempted to discriminate between alleles by attaching different fluorescent dyes to competing alleles in a single reaction tube by selecting combinations of labels such that the emission maximum of one dye essentially coincides with the emission minimum of the other dye. However, at a certain wavelength at which one dye expresses an absorption maximum, there is always also some remaining absorption from another dye present in the sample, especially when the sample contains multiple dyes.

This route to multiplex analysis was found to be limited in scale by the relatively few dyes that can be spectrally resolved. One of the major problems with the use of multiple dyes is that the emission spectra of different fluorescent labels often overlap. The resulting raw data signals have to be corrected for the contribution of similar size fragments that are detected simultaneously and are labelled with another fluorescent dye by a process called cross-talk correction. Cross-talk correction is commonly carried out by mathematical means, based on the known theoretical absorption spectra for both dyes, after "raw" data collection from the detection device. Mathematical correction is based on theoretical spectra and ignores that emission spectra of labels are sensitive and often affected by the composition of the detection sample. These sensitivities can affect the brightness and/or the wavelength of the emission. This means that parameters such as pH, temperature, excitation light intensity, non-covalent interactions, salt concentration and ionic strength strongly influence the resulting emission spectrum. In particular, it is known that the presence of residual salts in a sample affects the fluorescence signal emitted by the dye and is a critical factor in case of detection by capillary electrophoresis using electrokinetic injection because it then also affects the injection efficiency. Thus, spectral overlap is a potential source of error that negatively impacts on data quality in case of multiplex detection using different fluorescent dyes.

The present invention provides for a solution to this problem such that two (or more) labels with overlapping spectra can be used in the same sample without significantly affecting data quality. By a predetermined combination of length differences and labels, an increase in the number of target nucleotide sequences that can be detected in sample is obtained while the quality of the data remains at least constant. In a preferred embodiment of the invention, spectral overlap between two differently labelled sequences is reduced by the introduction of a length difference between the two sequences. This label-related length difference can be provided for by the length of the identifier sequence as described herein. The number of different labels that can be used in the same sample in the present method is at least two, preferably at least three, more preferably at least four. The maximum number of labels is functionally limited by the minimum of spectral overlap that remains acceptable, which for most applications typically amounts to less than 15 percent of the true signal, preferably less than 10 percent, more preferably lees than 5 percent and most preferably less than 1 percent of the true signal.

In order to avoid the potential influence of residual cross-talk on the data quality in case different samples are labelled with multiple fluorescent dyes with overlapping emission spectra and fragments with identical length are detected simultaneously in the same run, in a particular preferred embodiment it is preferred to choose the identifier sequences such that amplicons differ by at least two base pairs (nucleotides) within a multiplex set and differ by a single base pair between multiplex sets labelled with the different dyes that have overlapping spectra. By doing so, the length of the fragments labelled with the respective dyes can be chosen such that the potential influence of residual cross-talk on the quality of the data is circumvented because unique combinations of fragments size and labelling dye are defined.

A particular preferred embodiment of the invention is directed to a method in which a sample comprising amplicons is derived from a multiplicity of target sequences. These amplicons are differently labelled, thereby defining groups of amplicons carrying the same label. Within each group, the identifier provided for a length difference of at least two, preferably two nucleotides. Between two groups with labels having spectral overlap, the identifier provides a length difference of one nucleotide, effectively resulting in one group having an even number of nucleotides and one group having an odd number of nucleotides as described above.

In one aspect the present invention pertains to a method for the improved discrimination and detection of target sequences in a sample, comprising providing at least a two or more groups of oligonucleotide probes, wherein the amplicons obtained with different groups of oligonucleotide probes have different labels, wherein substantially each amplicon within a group has the same label, wherein within a group of identically labelled amplicons a length difference is provided between each identically labelled probe within that group, wherein between the first and second group an additional length difference is provided such that each amplicon in the amplified sample is characterised by a combination of length of the sequence and the label.

In a preferred embodiment of the method of the invention, at least two groups of sets of first and second probes and compound oligonucleotide primers are provided to a sample, whereby each group of second oligonucleotide probes has tag sequences with at least one group specific primer-binding site. Similarly the group of compound primers comprises one group specific primer-binding site. The elongated compound primers of each group are amplified from a primer set wherein at least one of the first and second primers is complementary to the group specific primer-binding site, and whereby at least one of the first and second primers of a group comprises a group specific label. In each group, an amplicon corresponding to a target sequence in the sample differs in length from an amplicon corresponding to a different target sequence in the sample. The group specific labels are preferably such that the detection device can distinguish between the different group specific labels. The length difference is preferably provided by the length of the identifier sequence. Preferably in this embodiment of the method of the invention, a first part of the groups has amplicons having an even number of nucleotides and a second part of the groups has amplicons having an odd number of nucleotides. Preferably, the groups of amplicons having an even number of nucleotides and the groups of amplicons having an odd number of nucleotides are labelled with (fluorescent) labels, which have the least overlap in their emission spectra. Thus, two groups of amplicons, each group having an odd number of nucleotides are labelled with labels which have the least overlap in their emission spectra. The same holds for two groups of amplicons, each group having an even number of nucleotides. Two groups of amplicons, one group having an odd number of nucleotides and the other group having an even number of nucleotides are labelled with labels that have a larger overlap in their emission spectra. The relative notions as used herein of 'the least overlap in their emission spectra' and 'have a larger overlap in their emission spectra' refer to a group of labels from which a selection of the labels can be made for use in the present invention. This group of labels may depend on the detection platform used to other factors such as those disclosed herein before. In a particularly preferred embodiment of this method, a first and second groups of amplicons having an even number of nucleotides are produced and a third and fourth group of amplicons having an odd number of nucleotides are produced and whereby the first and second group are labelled with FAM and NED, respectively, and the third and fourth group are labelled with (ET-)ROX and either JOE or HEX, respectively, or vice versa, whereby the first and second group are labelled with (ET-)ROX and either JOE or HEX, respectively, and the third and fourth group are labelled with FAM and NED, respectively. Thus, in these embodiments, the fluorescent labels are chosen such that the groups of amplicons that co-migrate, because they both contain fragments with either even or odd numbers of nucleotides, have labels which have the least overlap in their emission spectra, thereby avoiding as much as possible cross-talk in the detection of amplicons in different groups (see also below).

In a preferred embodiment to avoid cross-talk it is therefore desirable to combine a difference in length with a different label when analysing a set of amplicons in such a way that the influence of spectral overlap on the data quality is avoided by length differences between the amplicons labelled with the dyes that have overlapping emission spectra.

It is preferred that in each sample amplicons derived from each target sequence differ from any other amplicons in the sample in length, and/or in the label or, preferably in the combination of the length and the label. To provide for an adequate separation of the amplicons of different length it is preferred that the length difference between two different amplicons is at least two nucleotides, preferably two. When detecting polymorphisms it is preferred that the difference in length between two or more (SNP) alleles of the polymorphism is not more than two, thereby ensuring that the efficiency of the amplification is similar between different alleles or forms of the same polymorphism. This implies that preferably both alleles are amplified with the same set of primers and hence will be labelled with the same dye.

In a preferred embodiment, for example directed to the detection of different alleles of a multiplicity of loci, the distribution between odd/even lengths within a group can be designed in the following way. Two loci L1, L2 are each represented by two alleles A11, A12 for L1 and A21, A22 for L2. The lengths of the various alleles (or amplicons representing those alleles) is such that A11>A12>A21>A22; A12−A11=2; A22−A21=2; A12−A21=3. Between groups G1 and G2 carrying labels that may have an overlap in their spectra there can be a length difference of 1 nucleotide. Thus G1(A11)−G2(A11)=1, hence the group starts with either an even or an uneven length.

This distribution has some significant advantages compared to the more densely packed distribution disclosed herein. It is known that due to conformational differences different sequences of identical length generally differ in their electrophoretic mobility. When there is only a difference in length of one nucleotide, this may cause overlap between the peaks if the sequences are of a very different mobility. For instance the difference in mobility between two alleles of one locus (A11, A12), will be less than the difference in mobility between two alleles from different loci (A12, A21). When there is a significant difference in mobility between A12 and A21, this may lead to unreliable detection. By creating length distributions as herein disclosed this can be avoided. The lower throughput is then weighed against the reliability of the detection.

The problem of the overlap between the spectra of the different labels is then adequately avoided. This is schematically depicted in Table A.

TABLE A

Alternative distribution scheme of labels and lengths of probes.

| Length | Group 1-Label 1 | Group 2-Label 2 | Group 3-Label 3 | Group 4-Label 4 |
|---|---|---|---|---|
| N | G1A11 | | G3A11 | |
| N + 1 | | G2A11 | | G4A11 |
| N + 2 | G1A12 | | G3A12 | |
| N + 3 | | G2A12 | | G4A12 |
| N + 4 | | | | |
| N + 5 | G1A21 | | G3A21 | |
| N + 6 | | G2A21 | | G4A21 |
| N + 7 | G1A22 | | G3A22 | |
| N + 8 | | G2A22 | | G4A22 |
| N + 9 | | | | |
| N + 10 | G1A31 | | G3A31 | |
| N + 11 | | G2A31 | | G4A31 |
| N + 12 | G1A32 | | G3A32 | |
| N + 13 | | G2A32 | | G4A32 |
| N + 14 | | | | |
| N + 15 | G1A41 | | G3A41 | |
| N + 16 | | G2A41 | | G4A41 |
| N + 17 | G1A42 | | G3A42 | |
| N + 18 | | G2A42 | | G4A42 |

In an embodiment of the present invention there is provided between the amplicons within one group, a length difference of alternating two and three nucleotides, i.e. 0, 2, 5, 7, 10, 12 etc. The other group then has a length difference of 1, 3, 6, 8, 11, 13 etc. Based on the information disclosed herein, the skilled man may determine other ways of varying length differences within a range.

Multiple Injection

In order to come to a high throughput method of a multiplex of samples, a number of samples are treated similar to thereby generate a multiplicity of amplified samples which can then be analysed on a multichannel device which is at least capable of detecting the labels and/or length differences. Suitable devices are described herein above.

To increase throughput on electrophoretic platforms methods have been developed that are described in this application and are commonly depicted as multiple injection. By injecting multiple samples containing fragments of discrete, predetermined lengths, in the same electrophoretic matrix and/or in short consecutive runs, throughput can be increased. All detectable fragments preferably have a length within a specific span and only a limited number of fragments can be detected in one sample, hence the advantage of selective amplification for the reduction of the multiplex ratio by the selection of a subset of the elongated compound primers in the amplification step resulting in a subset of amplicons.

The methods of the present invention may be performed on two or more nucleic acid samples, each containing two or more different target nucleic acids, to produce two or more amplified samples in which is presence, absence or amount of amplicons is analysed.

The multiplex analysis of the amplified samples following the method of the invention comprises applying at least part of an amplified sample to an electrophoretic device for subsequent separation and detection. Preferably such an amplified sample contains, or is at least suspected to contain, amplicons, which is an indication that a target sequence has hybridised with the provided oligonucleotide probes and that those probes were annealed adjacently on the complementary target sequence so that they where connected, i.e. ligated. Subsequently, an amplified sample is subjected to a separating step for a selected time period before a next amplified sample is submitted.

In the method of the invention, (parts of) two or more different amplified samples are applied consecutively to the same channel of the electrophoretic device. Depending on the electrophoresis conditions, the time period between two (or more) consecutively applied amplified samples is such that the slowest migrating amplicons in an amplified sample is detected at the detection location, before the fastest migrating amplicons of a subsequently applied amplified sample is detected at the detection location. Thus, the time intervals between subsequent multiple injections in one channel of the device are chosen such that consecutively applied samples after separation do not overlap at a point of detection.

The method according to the invention allows for the high throughput analysis of a multiplicity of samples each comprising a multiplicity of different target sequences by the consecutive injection of amplified samples, comprising amplicons corresponding to the target sequences in the samples, in a channel of a multichannel electrophoretic device such as a capillary electrophoresis device. The method according to the invention allows for the analysis of a multiplicity of target sequences in a multiplicity of samples on a multiplicity of channels, thereby significantly increasing the throughput of the number of samples that can be analysed in a given time frame compared to conventional methods for the analysis of nucleotide sequences. This method profits from samples containing amplicons to be detected that are of a discrete size range as thereby the time period between the successive injections can be significantly reduced compared to methods in which no use is made of samples that contains sequences to be detected that are not within a discrete size range.

The selected time period prevents that consecutively applied samples after separation have an overlap of amplicons at the detection point. The selected time period is influenced by i). the length of the amplicons; ii). the length variation in the amplicons; and iii). the detection device and its operating conditions. Applying samples and separating consecutively applied samples in the same channel can be repeatedly performed in one or more channels, preferably simultaneously to allow for consecutive electrophoretic separation of multiple samples in one channel and/or simultaneous analysis of multiple samples over multiple channels and/or simultaneous analysis of multiple samples over multiple channels carried out consecutively.

The period of time between two consecutively loaded amplified samples can be determined experimentally prior to executing the method. This period of time is selected such that, given the characteristics of an amplified sample, especially the difference in length between the shortest and the longest amplicons in an amplified sample, as well as other experimental factors such as gel (matrix) and/or buffer concentrations, ionic strength etc., the fragments in an amplified sample are separated to such extent at the detection location which is located at the opposite end (distal) from the application location where the sample was applied, that the different amplicons in a sample may be individually detected. After applying the last amplified sample, the separation can be continued for an additional period of time to allow the amplicons of the last sample to be separated and detected. The combination of the selected period of time between applying two consecutive samples and the optional additional time period is chosen such that at the detection location the different amplicons in consecutively applied samples are separated such that they may be individually detected, despite the limited length variation that exists between the different amplicons within a single sample. Thus overlapping migration patterns are prevented when samples containing fragments of varying length are consecutively applied (injected) on the electrophoretic device.

Using the method according to the invention, it is in principle possible and preferred to continuously apply, load or inject samples. Preferably the device is able to perform such operation automatically, e.g. controlled by a programmable computer. Preferably the multichannel device is suitable for such operation or is at least equipped for a prolonged operation without maintenance such as replacement of buffers, parts etcetera. However, in practice this will generally not be the case. When a final sample is submitted it is generally needed to continue the separation for an additional time period until the last fragment of the final sample has been detected.

In a preferred embodiment of the invention, the identifiers present in both the compound primer and second oligonucleotide probes of the set of probes are used to provide the length differences (i.e. 0 to 500 nucleotides, bases or base pairs) between the amplicons. The total length of the amplicons and the variation in the length is governed mostly by the techniques by which these fragments are analysed. In the high throughput multiple injection method of the present invention, it is preferred that the range of lengths of amplicons in an amplified sample has a lower limit of 40, 60, 80, or 100 and an upper limit of 120, 140, 160, or 180 nucleotides, bases or base pairs, for conventional (capillary) electrophoresis platforms. It is particularly preferred that the range of lengths of the amplicons varies from 100 to 140 nucleotides. However, these numbers are strongly related to the current limits of the presently known techniques. Based on the knowledge provided by this invention, the skilled artisan is capable of adapting these parameters when other circumstances apply.

The reliability of the multiplex amplification is further improved by limiting the variation in the length of the amplicons. Limitations in the length variation of amplicons is preferred to use multiple injection more efficiently and further results in reduction of the preferential amplification of smaller elongated compound primers in a competitive amplification reaction with larger elongated compound primers. This improves the reliability of the high throughput method of the present invention. Together with the multiple injection protocol as herein disclosed, these measures, alone or in combination provide for a significant increase in throughput in comparison with the art. A further improvement of the high throughput capacity is obtained by limiting the number of different amplicons in a sample. It is regarded as more efficient and economical to limit the multiplex capacity of the ligation/amplification step in combination with the introduction of a multiple injection protocol. One of the most advantageous aspects of the present invention lies in the combination of the innovative set of probes (including the compound primer), multiplex ligation, multiplex amplification, preferably with a single primer set or with multiple primer sets which each amplify multiple elongated compound primers, repeated injection and multiplex detection of different labels, optionally in combination with selective priming that allows for the flexibility in multiplex ratio between ligation and amplification steps. One of the further advantageous aspects of the present invention resides in the combined application of length differences with different (overlapping) labels such that each elongated compound primer and hence each target sequence within one sample can be characterised by an amplicon having a unique combination of length and label. This allows for a significant improvement of the efficiency of the analysis of target sequences as well as a significant reduction in the costs for each target analysed.

The multiple injection protocol can be performed in a variety of ways. One of these ways is the multiple loading of two or more samples in the same matrix. This is considered as advantageously as the matrix is re-used by performing consecutive short runs, thereby increasing efficiency and throughput. Another way is the multiple loading of two or more samples in the same matrix in the same run. It is preferred to re-use the matrix by performing short consecutive runs. In this embodiment, a first sample is injected and separated. As soon as the last fragment is detected, the next sample is loaded. Preferably, between these two consecutive short runs the matrix is not replaced so that the runs are performed in the same matrix. This provides for additional efficiency and improved economics as less changes o the matrix need to occur, reducing the amount of consumables of this type of analysis (i.e. buffers etc.), reducing the cost per datapoint. Furthermore time-consuming replacements of the matrix can be avoided to a large extent, further increasing the efficiency of the method.

In itself, certain aspects of multiple loadings or multiple injections have been described inter alia in U.S. Pat. No. 6,156,178 and WO 01/04618. The latter publication discloses an apparatus and a method for the increased throughput analysis of small compounds using multiple temporally spaced injections. The publication discloses that samples comprising primers, extended by one nucleotide (single nucleotide primer extension or SnuPE, also known as minisequencing) could be detected using multiple temporally spaced injections on a capillary electrophoresis device. Minisequencing is based on annealing a complementary primer to a previously amplified target sequence. Subsequent extension of the primer with a separately provided labelled nucleotide provides for identification of the nucleotide adjacent to the primer. Principally, the primer extension product is of a constant length. To increase throughput the use of successive injections of extension products of the same length per run is suggested. To further increase the throughput, primers of a different length can be used, varying typically from 15 to 25 nucleotides. In contrast, the present invention contemplates analysing multiplex amplification products themselves directly with a length variation typically between 50 and 150 nucleotides. This is significantly more economical than minisequencing or SnuPE as outlined hereinbefore because multiple target sequences are amplified in a single reaction, whereas with minisequencing or SnuPE amplification is carried out individually for each target sequence. Furthermore, the use of primers of a different length and complementary to the target sequence compromises the efficiency of the subsequent amplification step needed in the method of the present invention.

The efficiency of the present invention can be illustrated as follows. When a capillary electrophoretic device with 96 channels and capable of detecting four labels simultaneously is used, allowing for 12 subsequent injections per run per channel with a empirically optimised minimum selected time period between the injections, a sample containing 20 target sequences of interest allows for the high throughput detection of 96 (channels)*12 (injections)*20 (targets)*4 (labels)= 92160 target sequences, using the method of the present invention. In the case of co-dominant SNP-detection, data regarding 46080 SNPs can be detected in a single run.

Size Ladder

The sample can be supplied with a nucleotide fragment size standard comprising one or more nucleotide fragments of known length. Methods of preparing and using nucleotide size standards are well known in the art (see e.g. Sambrook and Russell, 2001, supra). Such a size standard forms the basis for appropriate sizing of the amplicons in the sample, and hence, for the proper identification of the detected fragment. The size standard is preferably supplied with every sample and/or with every injection. A size standard preferably contains a variety of lengths that preferably spans the entire region of lengths to be analysed. In a particular embodiment of the invention, it is considered advantageously to add flanking size standards from which the sizes of the amplicons can be derived by interpolation. A flanking size standard is a size standard that comprises at least two labelled oligonucleotide sequences of which preferably one has a length that is at least one base shorter than the shortest amplicon and preferably one that is a least one base longer than the longest amplicon to allow interpolation and minimise the introduction of further length variation in the sample. A preferred flanking size standard contains one nucleotide that is one nucleotide shorter the shortest amplicon and one that is a least one base longer than the longest amplicon and is labelled with at least one dye that is identical to the label used for labelling the amplicons contained in the sample.

A convenient way to assemble a suitable size standard is by (custom) chemical synthesis of oligonucleotides of the appropriate lengths, which are end-labelled with a suitable label. The size standard is applied with every consecutively applied sample to serve as local size references to size the loaded sample fragments. The size standard may be applied in the same channel or lane of the electrophoretic device as the sample to be analysed, i.e. together with the sample, or may be applied in a parallel channel or lane of a multichannel/lane device. The flanking size standard can be labelled with any of the labels used in the method. If the size standard is applied in the same channel of the device, the fragments of the standard are preferably labelled with a label that can be distinguished from the labels used for the detection of the amplicons in a sample.

Sequence Based Detection

Examples of sequence based detection platforms are solid phase and fluid phase microarrays. Preferably, uniquely addressable arrays are used wherein the probe contains a unique sequence (such as a ZIP sequence) thereby providing that the amplicon will hybridise to a predetermined spot on the array wherein the complementary ZIP sequence is located (cZIP). Array-based detection methods are commonplace nowadays and the technology is widely spread, allowing the skilled man to create a suitable array for the detection of the amplicons of the present invention. Examples of suitable array based detection methods are for instance WO 97/27317, WO 97/22720, WO 97/43450, EP 0 799 897, EP 0 785 280, WO 97/31256, WO 97/27317, WO 98/08083, and the Genechips array, the Affymetrix DNA chip and the VLSIPS™ array. Especially suitable and preferred detection platforms for the assay of the present invention are arrays described in inter alia WO9902266, EP1050588, WO0119517, WO02072263, WO02072268, WO02072266, the so-called Pam arrays.

Mass Based Detection

An example of mass based platforms is MALDI-TOF. The analytes to be detected each have a different mass. This can be achieved for instance by the incorporation of a identifier sequence comprising a restriction site in the second probe or the compound primer. When the elongated compound primers are restricted prior to detection (optionally after amplification), a set of fragments/oligonucleotides are obtained, each having a different mass that is associated with the presence, absence or amount of a target sequence in the sample.

One embodiment of the invention using mass based detection relates to a method for determining the presence, absence or amount of a target sequence in a nucleic acid sample, wherein the presence, absence or amount of the target sequence is determined by an oligonucleotide ligation assay in combination with a detection method based upon molecular mass and wherein each target sequence in the sample is represented by an identifier and detection of the target sequences is based on the detection of the presence or the absence of a fragment comprising said identifier. This method has also been disclosed in WO03/030163 by applicant.

In certain embodiments, the invention pertains to a method for determining the presence, absence or amount of a target nucleotide sequence in a nucleic acid sample, the method comprising the steps of:

a) providing to a nucleic acid sample at least one first probe for each target sequence to be detected in the sample, whereby the first probe has a first target specific section that is complementary to a first part of the target sequence and at least one second probe for each target sequence to be detected in the sample, whereby the second probe has a second target specific section that is complementary to a second part of the target sequence, whereby the first and second part of the target sequence are located adjacent to each other, and whereby the second probe further comprises a tag section that is essentially non-complementary to the target sequence, whereby the tag section comprises a first primer-binding sequence;

b) allowing the first and second target specific sections of the first and second probe to anneal to the first and second parts of target sequences whereby the first and second target specific sections of the probes are annealed adjacent on the target sequence;

c) providing means for connecting the first and second target specific sections annealed adjacently to the target sequence and allowing the first and second target specific sections to be connected, to produce a connected probe corresponding to a target sequence in the sample;

d) providing to the mixture resulting from step c) a compound primer that comprises a section that is complementary to at least part of the first target specific section and a second primer binding section;

e) allowing the compound primer to anneal to at least part of the first target specific section;

f) elongating the compound primer;

g) providing a set of primers comprising a first primer having a sequence essentially identical to the first primer-binding section, and a second primer that is complementary to the second primer-binding section;

h) amplifying the resulting mixture to produce an amplified sample comprising amplicons that are representations of the connected probes;

i) determining the presence, absence or amount of a target sequence in a sample by detecting the presence, absence or amount of the corresponding amplicon;

wherein at least one of the compound primer and second oligonucleotide probe further comprises a restriction site for a restriction enzyme, which restriction site is located between the respective primer binding site and the section of the oligonucleotide probe that is complementary to the first probe or to the second part of the target sequence respectively and wherein an identifier is located between the restriction site and the primer binding site and wherein the method further comprises the step of digesting the amplicons with the restriction enzyme to produce a detectable fragment prior to step i).

The amplicons are cleaved or cut. Cleaving the amplicons can be achieved by any suitable means known in the art as long as a reproducible cleaved or cut nucleotide strand is obtained. Reproducible in this respect refers to the preference that the means for cleaving or cutting cut the nucleotide sequence at the same position in the sequence of the amplicons. The means for cleaving the amplicons can be chemical or enzymatic, but are preferably enzymatic, such as a restriction enzyme. A preferred restriction enzyme is a restriction endonuclease. An amplicon is preferably cleaved by the restriction enzyme at the restriction site that was provided in the tag of the second probe or in the compound primer between the primer binding site and the section that is complementary to the first target specific section. Cleaving the amplicons produces either flush ends in which the terminal nucleotides of both strands resulting from the restriction step are base-paired, or staggered ends in which one of the ends resulting from the restriction step protrudes to give a (short) single strand extension. Preferably the restriction site is recognised by a sequence specific restriction endonuclease. In principle any restriction endonuclease known in the art can be used, as long as it produces a reproducible cut. Cleaving the amplicons in the sample results in a detectable fragment. In certain embodiments, additional oligonucleotides are provided to create double stranded nucleic acids that can be cleaved by the restriction enzyme.

Restriction endonucleases itself are widely known in the art. A suitable restriction enzyme can have a recognition sequence of 4, 5, 6, 7, or 8 or more nucleotides. Preferably the restriction endonuclease is a rare cutter, (i.e. has a recognition sequence of more than 4 nucleotides). Preferably the restriction enzyme is a type II enzyme or a type IIs enzyme. Preferred restriction enzymes are EcoRI, HindIII, BamHI. Other preferred restriction enzymes are 6-cutter restriction enzymes, preferably 6-cutters that are relatively inexpensive.

Digesting amplicons in step (e), for instance with restriction endonucleases, results in detectable fragments (comprising the identifier sequence) and the remains of the amplicons (waste fragments). The waste fragments, comprises part of the elongated compound primer. Digesting with a restriction endonuclease results in a detectable fragment which is double stranded. Both the detectable fragments and the waste fragments consist of two strands, one designated as the top strand and the other as the bottom strand. The detectable fragment can be subjected to a denaturation treatment to provide for the separate bottom strand and top strands. The bottom strand is essentially complementary to the top strand, i.e. the largest part of the nucleotide sequence of the top and bottom strand are complementary, with the exception of those nucleotides that are part of a staggered or sticky end, essentially as described herein-before. Either the top or the bottom strand can be detected, or both the top and the bottom strand.

Detection is based on the detection of the presence, absence or amount of the detectable fragment. Detection of the detectable fragment is preferably indicative of the presence, absence or amount of the amplicons in the amplified sample and hence of the target nucleotide sequence in the nucleic acid sample. Preferably the detection is based on the detection of the top and/or the bottom strand of the detectable fragment. The detection of the bottom strand in addition to the top strand has the advantage that direct confirmation of the presence, absence or amount of the target sequence is obtained in duplo.

The detection can be performed directly on the digested sample, but it is preferred that, prior to detection, the detectable fragment is isolated, purified or separated from the digested amplified connected probes. The detectable fragment can be isolated, purified or separated from the digested amplicons by means known in the art such as spin column purification, reversed phase purification or, preferably by affinity labelling techniques such as a biotin-streptavidin combination, combined with a suitable carrier such as magnetic beads, probe sticks, hybridisation based pull out etc. Isolation, purification or separation can also be performed after a denaturation treatment on the top and/or bottom strands.

The detectable fragment is preferably labelled with an affinity label. The affinity label is preferably located at the extreme end of the detectable fragment, located distal from the restriction site or, after digestion, the remains of the restriction site. The top strand and/or the bottom strand of the detectable fragment can be equipped with the affinity label. Preferably it is the bottom strand that comprises the affinity label and the identifier sequence. The notion top strand is generally used to indicate that the nucleotide sequence of the top strand at least in part corresponds to the part of the tag that comprises the identifier, the restriction site and the primer binding site, i.e. the top strand contains a nucleotide sequence that is essentially identical to that of the probe. The bottom strand is the strand complementary to the top strand and is obtained after a first round of amplification by extension of a primer complementary to the primer binding site in the top strand and which primer is preferably equipped with an affinity label. Accordingly, the bottom strand contains a sequence that corresponds to the nucleotide sequence of one of the primers. In a particular preferred embodiment the bottom strand is equipped with the affinity label. Preferably the bottom strand is isolated from the sample comprising the denatured detectable fragments, preferably by the affinity label. Preferably it is the bottom strand that is detected using mass spectrometry. Hence detection of the bottom strand provides the information relating to the presence or the absence of the corresponding target nucleotide strand.

The affinity label can be used for the isolation of the top and/or the bottom strand from the mixture of digested amplicons. As an affinity label, a biotin-streptavidin combination is preferred. The affinity labelled top strand, bottom strand or detectable fragment can subsequently be detected using detection techniques based on molecular mass.

As used herein, the term affinity label also encompasses affinity labels that are coupled via so-called 'linkers' (having a certain molecular mass) located between the nucleotide sequence of the tag and the actual affinity label.

In an alternative embodiment, the affinity label is provided in the tag that does not comprise the restriction site—identifier combination. This allows for the isolation of the amplicons prior to the digestion step. The resulting mixture, after restriction and optional denaturation, can directly be analysed using mass spectrometry. As the mass of the detectable fragments, or the top or bottom strands, is known or can at least be calculated, the waste fragments (i.e. the remains of the digested amplified connected probes) do not significantly compromise the detection as the detectable fragments, and both the top or bottom strands, are within a known and different mass range.

Detection techniques based on molecular mass are for instance mass spectrometry and more in particular the mass spectrometry techniques that are suitable for the detection of large molecules such as oligonucleotides. Examples of these techniques are matrix assisted laser desorption/ionisation time-of-flight (MALDI-TOF), HPLC-MS, GC-MS etcetera. Commonly the detection techniques based on molecular mass prefer that the submitted samples contain oligonucleotides in a single stranded form. In case the detectable fragment has been isolated as a double stranded oligonucleotide, the detectable fragment is preferably denatured, using techniques known in the art, to yield single stranded oligonucleotides for instance such as those described herein as top and/or bottom strands.

After digestion with a restriction endonuclease, the obtained detectable fragment preferably comprises a identifier, remains of the restriction site, if any, and the primer binding site. Optionally an affinity label can be attached to the top and/or the bottom strand, optionally via a linker. The mass to be detected hence is the summation of the molecular mass of the primer binding site, the identifier, the remains of the restriction site and the optional affinity label and optional linker.

To distinguish between different target sequences in a nucleic acid sample, the detectable fragments are designed such that a detectable fragment corresponding to one target sequence in the sample differs in mass from a detectable fragment corresponding to another target sequence in the sample. Accordingly, a sample comprising multiple target sequences comprises (after ligation, amplification and digestion) multiple detectable fragments, each detectable fragment with a different mass. Upon denaturation of the detectable fragments in the respective top and bottom strands, the various top strands each have a different mass. Likewise, the various bottom strands each have a different mass. Preferably, the mass difference between two different detectable fragments (and hence between two top or bottom strands respectively) is provided by the difference in mass of the identifier.

The top strand or the bottom strand can be regarded as comprising a constant section and a variable section. The constant section comprises the primer binding site, the optional affinity label (including the optional linker) and the remains of the restriction site. The variable section comprises the identifier. The constant section is constant within one sample and is of a constant mass. The variable section preferably provides the difference in mass between strands that correspond to different target nucleotides in a sample.

In one embodiment of the present invention, the detectable fragment (and consequently) the oligonucleotide probes are designed such that the constant section is also varied in mass. This allows for the creation of multiple regions within a mass spectrum. Each region will have a lower limit and an upper limit, thereby defining a window. The lower limit of the window is defined by the mass of the constant sequence. By using different constant sequences, different regions can be defined. Preferably, these regions do not overlap. Within one region a mass difference between the oligonucleotides to be detected is created by the mass difference between the identifiers essentially as described herein before. The upper limit of the region is at least the sum of the lower limit of the region and the identifier with the largest mass. For example, two constant sections have a mass of 6489 Dalton and 8214, respectively. Identifier sequences of up to two nucleotides provide for 15 different combinations including the absence of an identifier, hence mass j), each with a different molecular weight, ranging from 0 up to 642 (AG or GA). This allows for two regions, one ranging from 6489 Dalton to 7131 Dalton and one region from 8214 Dalton to 8856 Dalton. This allows for an increase of the multiplex capacity of the present invention. This also allows for the pooling of samples prior to mass analysis. Both will increase the high throughput capacity of the present invention.

To design identifiers that can be used in the probes of the present invention and that are capable of providing a unique mass to every detectable fragment and hence the top strand or bottom strand in the sample, the identifiers preferably have to meet the following requirements: i) a limited number of identical consecutive bases to avoid slippage of the polymerase during the amplification step; ii) no internal recognition site for the restriction enzyme; iii) minimal mass difference to ensure adequate resolution; iv) no formation of hairpins, for instance with other parts of the ligation probes for instance due to intramolecular hybridisation.

Identifiers suitable for use in the invention can be designed using a method that computes all possible identifier sequences up to a pre-determined length and that fulfil the criteria listed above (i-iv). This method can be performed using a computer program on a computer. This method can be considered as an invention in itself. The computer program can be provided on a separate data carrier such a as diskette. The method starts with providing the upper length limit of the identifier sequence. The method subsequently calculates all possible permutations of nucleotide sequences and through a process of elimination and selection applies the criteria i-iii as listed herein-before. The number of allowable consecutive bases can be provided separately or can be predetermined. The recognition site for the restriction enzyme can be provided as separate input, but can also be derived from a database of known recognition sites for the restriction enzyme, depending on whether or not other the presence of recognition sequences of other restriction enzymes is allowed. The minimal mass difference can also be provided as separate input or as a predetermined parameter. The formation of hairpins can be checked by using a standard PCR-primer selection program such as Primer Designer version 2.0 (copyright 1990, 1991, Scientific and Educational software). The resulting identifier sequences can be presented to the user in a suitable format, for instance on a data-carrier.

The method according to the invention allows for the analysis of a multiplicity of target sequences thereby significantly increasing the throughput of the number of samples that can be analysed. "Throughput" as used herein, defines a relative parameter indicating the number of samples and target sequences that can be analysed per unit of time.

Pooling

In a variant of the technology, the starting (DNA) material of multiple individuals are pooled such that less detection samples containing this material are loaded on the detection device. This can be advantageous in the case of Linkage Disequilibrium LD mapping) when the objective is to identify amplicons (such as those representing SNP alleles) that are specific for a particular pool of starting samples, for example pools of starting material derived from individuals which have different phenotypes for a particular trait.

Application

One aspect of the invention pertains to the use of the method in a variety of applications. Application of the method according to the invention is found in, but not limited to, techniques such as genotyping, transcript profiling, genetic mapping, gene discovery, marker assisted selection, seed quality control, hybrid selection, QTL mapping, bulked segregant analysis, DNA fingerprinting and microsatellite analysis. Another aspect pertains to the simultaneous high throughput detection of the quantitative abundance of target nucleic acids sequences. This approach is commonly known as Bulk Segregant Analysis (BSA).

Detection of Single Nucleotide Polymorphisms

One particular preferred application of the method according to the invention is found in the detection of single nucleotide polymorphisms (SNPs). A first oligonucleotide probe (and preferably the first probe) of the pair according to the invention comprises a part that is complementary to a part of the target sequence that is preferably located adjacent to the polymorphic site, i.e. the single polymorphic nucleotide. A second oligonucleotide probe (and preferably the second probe) of the pair according to the invention is complementary to the part of the target sequence such that its terminal base is located at the polymorphic site, i.e. is complementary to the single polymorphic nucleotide. If the terminal base is complementary to the nucleotide present at the polymorphic site in a target sequence, it will anneal to the target sequence and will result in the ligation of the two probes. When the end-nucleotide, i.e. the allele-specific nucleotide does not match, no ligation or only a low level of ligation will occur and the polymorphism will remain undetected.

When one of the target sequences in a sample is derived from or contains a single nucleotide polymorphism (SNP), in addition to the probes specific for that allele, further probes can be provided that not only allow for the identification of that allele, but also for the identification of each of the possible alleles of the SNP (codominant scoring). To this end a combination of types of probes can be provided: one type probe that is the same for all alleles concerned and one or more of the other type of probe which is specific for each of the possible alleles. These one or more other type of probes contain the same complementary sequence but differ in that each contains a nucleotide, preferably at the end, that corresponds to the specific allele. The allele specific probe can be provided in a number corresponding to the number of different alleles expected. The result is that one SNP can be characterised by the combination of one type of probe with four other type (allele-specific) probes, identifying all four theoretically possible alleles (one for A, T, C, and G), by incorporating identifier sequences of different lengths (preferred) or different labels into the allele specific probes.

In certain embodiments, the compound primer can be designed such that it spans the ligation point and thus identifies the allele of the SNP.

In a particular embodiment, preferably directed to the identification of single nucleotide polymorphisms, the first oligonucleotide probe of the set according to the invention is directed to a part of the target sequence that does not contain the polymorphic site and the second oligonucleotide probe of the pair according to the invention contains, preferably at the end distal from the primer-binding section, one or more nucleotide(s) complementary to the polymorphic site of interest. After ligation of the adjacent probes, the connected probe is specific for one of the alleles of a single nucleotide polymorphism. To identify the allele of polymorphic site in the target sequence, a pair of oligonucleotide probes can be provided wherein one first probe is provided and one or more second probes (in this case the pair of probes may contain more than two probes). Each second probe then contains a specific nucleotide at the end of the complementary sequence, preferably the 3'-end, in combination with a known length of the identifier. For instance, in case of an A/C polymorphism, the second probe can contain a specific nucleotide T in combination with a identifier length of 2 nucleotides and another second probe for this polymorphism combines a specific nucleotide G with a identifier length of 0. As the primers and the complementary parts of the compound primer are preferably the same length, this creates a length difference of the resulting amplicons of 2 nucleotides. In case the presence and/or the absence of all four theoretically possible nucleotides of the polymorphic site is desired, the identifier-specific nucleotide combination can be adapted accordingly. In this embodiment, it can be considered that the locus-specific information is coupled to the length of the identifier in the compound primer and the allele-specific information of the polymorphic site is coupled to the length of the second identifier. The combined length of the two identifiers can then be seen as indicative of the locus-allele combination. In a sample containing multiple target sequences, amplified with the same set of amplification-primers (and hence label) or with multiple sets of amplifications primers with labels that have overlapping emission spectra, the combined identifier lengths are chosen such that all elongated compound primers are of a unique length. In a preferred embodiment this principle can be extended to at least ten loci with at least two alleles per locus. A further advantage of using two identifiers, one in the second probe and one in the compound primer, is that by incorporating the majority of the length of the identifier in the compound primer (i.e. the locus-specific probe) the allele-specific probes can remain shorter i.e. the minimum number of bases sufficient for discrimination between the allele specific probes, which saves costs. The incorporation of the complete identifier sequence in the allele specific probe would require the synthesis of the majority of the identifier sequence twice.

Detection of Specific Target Sequence

The target sequence contains a known nucleotide sequence derived from a genome. Such a sequence does not necessarily contain a polymorphism, but is for instance specific for a gene, a promoter, an introgression segment or a transgene or contains information regarding a production trait, disease resistance, yield, hybrid vigour, is indicative of tumours or other diseases and/or gene function in humans, animals and plants. To this end, the complementary parts of the first probe and the second probe are designed to correspond to a, preferably unique, target sequence in genome, associated with the desired information. The complementary parts in the target sequence are located adjacent to each other. In case the desired target sequence is present in the sample, the two probes will anneal adjacently and after, ligation annealing and elongation of the compound primer and amplification can be detected.

Detection of AFLP Markers

AFLP, its application and technology is described in Vos et al., Nucleic Acids Research, vol. 23, (1995), 4407-4414 as well as in EP-A 0 534 858 and U.S. Pat. No. 6,045,994, all incorporated herein by reference. For a further description of AFLP, its advantages, its embodiments, its techniques, enzymes, adapters, primers and further compounds, tools and definitions used, explicit reference is made to the relevant passages of the publications mentioned hereinbefore relating to AFLP. AFLP and its related technology is a powerful DNA fingerprinting technique for the identification of for instance specific genetic markers (so-called AFLP-markers), which can be indicative of the presence of certain genes or genetic traits or can in general be used for comparing DNA, cDNA or RNA samples of known origin or restriction pattern. AFLP-markers are in general associated with the presence of polymorphic sites in a nucleotide sequence to be analysed. Such a polymorphism can be present in the restriction site, in the selective nucleotides, for instance in the form of indels or substitutions or in the rest of the restriction fragment, for instance in the form of indels or substitutions. Once an AFLP marker is identified as such, the polymorphism associated with the AFLP-marker can be identified and probes can be developed for use in the ligation assay of the present invention.

In another aspect the present invention pertains to a first nucleic acid probe comprising and preferably consisting of a part that is capable of hybridising to a first part of a target sequence. The invention also pertains to a second nucleic acid probe comprising a part that is capable of hybridising to a second part of the target sequence, and preferably comprising a primer-binding sequence and/or an identifier. The invention also pertains to a pair of probes, preferably comprising a first and second probe. The invention further pertains to a compound primer comprising a section that is capable of annealing to part of the first probe and preferably comprising a primer-binding sequence and/or an identifier. The invention also pertains to a set of probes, preferably comprising a compound primer, a first and second probe.

The invention in a further aspect pertains to the use of a pair or a set of probes in the analysis of at least one nucleotide sequence and preferably in the detection of a single nucleotide polymorphism, wherein the pair or set further comprises at least one additional probe that contains a nucleotide that is complementary to the known SNP allele. Preferably the pair or set comprises a probe for each allele of a specific single nucleotide polymorphism. The use of a pair or set of probes is further preferred in a method for the high throughput detection of single nucleotide polymorphisms wherein the length of the first identifier in the first probe is specific for a locus of a single nucleotide polymorphism and the length or the presence of the second identifier in the second probe is specific for an allele of the single nucleotide polymorphism.

Another aspect of the invention relates to the primers and more in particular to the set of primers comprising a first primer and one or more second primers, wherein each second primer contains a label and which second primer comprises a nucleotide sequence that is specific for said label.

The present invention also finds embodiments in the form of kits. Kits according to the invention are for instance kits comprising (pairs of or sets of) probes suitable for use in the method as well as a kit comprising primers or sets of primers, further a combination kit, comprising primers and probes, preferably all suitably equipped with enzymes buffers etcetera, is provided by the present invention.

The invention also relates to the use of a pair or sets of probes or two or more pairs or sets of probes according to the invention in the detection or determination of the presence, absence or amount of a target sequence in at least one sample.

DESCRIPTION OF THE FIGURES

FIG. 6: Schematic representation of structure and functionality of probes of the present invention, including the clamp sections. The probes (P1, P2) each contain a target specific section (T1, T2) complementary to a section (S1, S2) of the target sequence (D). The probes each contain a clamp section (C1, C2) capable of hybridising to each other. One of the probes contains a first primer binding section (Pr1) capable of hybridising to a primer. The probes can be hybridised against the target sequence. When the probes are hybridised adjacent on the target sequence, the probes can be ligated together with a ligase. The clamp may be denatured after which the compound primer (CP) comprising a second primer binding section (Pr2) that can be annealed to the connected probes. The compound probe can be elongated along the connected probe and the elongated connected probe can be amplified or multiplied, for instance using PCR or another suitable amplification technique, using one or more primers that can initiate amplification from Pr1 or Pr2 in the elongated compound probe. After amplification, the ligated and amplified probes can be detected.

FIG. 7A: Schematic and generalized representation of an SNP-specific or allele-specific oligonucleotide ligation assay wherein the allele-specific nucleotide is provided in the probe that contains the further (extended) region and wherein a cleavage structure is formed with i) the nucleotide in the target sequence that is located adjacent to the SNP to be investigated, ii) the nucleotide of the probe that hybridizes to the nucleotide of i), and iii) the nucleotide of the other probe that is located in the further (extended) region and adjacent to the allele-specific nucleotide in the probe. In this embodiment the cleavage structure is formed adjacent to the SNP. This improves specificity.

FIG. 7B: schematic representation of two allele specific or SNP-specific oligonucleotide ligation assays, wherein in the first assay the cleavage structure is formed by the nucleotides located adjacent to the SNP to be investigated, depicted as N, and wherein the second assay the cleavage structure is formed by the nucleotides of the SNP to be investigated, depicted as A or T.

FIG. 8: demonstrates the general applicability of the embodiment of FIGS. 7A and 7B for OLA assays in general, i.e. when using linear probes (1), circularizable/padlock probes (2), semi-circularizable/Keylock probes (3) and the combination of first and second probes and the compound primer of the present invention.

EXAMPLES

Figure 1:
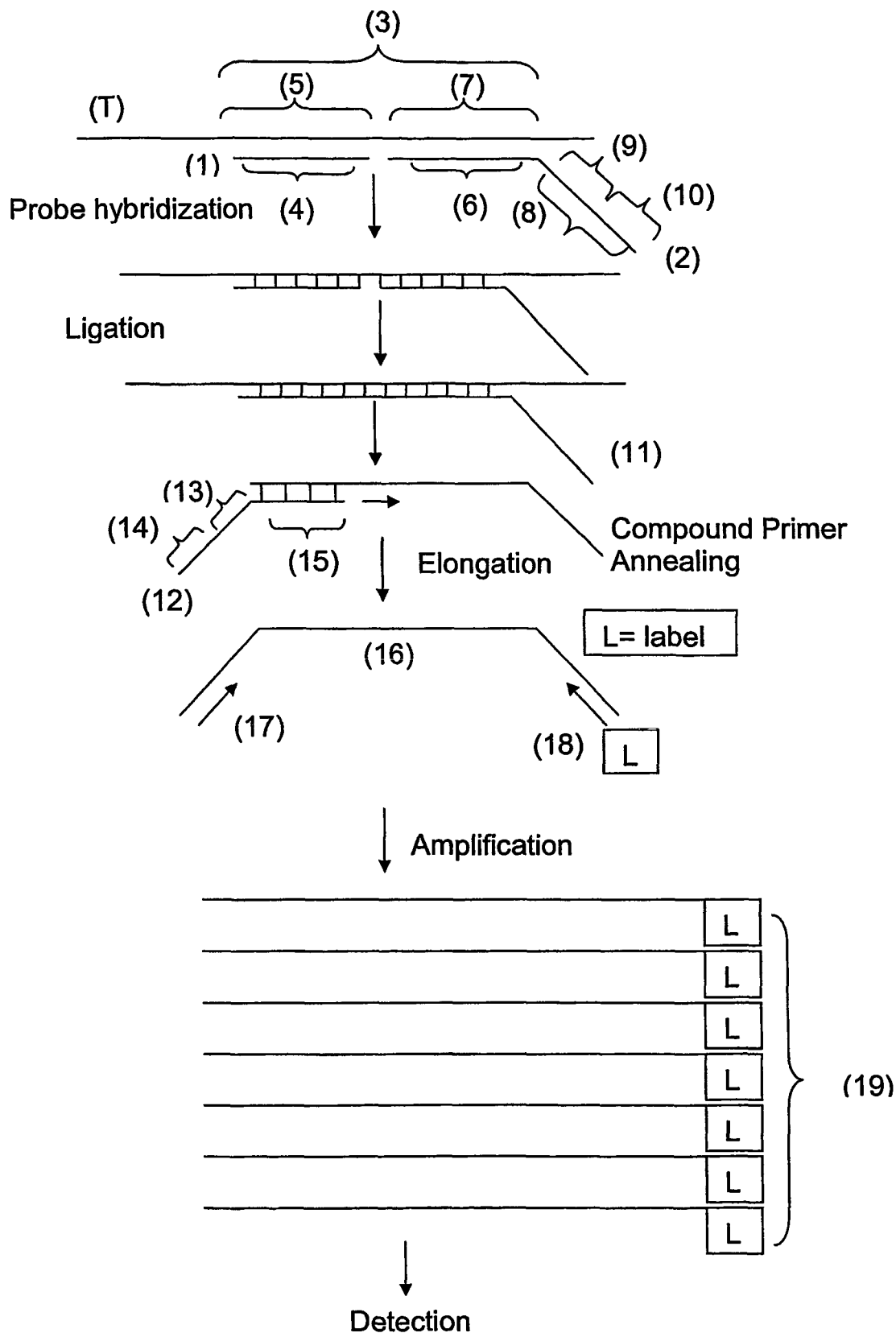
FIG. 1: A schematic representation of the method of the invention. A target sequence (T) in a sample is brought into hybridising contact with a first probe (1) and a second probe (2). The first probe contains a first target specific section (4) that is complementary to a first part of the target sequence (5). The second probe comprises s second target specific section (6) that is complementary to a second part of the target sequence (7). The second probe further comprises a tag section (8) comprising a first primer binding sequence (10). Optionally, the tag section comprises an identifier sequence (9) located between the primer binding sequence and the second target specific section. A compound primer (12) is provided, comprising a section that is complementary to at least part of the first target specific section (15) and further comprises a second primer binding section (14) and optionally a second identifiers section (13). When the probes are ligated to form a connected probe (11), the compound primer (12) is brought into hybridising contact with the connected probe, preferably after denaturing the duplex of the connected probe and the target sequence. The hybridised compound primer is elongated suing a polymerase and dNTPs to form an elongated compound primer (16). The elongated compound primer is subsequently contact with the primers set (17), (18) and amplified to provide amplicons (19) that can be detected.
Figure 2A:
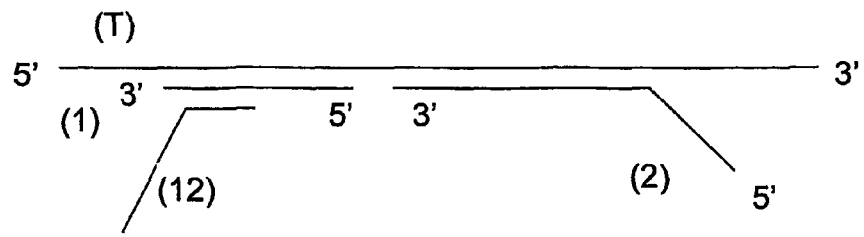
FIG. 2: A schematic representation of the embodiments wherein the compound primer is elongated at its 3' end.
Figure 3A:
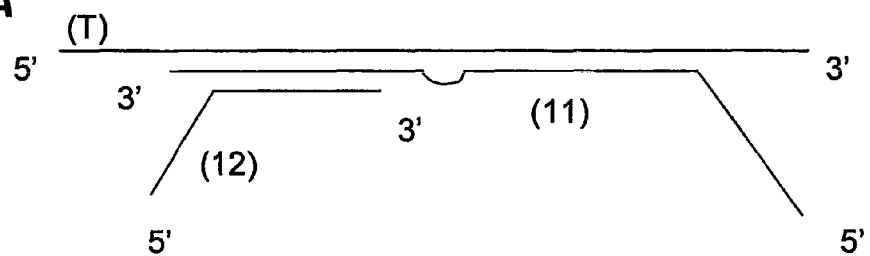
FIGS. 3A and 3B: A schematic representation of an embodiment wherein the compound primer anneals to the first probe and an embodiment wherein the compound primer anneals across the ligation point of the first and second probe, creating an extra discrimination step.
Figure 3B:
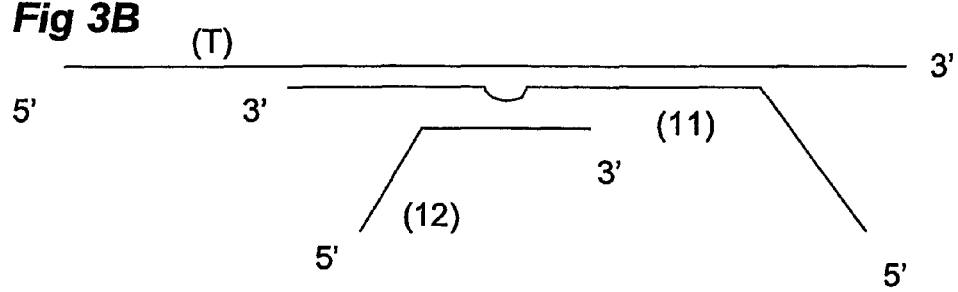
Figure 4A:
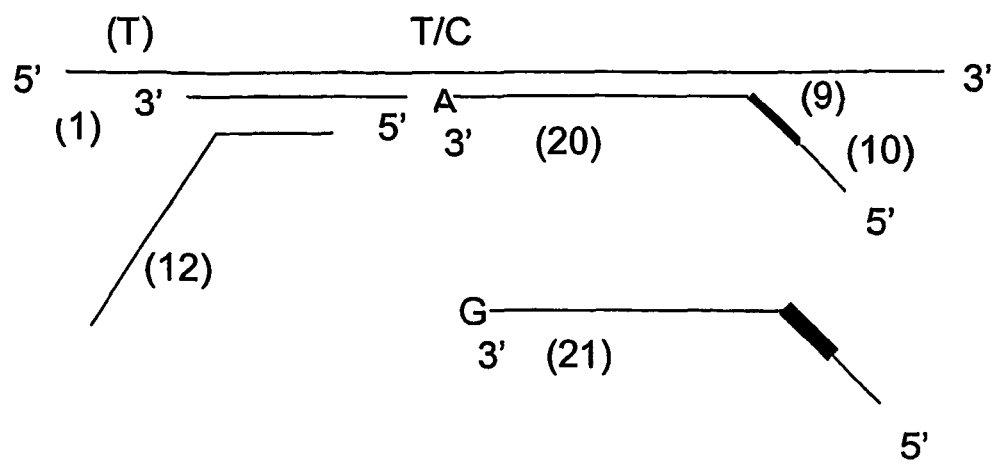
FIG. 4A: shows the embodiment wherein two second probes are provided each with an allele specific nucleotide at the 3' end of the probe to provide for allele specific discrimination.
Figure 4B:
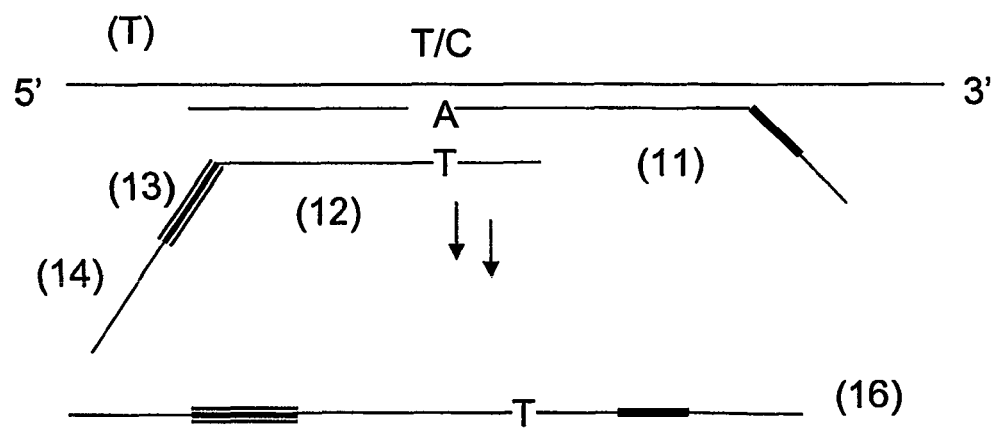
FIG. 4B: shows the embodiment wherein the compound primer comprises a second identifier sequence such that the presence of the target sequence is determined by the presence of both identifiers in the amplicon.

The invention is now illustrated by means of the following examples. Suitable experimental conditions, in particular relating to ligation, amplification and detection conditions can also be found in WO 03/052140, WO 03/052141, WO 03/052142 and WO 03/30163.

Example 1

Description of Biological Materials and DNA Isolation

DNA was isolated from leaf material of 4 homozygous tomato lines using methods known per se, for instance essentially as described in EP 0 534 858, and stored in 1×TE (10 mM Tris-HCl pH 8.0 containing 1 mM EDTA) solution. Concentrations were determined by UV measurements in a spectrophotometer (MERK) using standard procedures, and adjusted to 100 ng/µl using 1×TE.

Example 2

Identification of SNPs

The selected SNPs are identified and summarised in Table 1.

Example 3

Oligonucleotide Probe Design for Oligonucleotide Ligation Reaction

The oligonucleotide probes (5'-3' orientation) were selected to discriminate the SNP alleles for each of the SNP loci described in Example 2. All the probes are phosphorylated at the 5' end. The sequences are summarised in Table 2A and 2B. One group of first probes contains thioate linkages to render the probes exonuclease resistant (indicated in bold, the three most 3' nucleotides, Table 2A). Another group of first probes is biotinylated at the 3' end (Table 2B).

The second probes are provided in both allele specific forms and with an identifier (indicated in bold) generating a length difference of two nucleotides between two alleles for one locus (Table 3).

Example 4

Oligonucleotide Compound Primer Design for Annealing to the First Probe and Subsequent Compound Primer Elongation Reaction The compound primers (5'-3' orientation) were selected to hybridise to the first probes described in Example 3. PCR binding regions are underlined, first probe specific sequences are double underlined. The sequences are summarised in Table 3.

Example 5

Design of the PCR Amplification Primers

The sequence of one of the primers used for PCR amplification was complementary to the PCR primer binding regions incorporated in the compound primer described in Example 4. The sequence of the second PCR primer matched the PCR primer binding region of the second probe in example 3. Usually the forward primer is labelled. The concentration of the oligonucleotides was adjusted to 50 ng/μl. The sequence of the primers in 5'-3' orientation is depicted in Table 4.

TABLE 5

PCR amplification primers

| SEQ ID # | | Primer nr 5'-3' | | |
|---|---|---|---|---|
| 1 | MseI + 0: | 93E40 | GATGAGTCCTGAGTAA* | M00k |
| 2 | EcoRI + 0 | 93L01 | GACTGCGTACCAATTC* | E00k |

*Multiple labels possible

Example 6

Ligation and Amplification 4 samples (samples 14) of homozygous tomato lines (Example 1) were subjected to a multiplex oligonucleotide ligation reaction using a mixture of 20 probes (2 probes per locus). Conditions used were 1×Taq DNA ligase buffer (NEB), 0.2 U/μl Taq DNA ligase, and 0.05 fmol/μl of each probe in a volume of 10 μl. Ligation was performed in a thermocycler (Perkin Elmer) with the following cycling conditions: 2 minutes at 94° C.+10*(15 seconds at 94° C.+60 minutes at 60° C.)+4° C. continuously. Following ligation, the 10 μl ligation product was diluted with 30 μl 1×Taq DNA ligase buffer.

Ten μl of the diluted ligation reactions was used to perform a PCR using a labelled E00k primer combined with M00k. The E00k primer was labelled with JOE to enable detection on the MegaBACE. The compound primer was added simultaneously with the amplification primers. Conditions used in the PCR were 30 pg of each compound primer, 30 ng labelled E00k primer and 30 ng M00k primer, 1× Accuprime buffer I, 0.4 ul Accuprime polymerase (Invitrogen) on 10 μl diluted ligation product in a 20 μl PCR reaction. PCR was performed in a thermocycler with the following cycling conditions:

For compound primer elongation: 15 seconds at 94° C.+30 seconds at 56° C.+2 minutes at 68° C., for amplification followed by: 2 minutes at 94° C.+35*(15 seconds at 94° C.+30 seconds at 56° C.+60 seconds at 68° C.)+4° C. continuously.

PCR product was purified using Sephadex 50 and diluted 80 times with MQ. Diluted PCR product was analysed on the MegaBACE.
Buffer Compositions:
1×Taq DNA ligase buffer
20 mM Tris-HCl
10 mM potassium acetate
10 mM Magnesium acetate
10 mM DTT
1 mM NAD
0.1% Triton X-100
(pH 7.6@ 25° C.)
1× AccuPrime Taq DNA polymerase buffer
20 mM Tris-HCl (pH8.4)
50 mM KCl
1.5 mM MgCl$_2$
0.2 mM dGTP, DATP, dTTP and dCTP
thermostable AccuPrime™ protein
10% glycerol.

Example 7

Purification and Dilution of Amplicons

In case of detection using the MegaBACE 1000 capillary sequencing instrument, desalting and purification of the PCR reactions mixtures was carried in 96-well format, using the following procedure:

Dry Sephadex™ G-50 superfine (Amersham Pharmacia Biotech, Uppsala, Sweden) was loaded into the wells of a 96-well plate (MultiScreen®-HV, Millipore Corporation, Bedford, Mass., USA), using the 45 microliter column loader (Millipore Corporation) as follows: Sephadex™ G-50 superfine was added to the column loader.

Excess Sephadex™ was removed from the top of the column loader with a scraper. The Multiscreen-HV plate was placed upside-down on top of the Column Loader. The Multiscreen-HV plate and the Column Loader were both inverted. The Sephadex™ G-50 was released by tapping on top or at the side of the Column Loader. Next, the Sephadex™ G-50 was swollen en rinsed as follows: 200 μl Milli-Q water was added per well using a multi-channel pipettor. A centrifuge alignment frame was placed on top of a standard 96-well microplate, the Multiscreen-HV plate was place on top and the minicolumns were packed by centrifugation for 5 min at 900 g.

The 96-well plate was emptied and placed back. Steps 5-7 were repeated once.

200 μl Milli-Q water (MQ) was added to each well to swell the Sephadex™ G-50 and incubated for 2-3 hours. Occasionally, at this stage the Multiscreen-HV plates with swollen mini-columns of Sephadex™ G-50 superfine were tightly sealed with parafilm and stored a refrigerator at 4° C. until further use. A centrifuge alignment frame was placed on top of a standard 96-well microplate, the Multiscreen-HV plate was placed on top of the assembly and the minicolumns were packed by centrifugation for 5 min at 900 g. The 96-well microplate was removed. The mixtures containing the amplicons were carefully added to the centre of each well. Using the centrifuge alignment frame, the Multiscreen-HV plate was placed on top of a new standard U-bottom microtitre plate and centrifugation was carried out for 5 min at 900 g. The eluate in the standard 96-well plate (approximately 25 μl per well) contains the purified product. Purified samples were diluted 25-75 fold in Milli-Q water before injection.

Example 8

Capillary Electrophoresis on the MegaBACE

Preparation of the Samples:
A 800-fold dilution of ET-900 Rox size standard (Amersham Biosciences) was made in water. 8 μl diluted ET-900 Rox was added to 2 μl purified sample. Prior to running, the sample containing the sizing standard was heat denatured by incubation for 1 min at 94° C. and subsequently put on ice.
Detection on the MegaBACE:
MegaBACE capillaries were filled with 1×LPA matrix (Amersham Biosciences, Piscataway, N.J., USA) according to the manufacturer's instructions. Parameters for electrokinetic injection of the samples were as follows: 45 sec at 3 kV. The run parameters were 110 min at 10 kV. Post-running, the cross-talk correction, smoothing of the peaks and cross-talk correction was carried out using Genetic Profiler software, version 1.0 build 20001017 (Molecular Dynamics, Sunnyvale, Calif., USA), and electropherograms generated.

Example 9

The probes of the present invention were tested and compared to another type of probes that has recently been developed and found to be superior over convention linear or padlock probes. This type of probe is the subject of a separate patent application filed on Jun. 17, 2004 as PCT/NL03/00444, the contents of which are incorporated herein by reference. The probes, depicted as 'Keylocks' are also provided in this application in Table 5. The probes of the present invention were split in three sets, set 1 containing all 10 compound probes (Table 4, locus 3140), Set 2 containing 5 compound probes (Table 4, locus 31, 33, 35, 37, 39), and set 3 containing the 5 other compound probes (Table 4, locus 32, 34, 36, 38, 40), Two samples of the homozygous tomato lines (Example 1) were subjected to a multiplex oligonucleotide ligation reaction using a mixture of 20 probes (2 probes per locus). Conditions used were 100 ng DNA, 1×Taq DNA ligase buffer (NEB), 0.2 U/µl Taq DNA ligase, and 0.5 fmol/µl of each probe in a volume of 10 µl. Ligation was performed in a thermocycler (Perkin Elmer) with the following cycling conditions: 2 minutes at 94° C.+10*(15 seconds at 94° C.+60 minutes at 60° C.)+4° C. continuously. Following ligation, the 10 µl ligation product was diluted with 30 µl 1×Taq DNA ligase buffer.

Ten µl of the diluted ligation reactions was used to perform a PCR using a labelled E00k primer combined with M00k. The E00k primer was labelled with FAM to enable detection on the MegaBACE. The compound primer was added simultaneously with the amplification primers. Conditions used in the PCR were 5 µl of 50 fmol/µl of each compound primer, 0.6 µl of 50 ng/µl labelled E00k primer and 0.6 µl of 50 ng/µl M00k primer, 2 µl 10×Taq buffer I, 0.08 µl 5 U/µl Amplitaq Gold polymerase on 10 µl diluted ligation product in a 20 µl PCR reaction. PCR was performed in a thermocycler with the following cycling conditions:
For compound primer elongation: 12 minutes at 94° C.+10* (15 seconds at 94° C.+2 minutes at 60° C.+1 minutes at 72° C.), for amplification followed by: 35*(15 seconds at 94° C.+30 seconds at 56° C.+60 seconds at 72° C.)+4° C. continuously.

The 'Keylock' probes were subjected to the same reactions conditions and the same ligation/amplification protocol but without the addition of compound probes Blanks containing only MQ water were also run.

Figure 5:
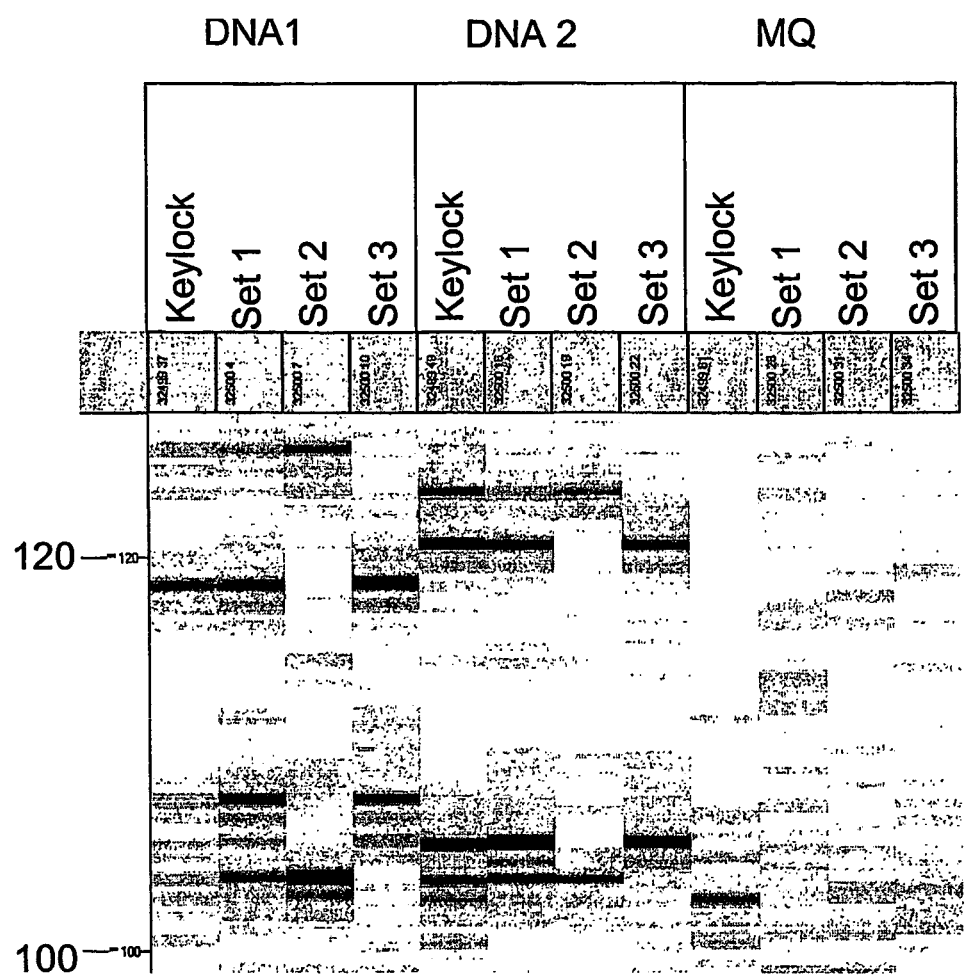
FIG. 5: Pseudogel-image of the probe sets of the present invention compared to semi-circularizable probes for comparison based on two different samples of DNA, using probe sets 1-3 and against MQ water as reference.

PCR product was purified using Sephadex 50 and diluted 80 times with MQ. Diluted PCR product was analysed on the MegaBACE. The results are presented in FIG. 5. The use of the compound probes resulted in the detection desired products, compared to the Keylock probes. It was also observed that the compound probes of the present invention resulted in less side-products compared to the Keylock probes.

Example 10

Keylock Probes Using Cleavase Approach

To demonstrate the feasibility of the cleavase-ligation approach, the probes from Table 2A, (SEQ ID #) were extended at their 5' end with a further region having the sequence 'CACAC'. The extended probes were combined with the second probes of Table 3 and subjected to the above described hybridization and ligation protocol wherein the enzymes (both ligase and Cleavase (obtained from Third Wave Inc. and used 'as is' in amounts varying between 1 and 10 microliter)) are added. The resulting mixture is incubated in a thermocycler (Perkin Elmer) with the following cycling conditions: 4 minutes at 94° C.+240 minutes at 60° C.+4° C. continuously. Subsequently, the mixture is amplified under the conditions as described in Example 6. The expected products were found, i.e. ligated probes with lengths corresponding to the results obtained with the second probes of Table 3 that were not extended, indicating that the cleavase step and the ligations step were successful, indicating that the method works. Experiments were performed in absence of (combinations of) enzymes. These experiments demonstrated that both enzymes are necessary for this probe type to come to a ligated probe.

TABLE 1

Selected SNP sequences and position of the SNP

| SEQ ID # | Locus nr. | Length | SNP position | SEQUENCE W = A or T; M = A or C; R = A or G; Y = C or T; K = G or T; S = G or C; H = A, C or T; B = C, G or T; V = A, C or G; D = A, G or T; N = A, C, G or T |
|---|---|---|---|---|
| 3 | 31 | 472 | 246 | TATCCACTCAGGTCTCCGCAAGCC AGAAATGGGATATACACCTTGTTA CGACCYTCAAGCCATCCACTACTG CAATCTGTCATGTCACAGATGTTC GGAAGATAATGTATAAGTACAACT ATATAGTCGGAWTTGCATCTAGTC TAGCATTCGGAAAATGGAAGCCAT GCTACTTCTAGCATAAAAAACAGC AGCTAGAAATCGTAACTCCAATGA TACGAGGAAGTATTCAGAGTTTAG AGTGAWGTACAATGCAATTTAGAG AACAAGCATCTGCACATCTAAGTT ACCTAGGTCCTCAGCGCCTGATGG ACTTCCAACTTGTTCAAGAAGGCG ATAAAGGTCTTTCTCATTGAATCC TTCAGGTGGAGAGTAGTTTTCACA AACTGCAAATGCCTCTGCACAGCG GAAAGATTGAATTAGATTTATGTT ATATAGCCATTCTAGTCTTGCTTT AATGGATCTTTCTCGA |
| 4 | 32 | 222 | 175 | CCACAGTTTCATGCTGCACCTACA TGTGTAAGCAACTATCATAGCAAG TCTCGGAACAATTGGTAGGAAAAA ATCMYKTAAGGATATGAAACATAC TGTYCTTTCTTCATCTGAGTCTGY AGAGTTAATTTTTAACTCTTGGGA TAAATGCAAAGAWTTAGACATGGA KGAGTYCTTAACACGTCCAGACAA GAGGCGTAACACAGGTACACCTTT TCTCGA |
| 5 | 33 | 133 | 116 | TTGTGCTTGATGAATTGTAGGTCC AGTGCAGGTTTGCTTCTAAAACAG GGAGCACTTTGCAAGTGGTGAAAG TTCTATTAGCTGGGAAAGTGTAGT TTGAGCAGTTTTGAGCTGARTTAA CAAGAAAAATCGA |
| 6 | 34 | 250 | 47 | CCGCCACTGGGTAATTGAGTTTCA TATTGATGGTTTTGTTTTTGTTRA CGCTTCTTCCTTGTTGAGAGGGTT CAATGGAGAGATTCTATCTCGTCC TCCATTAGTTGAAGCTATTGCCTT TGATCCTATCCTTTCAAAGGYCAA GATGATTGCAGATAATTGGAATCC ATTAACCAATGATTCTACGGAAAA TTTATTCCCTCACTGGAGGAGATG GGCAGAGATAAATATGAGATTTTG TGATGACAT |

TABLE 1-continued

Selected SNP sequences and position of the SNP

SEQUENCE
W = A or T; M = A or C;
R = A or G; Y = C or T;
K = G or T; S = G or C;
H = A, C or T; B = C, G or T; V = A, C or G;
D = A, G or T; N = A, C, G or T

| SEQ ID # | Locus nr. | Length | SNP position | Sequence |
|---|---|---|---|---|
| 7 | 35 | 284 | 84 | TCGAGTAAGGCGGATGGATATGGA ACAAGCCATTTCAAGGAGCAATTT CCCAGGATTTTCAGCTTTGCAACA GCAGAAGTGTAYCTCTGCAGAGAT AGATCATAACCTTTGGAAAGGTGT AGTAATTGTCAAAGGGAGGAATGA GCCAGGAAACTGATAGACTATGTT GCGAAAATAAGCTATACTTCACTA AAAAAAGGCTAGACGTTTGAGAAA TGAAGCAAGAACTAACACCTCTCA CCAATTGCATCATTTTCTTAGTTC AGTTGATGTGATGAGCTTGT |
| 8 | 36 | 320 | 31 | TCGATATCCWCTCTTGTTTGTTGC AGGAGCWGAACTATAAATTGCTTG CAGGAACCTTGACATATGCTTTCT GTTGAGCTTGAATCACCAGCATG GATTTGAATGCCTTGCCACAGCCA GAGGATGACGAYGAGATTTTGGA CAACAATTAGAAGATGAACCACAA GAACCTATTTTACGTAGTGATGAG CSTGCAGATTATGTCACGAGTGCT GTAGAGATTTCACGTCGCGTATGT TTCTGCTTATACTGCTCGCTGTAT CAACTATTGAACYGTACTACTACT TGARCTTGCTCGTTTATTGGATAT TTCTTTTT |
| 9 | 37 | 193 | 159 | GAATTCACACTASGTTCGATGAAA TTGAAACGTTCTCTTTCTGAAGAA KATACACAAGAAAAAATCTTATAG TCCTCAACAATATTCTTCTTCGTA ACAGAAAACACGGAAGAAAATCTC TTCTGAAAATCCCTATAATCACTG GCTGGAACTTCTCCSAACTCTCAA TTTTTTCAACCTTCTCTATGTTAA |
| 10 | 38 | 291 | 89 | CTGCAGAADTACTGTTTGTTCAGG ACTTACTAAATATCCTAAACAAAA TTGATGATAGAGCCAATAATGTAT GCATGATTGGCGGTCCRTTCTTTT GTTATAGCAAGAGCTTGAAGCTAA TTTTGTTTGTCATAATGGCCGCAC TAATTGTTATTATCTCAGAATGA ACAAAAAGAAGCAAGTCAGAAGCT TTSTACTCTATACTGAACAACTTT GGAATTGGAACTATGTACTTATCT AGCCACGCCTCATAGATCTTTGTG GTTTAGGAGTGTTAA |
| 11 | 39 | 337 | 122 | GAATTCACAATGAAAAAKGKDGTA AAAACACGAAATCAATCAAGCATG CAAGAGATAATGTTGTCCATCCAG TTGTTGTTGATGTTTCGGTATTGT ATGTGTGTTGGGAGGAGTTATCTG GRCAGCAAGTCGAGGTTTGAACGT CAAAAAGGTATGGTTGTCTTCTC TCTTTGTCCCTTTTCGAAGAGACC CCTAAGGTTCAGACGAATCTATTC CAAAAACTAGGGTTGTTCCTTGTT GCATCTCCTTKTCACAAGCTCCCA TCGCATCATAAGTAGGGTATGTTT GATGGTAGAATTTACGGATGTAAT TTACTTTTGAAATGATTATGTTAA |
| 12 | 37 | 373 | 63 | AGAGAGACGAGAGCTCGACTAGTG ATAGTGTTATGTGCAACAGTTGAA TAGAAAGATGYACACGAGCCTCGG ATCAATGGCAGGGAAAGAGGCGTG GTGCTACGAACCATAAAGGCAAGG TTGAGCTTTCCTTTACAGAGTACA TCGCCTATTCCATACTCCGCTGAT ACTCTTTGATAAATCAAAATCTGT GGTGATCTCGTAGTTCTTGGGGAT CCCAGCCAAAACCACCTTCGAGGT TCAACACAACATAGACAGTATGGC AGAATATCAAGACAATGACTGCTC GAAACTGCTGATGGCATTATGTGC AACCGTTGAATAGAGAGATGTACA CGAGTCTCGGATCAATGGCAGGAA AAGAGAGTGCTTG |

TABLE 2A

Oligonucleotide first probes with thioate linkages for detection of SNPs from Table 1.

| SEQ ID # | Locus nr. | 5'-PH-3' |
|---|---|---|
| 13 | 31 | GTACAATGCAATTTAGAGAACAAGCCCGGGCGGCCCGGG CGCGGC |
| 14 | 32 | CTTAACACGTCCAGACAAGAGGCCGCGGGCGCGCGGCGG GCGG |
| 15 | 33 | TTAACAAGAAAAATCGGTCAGGACTCGCGGCGCCCGCGG CGCGGG |
| 16 | 34 | ACGCTTCTTCCTTGTTGAGAGGGCGCCGGCCGGGCCCGC CGGC |
| 17 | 35 | CTCTGCAGAGATAGATCATAACCTGGCCCGCGCGCCCGG CGGCG |
| 18 | 36 | GAACTATAAATTGCTTGCAGGAACCGGGCGGCCCGGCCC GCCCGG |
| 19 | 37 | AACTCTCAATTTTTCAACCTTCTCTACGCGCCGGGCCGC GGCCGGC |
| 20 | 38 | TTCTTTTGTTATAGCAAGAGCTTGAAGCCGGCCGGCCGC GCGCGGG |
| 21 | 39 | TCACAAGCTCCCATCGCATCATCGGCGCGCGGGCCGCGC GCC |
| 22 | 40 | ACACGAGCCTCGGATCAATGCGGCCCGCCCGGCGGCCGC C |

TABLE 2B

Oligonucleotide fist probes (biotinylated) for detection of SNPs from Table 1.

| SEQ ID # | Locus nr. | 5'-PH-3' |
|---|---|---|
| 23 | 31 | GTACAATGCAATTTAGAGAACAAGCCCGGGCGGCCCGGG CGCGGC |

TABLE 2B-continued

Oligonucleotide fist probes (biotinylated) for detection of SNPs from Table 1.

| SEQ ID # | Locus nr. | 5'-PH-3' |
|---|---|---|
| 24 | 32 | CTTAACACGTCCAGACAAGAGGCCGCGGGCGCGCGGCGGGCGG |
| 25 | 33 | TTAACAAGAAAAATCGGTCAGGACTCGCGGCGCCCGCGGCGCGGG |
| 26 | 34 | ACGCTTCTTCCTTGTTGAGAGGGCGCCGGCCGGGCCCGCCGGC |
| 27 | 35 | CTCTGCAGAGATAGATCATAACCTGGCCCGCGCGCCCGGCGGCG |
| 28 | 36 | GAACTATAAATTGCTTGCAGGAACCGGGCGGCCCGGCCCGCCCGG |
| 29 | 37 | AACTCTCAATTTTTCAACCTTCTCTACGCGCCGGGCCGCGGCCGGC |
| 30 | 38 | TTCTTTTGTTATAGCAAGAGCTTGAAGCCGGCCGGCCGCGCGCGGG |
| 31 | 39 | TCACAAGCTCCCATCGCATCATCGGCGCGCGGGCCGCGCGCC |
| 32 | 40 | ACACGAGCCTCGGATCAATGCGGCCCGCCCGGCGGCCGCC |

TABLE 3

Oligonucleotide second probes for detection of SNPs from Table 1.

| SEQ ID # | Locus nr. | 5'(PH)-3' |
|---|---|---|
| 33 | 31 | GCCGCGCCCGGGCCGCCCGGGATGAGTCCTGAGTAACGCTGGAAGTATTCAGAGTTTAGAGTGAA |
| 34 |    | GCCGCGCCCGGGCCGCCCGGGATGAGTCCTGAGTAACGGGAAGTATTCAGAGTTTAGAGTGAT |
| 35 | 32 | CCGCCCGCCGCGCGCCCGCGGATGAGTCCTGAGTAACGCAGCAAAGAATTAGACATGGATGAGTT |
| 36 |    | CCGCCCGCCGCGCGCCCGCGGATGAGTCCTGAGTAACGCCAAAGATTTAGACATGGAGGAGTC |
| 37 | 33 | CCCGCGCCGCGGGCGCCGCGGATGAGTCCTGAGTAACGCCTAGTTTGAGCAGTTTTGAGCTGAA |
| 38 |    | CCCGCGCCGCGGGCGCCGCGGATGAGTCCTGAGTAACGTAGTTTAGCAGTTTTGAGCTGAG |
| 39 | 34 | GCCGGCGGGCCCGGCCGGCGGATGAGTCCTGAGTAACGCCTTCATATTGATGGTTTTGTTTTGTTA |
| 40 |    | GCCGGCGGGCCCGGCCGGCGGATGAGTCCTGAGTAACGTTCATATTGATGGTTTTGTTTTGTTG |
| 41 | 35 | CGCCGCCGGGCGCGCGGGCCGATGAGTCCTGAGTAACGCAAGCTTTGCAACAGCAGAAGTGTAT |
| 42 |    | CGCCGCCGGGCGCGCGGGCCGATGAGTCCTGAGTAACGAGCTTTGCAACAGCAGAAGTGTAC |
| 43 | 36 | CCGGGCGGGCCGGGCCGCCCGATGAGTCCTGAGTAACGCTCTCTCTTGTTTTGTTGCAGGAGCA |
| 44 |    | CCGGGCGGGCCGGGCCGCCCGATGAGTCCTGAGTAACGCACTCTTGTTTGTTGCAGGAGCT |
| 45 | 37 | GCCGGCCGCCCGGCCGCGCGGATGAGTCCTGAGTAACGCGATCACTGGCTGAACTTCTCCC |
| 46 |    | GCCGGCCGCGGCCCGGCGCGGATGAGTCCTGAGTAACGATCACTGGCTGGAACTTCTCCG |

TABLE 3-continued

Oligonucleotide second probes for detection of SNPs from Table 1.

| SEQ ID # | Locus nr. | 5'(PH)-3' |
|---|---|---|
| 47 | 38 | CCCGCGCGCGGCCGGCCGGCGATGAGTCCTGAGTAACGCCATGTATGCATGATTGGCGGTCCA |
| 48 |    | CCCGCGCGCGGCCGGCCGGCGATGAGTCCTGAGTAACGATGTATGCATGATTGGCGGTCCG |
| 49 | 39 | GGCGCGCGGCCCGCGCGCCGGATGAGTCCTGAGTAACGCTGTTGTTCCTTGTTGCATCTCCTTT |
| 50 |    | GGCGCGCGGCCCGCGCGCCGGATGAGTCCTGAGTAACGGTTGTTCCTTGTTGCATCTCCTTG |
| 51 | 40 | GGCGGCCGCCGGGCGGGCCGGATGAGTCCTGAGTAACGTGCAACAGTTGAATAGAAAGATGT |
| 52 |    | GGCGGCCGCCGGGCGGGCCGGATGAGTCCTGAGTAACGCAACAGTTGAATAGAAAGATGC |

TABLE 4

Oligonucleotide compound primers for detection of SNPs from Table 1.

| SEQ ID # | Locus nr. | 5'(PH)-3' sequence |
|---|---|---|
| 53 | 31 | GACTGCGTACCAATTCCCCGATTACGATGCAGCTACGTCGATATCGATCGGATCGCTTGTTCTCTAAATTGCATTGTAC |
| 54 | 32 | GACTGCGTACCAATTCCCGACTCAGTGCTATACGGATCTACGTCGACATGGGCCTCTTGTCTGGACGTGTTAAG |
| 55 | 33 | GACTGCGTACCAATTCCCGATAGTCCGTAACGTTAGCATGCGTACAGTCCTGACCGATTTTCTTGTTAA |
| 56 | 34 | GACTGCGTACCAATTCCCCATGTCGATAGCCTGAGCATCCCCTCTCAACAAGGAAGAAGCGT |
| 57 | 35 | GACTGCGTACCAATTCCCATGCTCAGCATGACGTGAAGGTTATGATCTATCTCTGCAGAG |
| 58 | 36 | GACTGCGTACCAATTCCCCGTAACGTTAGCGGGTTCCTGCAAGCAATTTATAGTTC |
| 59 | 37 | GACTGCGTACCAATTCCCTCGAATGATAGAGAAGGTTGAAAAATTGAGAGTT |
| 60 | 38 | GACTGCGTACCAATTCCCCGTTCAAGCTCTTGCTATAACAAAAGAA |
| 61 | 39 | GACTGCGTACCAATTCCCATGATGCGATGGGAGCTTGTGA |
| 62 | 40 | GACTGCGTACCAATTCCCATTGATCCGAGGCTCGTGT |

TABLE 5

Oligonucleotide Keylock probes for detection of SNPs from Table 1.

| SEQ ID # | Locus nr. | Length (bp) | 5'(PH)-3' sequence |
|---|---|---|---|
| 63 | 31 | 124 | GCCGCGCCCGGGCCGCCCGGGATGAGTCCTGAGTAACGCTGGAAGTATTCAGAGTTTAGAGTGAA |
| 64 | 31 | 122 | GCCGCGCCCGGGCCGCCCGGGATGAGTCCTGAGTAACGGGAAGTATTCAGAGTTTAGAGTGAT |
| 65 | 31 | rev | GTACAATGCAATTTAGAGAACAAGCGATCCGA |

TABLE 5-continued

Oligonucleotide Keylock probes for detection of SNPs from Table 1.

| SEQ ID # | Locus nr. | Length (bp) | 5'(PH)-3' sequence |
|---|---|---|---|
| | | | TCGATATCGACGTAGCTGCATCGTAATCGGGG AATTGGTACGCAGTCCCGGGCGGCCCGGGCGC GGC |
| 66 | 32 | 119 | CCGCCCGCCGCGCGCCCGCGGATGAGTCCTGA GTAACGCAGCAAAGAATTAGACATGGATGAGT T |
| 67 | 32 | 117 | CCGCCCGCCGCGCGCCCGCGGATGAGTCCTGA GTAACGCCAAAGATTTAGACATGGAGGAGTC |
| 68 | 32 | rev | CTTAACACGTCCAGACAAGAGGCCCATGTCGA CGTAGATCCGTATAGCACTGAGTCGGGAATTG GTACGCAGTCCGCGGGCGCGCGGCGGGCGG |
| 69 | 33 | 114 | CCCGCGCCGCGGGCGCCGCGGATGAGTCCTGA GTAACGCCTAGTTTGAGCAGTTTTGAGCTGAA |
| 70 | 33 | 112 | CCCGCGCCGCGGGCGCCGCGGATGAGTCCTGA GTAACGTAGTTTGAGCAGTTTTGAGCTGAG |
| 71 | 33 | rev | TTAACAAGAAAAATCGGTCAGGACTGTACGCA TGCTAACGTTACGGACTATCGGGAATTGGTAC GCAGTCCGCGGCGCCCGCGGCGCGGG |
| 72 | 34 | 109 | GCCGGCGGGCCCGGCCGGCGGATGAGTCCTGA GTAACGCCTTCATATTGATGGTTTTGTTTTG TTA |
| 73 | 34 | 107 | GCCGGCGGGCCCGGCCGGCGGATGAGTCCTGA GTAACGTTCATATTGATGGTTTTGTTTTGTT G |
| 74 | 34 | rev | ACGCTTCTTCCTTGTTGAGAGGGGATGCTCAG GCTATCGACATGGGGAATTGGTACGCAGTCCG CCGGCCGGGCCCGCCGGC |
| 75 | 35 | 104 | CGCCGCCGGGCGCGCGGGCCGATGAGTCCTGA GTAACGCAAGCTTTGCAACAGCAGAAGTGTAT |
| 76 | 35 | 102 | CGCCGCCGGGCGCGCGGGCCGATGAGTCCTGA GTAACGAGCTTTGCAACAGCAGAAGTGTAC |
| 77 | 35 | rev | CTCTGCAGAGATAGATCATAACCTTCACGTCA TGCTGAGCATGGGAATTGGTACGCAGTCGGCC CGCGCGCCCGGCGGCG |
| 78 | 36 | 99 | CCGGGCGGGCCGGGCCGCCCGATGAGTCCTGA GTAACGCTCTCTCTTGTTTGTTGCAGGAGCA |
| 79 | 36 | 97 | CCGGGCGGGCCGGGCCGCCCGATGAGTCCTGA GTAACGCACTCTTGTTTGTTGCAGGAGCT |
| 80 | 36 | rev | GAACTATAAATTGCTTGCAGGAACCCGCTAAC GTTACGGGGAATTGGTACGCAGTCGGGCGGCC CGGCCCGCCCGG |
| 81 | 40 | 94 | GCCGGCCGCGGCCCGGCGCGGATGAGTCCTGA GTAACGCGATCACTGGCTGGAACTTCTCCC |
| 82 | 40 | 92 | GCCGGCCGCGGCCCGGCGCGGATGAGTCCTGA GTAACGATCACTGGCTGGAACTTCTCCG |
| 83 | 40 | rev | AACTCTCAATTTTTCAACCTTCTCTATCATTC GAGGGAATTGGTACGCAGTCCGCGCCGGGCCG CGGCCGGC |
| 84 | 38 | 89 | CCCGCGCGCGGCCGGCCGGCGATGAGTCCTGA GTAACGCCATGTATGCATGATTGGCGGTCCA |
| 85 | 38 | 87 | CCCGCGCGCGGCCGGCCGGCGATGAGTCCTGA GTAACGATGTATGCATGATTGGCGGTCCG |
| 86 | 38 | rev | TTCTTTTGTTATAGCAAGAGCTTGAACGGGGA ATTGGTACGCAGTCGCCGGCCGGCCGCGCGCG GG |
| 87 | 39 | 84 | GGCGCGCGGCCCGCGCGCCGGATGAGTCCTGA GTAACGCTGTTGTTCCTTGTTGCATCTCCTTT |
| 88 | 39 | 82 | GGCGCGCGGCCCGCGCGCCGGATGAGTCCTGA GTAACGGTTGTTCCTTGTTGCATCTCCTTG |
| 89 | 39 | rev | TCACAAGCTCCCATCGCATCATGGGAATTGGT ACGCAGTCCGGCGCGCGGGCCGCGCGCC |
| 90 | 37 | 79 | GGCGCCGCCGGGCGGGCCGATGAGTCCTGA GTAACGTGCAACAGTTGAATAGAAAGATGT |
| 91 | 37 | 77 | GGCGGCCGCCGGGCGGGCCGATGAGTCCTGA GTAACGCAACAGTTGAATAGAAAGATGC |
| 92 | 37 | rev | ACACGAGCCTCGGATCAATGGGAATTGGTACG CAGTCCGGCCCGCCCGGCGGCCGCC |

The invention claimed is:

1. A method for determining the presence, absence or amount of a target nucleotide sequence in a nucleic acid sample, the method comprising the steps of:
   a) providing to a nucleic acid sample a first probe for each target sequence to be detected in the sample, whereby the first probe has a first target specific section that is complementary to a first part of the target sequence and a second probe for each target sequence to be detected in the sample, whereby the second probe is different from the first probe and has a second target specific section that is complementary to a second part of the target sequence, whereby the first and second part of the target sequence are located adjacent to each other, and whereby the second probe further comprises a tag section that is essentially non-complementary to the target sequence, whereby the tag section comprises a first primer binding sequence;
   b) allowing the first and second target specific sections of the first and second probe to anneal to the first and second parts of each target sequence that is present in the sample whereby the first and second target specific sections of the probes are annealed adjacent on the target sequence;
   c) providing means for connecting the first and second target specific sections annealed adjacently to the target sequence and allowing the first and second target specific sections to be connected, to produce a connected probe corresponding to a target sequence in the sample;
   d) providing to the mixture resulting from step c) a compound primer that is different from both the first probe and the second probe and comprises a section that is complementary to at least part of the first target specific section and further comprises a second primer binding section;
   e) allowing the compound primer to anneal to at least part of the first target specific section;
   f) elongating the compound primer;
   g) providing a set of primers comprising a first primer having a sequence essentially identical to the first primer-binding section, and a second primer that is complementary to the second primer-binding section;
   h) amplifying the resulting mixture to produce an amplified sample comprising amplicons that are representations of the connected probes;
   i) determining the presence, absence or amount of a target sequence in the sample by detecting the presence, absence or amount of the corresponding amplicon.

2. The method according to claim 1, wherein the first, the second or the first and the second primer have a molar ratio to the compound primer that is between 10 and 1000.

3. The method according to claim 1, wherein the first and second primer are provided to the mixture resulting from step c) prior the elongation of the compound primer in step f).

4. The method according to claim 1, wherein the compound primer further comprises a section that is complementary to the second target specific section.

5. The method according to claim 1, wherein the primer binding sites are universal primer binding sites.

6. The method according to claim 1, wherein at least one of the first and second primers is a selective primer.

7. The method according to claim 1, wherein an amplicon corresponding to a target sequence in the sample differs in length, mass or label from an amplicon corresponding to different target sequence in the sample.

8. The method according to claim 1, wherein the tag section comprises an identifier sequence.

9. The method according to claim 1, wherein for each target sequence in the sample, the corresponding amplicon is provided with an unique identifier sequence.

10. The method according to claim 1, wherein the presence, absence or amount of a target sequence in a sample is detected by detecting the amplicons representing the connected probes based on molecular mass, length, label or sequence.

11. The method according to claim 10, wherein the identifier provides the difference in molecular mass, length or sequence.

12. The method according to claim 1, wherein the target sequence is selected from the group of DNA, RNA, mRNA, polyA+RNA, cDNA, genomic DNA, organellar DNA such as mitochondrial or chloroplast DNA, synthetic nucleic acids, DNA libraries, clone banks or any selection or combinations thereof.

13. The method according to claim 1, wherein the first probe further comprises a first clamp section, and a second probe further comprises a second clamp section, wherein the first and second clamp sections are capable of hybridising to each other.

14. The method according to claim 1, wherein the first or the second probe comprises a further region that is not capable of annealing to the target nucleic acid sequence, which further region is located at the end of the first or second probe at the position of the junction site between the first and second sections of the target nucleic acid sequence.

15. The method according to claim 14, wherein the further region is capable of creating a cleavage structure and whereby exposing the cleavage structure to a cleavage agent will result in cleavage of the cleavage structure when the cleavage structure and cleavage agent are incubated under conditions wherein cleavage can occur.

16. A method for determining the presence, absence or amount of a target nucleotide sequence in a nucleic acid sample, the method comprising the steps of:
 a) providing to a nucleic acid sample a first probe for each target sequence to be detected in the sample, whereby the first probe has a first target specific section that is complementary to a first part of the target sequence and a second probe for each target sequence to be detected in the sample, whereby the second probe is different from the first probe and has a second target specific section that is complementary to a second part of the target sequence, whereby the first and second part of the target sequence are located adjacent to each other, and whereby the second probe further comprises a tag section that is essentially non-complementary to the target sequence, whereby the tag section comprises a first primer binding sequence;
 b) allowing the first and second target specific sections of the first and second probe to anneal to the first and second parts of each target sequence that is present in the sample whereby the first and second target specific sections of the probes are annealed adjacent on the target sequence;
 c) providing means for connecting the first and second target specific sections annealed adjacently to the target sequence and allowing the first and second target specific sections to be connected, to produce a connected probe corresponding to a target sequence in the sample;
 d) providing to the mixture resulting from step c) a compound primer that is different from both the first probe and the second probe and comprises a section that is complementary to at least part of the first target specific section and further comprises a second primer binding section;
 e) allowing the compound primer to anneal to at least part of the first target specific section;
 f) elongating the compound primer;
 g) providing a set of primers comprising a first primer having a sequence essentially identical to the first primer-binding section, and a second primer that is complementary to the second primer-binding section;
 h) amplifying the resulting mixture to produce an amplified sample comprising amplicons that are representations of the connected probes;
 i) determining the presence, absence or amount of a target sequence in the sample by detecting the presence, absence or amount of the corresponding amplicon, and wherein said method is used for high throughput detection of a multiplicity of target nucleotide sequences.

17. The method according to claim 16 for the detection of polymorphisms, preferably single nucleotide polymorphism.

18. The method according to claim 16 for transcript profiling, for the detection of the quantitative abundance of target nucleic acid sequences, for genetic mapping, gene discovery, marker assisted selection, seed quality control, hybrid selection, QTL mapping, bulked segregant analysis, DNA fingerprinting and for disclosing information relating to traits, disease resistance, yield, hybrid vigour, and/or gene function.

19. A method for determining the presence, absence or amount of a target nucleotide sequence in a nucleic acid sample, the method comprising the steps of:
 a) providing to a nucleic acid sample a first probe for each target sequence to be detected in the sample, whereby the first probe has a first target specific section that is complementary to a first part of the target sequence and a second probe, separate from the first probe, for each target sequence to be detected in the sample, whereby the second probe is different from the first probe and has a second target specific section that is complementary to a second part of the target sequence, whereby the first and second part of the target sequence are located adjacent to each other, and whereby the second probe further comprises a tag section that is essentially non-complementary to the target sequence, whereby the tag section comprises a first primer-binding sequence;
 b) allowing the first and second target specific sections of the first and second probe to anneal to the first and second parts of each target sequence that is present in the sample whereby the first and second target specific sections of the probes are annealed adjacent on the target sequence;
 c) providing means for connecting the first and second target specific sections annealed adjacently to the target sequence and allowing the first and second target specific sections to be connected, to produce a connected probe corresponding to a target sequence in the sample;

d) providing to the mixture resulting from step c) a compound primer that is different from both the first probe and the second probe and comprises a section that is complementary to at least part of the first target specific section on the connected probe and further comprises a second primer binding section;

e) allowing the compound primer to anneal to at least part of the first target specific section on the connected probe;

f) elongating both the compound primer and the connected probe to form a double stranded hybrid of the elongated compound primer and the elongated connected probe;

g) providing a set of primers comprising a first primer having a sequence essentially identical to the first primer-binding section, and a second primer that is complementary to the second primer-binding section;

h) amplifying the resulting mixture to produce an amplified sample comprising amplicons that are representations of the connected probe;

i) determining the presence, absence or amount of a target sequence in the sample by detecting the presence, absence or amount of the corresponding amplicon.

* * * * *

UNITED STATES PATENT AND TRADEMARK OFFICE
CERTIFICATE OF CORRECTION

PATENT NO. : 8,808,991 B2  
APPLICATION NO. : 10/570249  
DATED : August 19, 2014  
INVENTOR(S) : René Cornelis Josephus Hogers Page 1 of 1

It is certified that error appears in the above-identified patent and that said Letters Patent is hereby corrected as shown below:

On the title page, Item (12) should read: -- (12) United States Patent  
Hogers --

On the title page, Item (54) should read: --(54) OLA-BASED METHODS FOR THE DETECTION OF TARGET NUCLEIC ACID SEQUENCES--

On the title page, Item (75) should read: --(75) Inventor: René Cornelis Josephus Hogers, Ede (NL)--

Signed and Sealed this  
Tenth Day of February, 2015

Michelle K. Lee  
*Deputy Director of the United States Patent and Trademark Office*